US010223905B2

(12) United States Patent
Zdeblick et al.

(10) Patent No.: US 10,223,905 B2
(45) Date of Patent: Mar. 5, 2019

(54) MOBILE DEVICE AND SYSTEM FOR DETECTION AND COMMUNICATION OF INFORMATION RECEIVED FROM AN INGESTIBLE DEVICE

(71) Applicant: Proteus Digital Health, Inc., Redwood City, CA (US)

(72) Inventors: Mark Zdeblick, Portola Valley, CA (US); Arna Ionescu Stoll, San Francisco, CA (US); William McAllister, Saratoga, CA (US); Kit Yee Au-Yeung, San Francisco, CA (US)

(73) Assignee: PROTEUS DIGITAL HEALTH, INC., Redwood City, CA (US)

( * ) Notice: Subject to any disclaimer, the term of this patent is extended or adjusted under 35 U.S.C. 154(b) by 0 days.

(21) Appl. No.: 15/612,955

(22) Filed: Jun. 2, 2017

(65) Prior Publication Data
US 2017/0270779 A1    Sep. 21, 2017

Related U.S. Application Data

(63) Continuation of application No. 14/234,069, filed as application No. PCT/US2012/047076 on Jul. 17, 2012, now abandoned.
(Continued)

(51) Int. Cl.
*G08C 17/02* (2006.01)
*A61B 5/00* (2006.01)
(Continued)

(52) U.S. Cl.
CPC .............. *G08C 17/02* (2013.01); *A61B 5/073* (2013.01); *A61B 5/4833* (2013.01);
(Continued)

(58) Field of Classification Search
CPC .............. G06F 19/321; G06F 19/3418; G06F 19/3456; G08C 17/02; A61B 5/073; A61B 5/4833; A61B 5/6803; A61B 5/6898
See application file for complete search history.

(56) References Cited

U.S. PATENT DOCUMENTS 3,218,638 A    11/1965 Honig
3,345,989 A    10/1967 Reynolds
(Continued)

FOREIGN PATENT DOCUMENTS

CA    2953847    11/2006
CN    1588649     3/2005
(Continued)

OTHER PUBLICATIONS

AADE, "AADE 37th Annual Meeting San Antonio Aug. 4-7, 2010" American Association of Diabetes Educators Aug. 2010; http://www.diabeteseducator.org/annualmeeting/2010/index.html; 2 pp.
(Continued)

*Primary Examiner* — Sisay Yacob
(74) *Attorney, Agent, or Firm* — K&L Gates LLP

(57) ABSTRACT

A mobile device for detecting an electrical signal generated by an ingestible event marker is disclosed. The mobile device includes a detection subsystem to receive an electrical signal generated by an ingestible event marker from a detection arrangement. A processing subsystem is coupled to the detection subsystem to decode the electrical signal. A radio subsystem is configured to transmit the decoded electrical signal to a wireless node. A system includes the mobile device and the detection arrangement. A method includes receiving the electrical signal generated by the ingestible event marker at the mobile device, decoding the electrical signal to extract information associated with the ingestible event marker, and transmitting the information to a wireless node.

7 Claims, 22 Drawing Sheets

Related U.S. Application Data

(60) Provisional application No. 61/510,434, filed on Jul. 21, 2011.

(51) Int. Cl.
  *A61B 5/07* (2006.01)
  *G06F 19/00* (2018.01)

(52) U.S. Cl.
  CPC ............ *A61B 5/6803* (2013.01); *G06F 19/00* (2013.01); *G06F 19/3418* (2013.01); *A61B 5/6898* (2013.01); *G06F 19/321* (2013.01); *G06F 19/3456* (2013.01)

(56) References Cited

U.S. PATENT DOCUMENTS

| | | |
|---|---|---|
| 3,353,539 A | 11/1967 | Preston |
| 3,409,721 A | 11/1968 | Applezweig |
| 3,419,736 A | 12/1968 | Walsh |
| 3,589,943 A | 6/1971 | Grubb et al. |
| 3,607,788 A | 9/1971 | Adolph |
| 3,628,669 A | 12/1971 | McKinnis et al. |
| 3,642,008 A | 2/1972 | Bolduc |
| 3,679,480 A | 7/1972 | Brown et al. |
| 3,682,160 A | 8/1972 | Murata |
| 3,719,183 A | 3/1973 | Schwartz |
| 3,727,616 A | 4/1973 | Lenzkes |
| 3,799,802 A | 3/1974 | Schneble, Jr. et al. |
| 3,825,016 A | 7/1974 | Lale et al. |
| 3,828,766 A | 8/1974 | Krasnow |
| 3,837,339 A | 9/1974 | Aisenberg et al. |
| 3,893,111 A | 7/1975 | Cotter |
| 3,944,064 A | 3/1976 | Bashaw et al. |
| 3,967,202 A | 6/1976 | Batz |
| 3,989,050 A | 11/1976 | Buchalter |
| 4,017,856 A | 4/1977 | Wiegand |
| 4,055,178 A | 10/1977 | Harrigan |
| 4,062,750 A | 12/1977 | Butler |
| 4,077,397 A | 3/1978 | Ellis |
| 4,077,398 A | 3/1978 | Ellis |
| 4,082,087 A | 4/1978 | Howson |
| 4,090,752 A | 5/1978 | Long |
| 4,105,023 A | 8/1978 | Merchese et al. |
| 4,106,348 A | 8/1978 | Auphan |
| 4,129,125 A | 12/1978 | Lester |
| 4,133,730 A | 1/1979 | DuBois et al. |
| 4,141,349 A | 2/1979 | Ory et al. |
| 4,166,453 A | 9/1979 | McClelland |
| 4,239,046 A | 12/1980 | Ong |
| 4,251,795 A | 2/1981 | Shibasaki et al. |
| 4,269,189 A | 5/1981 | Abraham |
| 4,281,664 A | 8/1981 | Duggan |
| 4,331,654 A | 5/1982 | Morris |
| 4,345,588 A | 8/1982 | Widder et al. |
| 4,418,697 A | 12/1983 | Tama |
| 4,425,117 A | 1/1984 | Hugemann |
| 4,439,196 A | 3/1984 | Higuchi |
| 4,494,950 A | 1/1985 | Fischell |
| 4,526,474 A | 7/1985 | Simon |
| 4,547,391 A | 10/1985 | Jenkins |
| 4,559,950 A | 12/1985 | Vaughan |
| 4,564,363 A | 1/1986 | Bagnall et al. |
| 4,578,061 A | 3/1986 | Lemelson |
| 4,618,533 A | 10/1986 | Steuck |
| 4,635,641 A | 1/1987 | Hoffman |
| 4,654,165 A | 3/1987 | Eisenber |
| 4,663,250 A | 5/1987 | Ong et al. |
| 4,669,479 A | 6/1987 | Dunseath |
| 4,681,111 A | 7/1987 | Silvian |
| 4,687,660 A | 8/1987 | Baker et al. |
| 4,725,997 A | 2/1988 | Urquhart et al. |
| 4,749,575 A | 6/1988 | Rotman et al. |
| 4,763,659 A | 8/1988 | Dunseath |
| 4,767,627 A | 8/1988 | Caldwell et al. |
| 4,784,162 A | 11/1988 | Ricks |
| 4,793,825 A | 12/1988 | Benjamin et al. |
| 4,809,705 A | 3/1989 | Ascher |
| 4,835,373 A | 5/1989 | Adams et al. |
| 4,844,076 A | 7/1989 | Lesho |
| 4,871,974 A | 10/1989 | Davis et al. |
| 4,876,093 A | 10/1989 | Theeuwes et al. |
| 4,896,261 A | 1/1990 | Nolan |
| 4,975,230 A | 12/1990 | Pinkhasov |
| 4,987,897 A | 1/1991 | Funke |
| 5,000,957 A | 3/1991 | Eckenhoff et al. |
| 5,016,634 A | 5/1991 | Vock et al. |
| 5,079,006 A | 1/1992 | Urquhart |
| 5,167,626 A | 12/1992 | Casper |
| 5,176,626 A | 1/1993 | Soehendra |
| 5,179,578 A | 1/1993 | Ishizu |
| 5,245,332 A | 9/1993 | Katzenstein et al. |
| 5,261,402 A | 11/1993 | DiSabito |
| 5,263,481 A | 11/1993 | Axelgaard et al. |
| 5,276,710 A | 1/1994 | Iwasaki |
| 5,279,607 A | 1/1994 | Schentag et al. |
| 5,281,287 A | 1/1994 | Lloyd |
| 5,283,136 A | 2/1994 | Peled et al. |
| 5,288,564 A | 2/1994 | Klein |
| 5,305,745 A | 4/1994 | Zacouto |
| 5,318,557 A | 6/1994 | Gross |
| 5,394,882 A | 3/1995 | Mawhinney |
| 5,395,366 A | 3/1995 | D'Andrea et al. |
| 5,411,535 A | 5/1995 | Fujii et al. |
| 5,412,372 A | 5/1995 | Parkhurst et al. |
| 5,428,961 A | 7/1995 | Sakakibara |
| 5,436,091 A | 7/1995 | Shackle et al. |
| 5,443,461 A | 8/1995 | Atkinson et al. |
| 5,443,843 A | 8/1995 | Curatolo et al. |
| 5,458,141 A | 10/1995 | Neil et al. |
| 5,468,222 A | 11/1995 | Altchuler |
| 5,485,841 A | 1/1996 | Watkin et al. |
| 5,511,548 A | 4/1996 | Riazzi et al. |
| 5,538,007 A | 7/1996 | Gorman |
| 5,551,953 A | 9/1996 | Lattin et al. |
| 5,567,210 A | 10/1996 | Bates et al. |
| 5,596,302 A | 1/1997 | Mastrocola et al. |
| D377,983 S | 2/1997 | Sabri et al. |
| 5,600,548 A | 2/1997 | Nguyen et al. |
| 5,634,466 A | 6/1997 | Gruner |
| 5,634,468 A | 6/1997 | Platt |
| 5,638,406 A | 6/1997 | Sogabe |
| 5,645,063 A | 7/1997 | Straka et al. |
| 5,705,189 A | 1/1998 | Lehmann et al. |
| 5,720,771 A | 2/1998 | Snell |
| 5,738,708 A | 4/1998 | Peachey et al. |
| 5,740,811 A | 4/1998 | Hedberg |
| 5,757,326 A | 5/1998 | Koyama et al. |
| 5,792,048 A | 8/1998 | Schaefer |
| 5,802,467 A | 9/1998 | Salazar |
| 5,833,716 A | 11/1998 | Bar-Or |
| 5,836,474 A | 11/1998 | Wessberg |
| 5,845,265 A | 12/1998 | Woolston |
| 5,862,803 A | 1/1999 | Besson |
| 5,862,808 A | 1/1999 | Albarello |
| 5,868,136 A | 2/1999 | Fox |
| 5,914,701 A | 6/1999 | Gersheneld et al. |
| 5,917,346 A | 6/1999 | Gord |
| 5,921,925 A | 7/1999 | Cartmell et al. |
| 5,925,030 A | 7/1999 | Gross et al. |
| 5,925,066 A | 7/1999 | Kroll et al. |
| 5,957,854 A | 9/1999 | Besson et al. |
| 5,963,132 A | 10/1999 | Yoakum et al. |
| 5,965,629 A | 10/1999 | Jung et al. |
| 5,974,124 A | 10/1999 | Schlueter, Jr. et al. |
| 5,981,166 A | 11/1999 | Mandecki |
| 5,999,846 A | 12/1999 | Pardey et al. |
| 6,009,350 A | 12/1999 | Renken |
| 6,023,631 A | 2/2000 | Cartmell et al. |
| 6,038,464 A | 3/2000 | Axelgaard et al. |
| 6,042,710 A | 3/2000 | Dubrow |
| 6,047,203 A | 4/2000 | Sackner |
| 6,076,016 A | 6/2000 | Feierbach et al. |
| 6,081,734 A | 6/2000 | Batz |
| 6,083,248 A | 7/2000 | Thompson |

(56) References Cited

U.S. PATENT DOCUMENTS

| | | |
|---|---|---|
| 6,090,489 A | 7/2000 | Hayakawa et al. |
| 6,091,975 A | 7/2000 | Daddona et al. |
| 6,095,985 A | 8/2000 | Raymond et al. |
| 6,099,482 A | 8/2000 | Brune et al. |
| 6,115,636 A | 9/2000 | Ryan |
| 6,117,077 A | 9/2000 | Del Mar et al. |
| 6,122,351 A | 9/2000 | Schlueter, Jr. et al. |
| 6,141,592 A | 10/2000 | Pauly |
| 6,149,940 A | 11/2000 | Maggi et al. |
| 6,200,265 B1 | 3/2001 | Walsh et al. |
| 6,204,764 B1 | 3/2001 | Maloney |
| 6,206,702 B1 | 3/2001 | Hayden et al. |
| 6,217,744 B1 | 4/2001 | Crosby |
| 6,231,593 B1 | 5/2001 | Meserol |
| 6,245,057 B1 | 6/2001 | Sieben et al. |
| 6,269,058 B1 | 7/2001 | Yamanoi et al. |
| 6,275,476 B1 | 8/2001 | Wood |
| 6,285,897 B1 | 9/2001 | Kilcoyne et al. |
| 6,287,252 B1 | 9/2001 | Lugo |
| 6,288,629 B1 | 9/2001 | Cofino et al. |
| 6,289,238 B1 | 9/2001 | Besson et al. |
| 6,315,719 B1 | 11/2001 | Rode et al. |
| 6,342,774 B1 | 1/2002 | Kreisinger et al. |
| 6,344,824 B1 | 2/2002 | Takasugi et al. |
| 6,358,202 B1 | 3/2002 | Arent |
| 6,364,834 B1 | 4/2002 | Reuss |
| 6,366,206 B1 | 4/2002 | Ishikawa et al. |
| 6,368,190 B1 | 4/2002 | Easter et al. |
| 6,371,927 B1 | 4/2002 | Brune |
| 6,374,670 B1 | 4/2002 | Spelman |
| 6,380,858 B1 | 4/2002 | Yarin et al. |
| 6,390,088 B1 | 5/2002 | Noehl et al. |
| 6,394,953 B1 | 5/2002 | Devlin et al. |
| 6,394,997 B1 | 5/2002 | Lemelson |
| 6,409,674 B1 | 6/2002 | Brockway et al. |
| 6,411,567 B1 | 6/2002 | Niemiec et al. |
| 6,426,863 B1 | 7/2002 | Munshi |
| 6,432,292 B1 | 8/2002 | Pinto et al. |
| 6,440,069 B1 | 8/2002 | Raymond et al. |
| 6,441,747 B1 | 8/2002 | Khair |
| 6,453,199 B1 | 9/2002 | Kobozev |
| 6,477,424 B1 | 11/2002 | Thompson et al. |
| 6,482,156 B2 | 11/2002 | Lliff |
| 6,494,829 B1 | 12/2002 | New et al. |
| 6,496,705 B1 | 12/2002 | Ng et al. |
| 6,505,077 B1 | 1/2003 | Kast et al. |
| 6,525,996 B1 | 2/2003 | Miyazawa |
| 6,526,315 B1 | 2/2003 | Inagawa |
| 6,531,026 B1 | 3/2003 | Takeichi et al. |
| 6,540,699 B1 | 4/2003 | Smith |
| 6,544,174 B2 | 4/2003 | West |
| 6,564,079 B1 | 5/2003 | Cory |
| 6,572,636 B1 | 6/2003 | Hagen et al. |
| 6,574,425 B1 | 6/2003 | Weiss et al. |
| 6,577,893 B1 | 6/2003 | Besson et al. |
| 6,579,231 B1 | 6/2003 | Phipps |
| 6,595,929 B2 | 7/2003 | Stivoric |
| 6,599,284 B2 | 7/2003 | Faour et al. |
| 6,605,038 B1 | 8/2003 | Teller |
| 6,605,046 B1 | 8/2003 | Del Mar |
| 6,609,018 B2 | 8/2003 | Cory |
| 6,612,984 B1 | 9/2003 | Kerr |
| 6,632,175 B1 | 10/2003 | Marshall |
| 6,632,216 B2 | 10/2003 | Houzego et al. |
| 6,635,279 B2 | 10/2003 | Kolter et al. |
| 6,638,231 B2 | 10/2003 | Govari et al. |
| 6,643,541 B2 | 11/2003 | Mok et al. |
| 6,650,718 B1 | 11/2003 | Fujimura et al. |
| 6,654,638 B1 | 11/2003 | Sweeney |
| 6,663,846 B1 | 12/2003 | McCombs |
| 6,673,474 B2 | 1/2004 | Yamamoto |
| 6,679,830 B2 | 1/2004 | Kolarovic et al. |
| 6,680,923 B1 | 1/2004 | Leon |
| 6,683,493 B1 | 1/2004 | Fujimora et al. |
| 6,689,117 B2 | 2/2004 | Sweeney et al. |
| 6,694,161 B2 | 2/2004 | Mehrotra |
| 6,704,602 B2 | 3/2004 | Berg et al. |
| 6,720,923 B1 | 4/2004 | Hayward et al. |
| 6,738,671 B2 | 5/2004 | Christophersom et al. |
| 6,740,033 B1 | 5/2004 | Olejniczak et al. |
| 6,745,082 B2 | 6/2004 | Axelgaard et al. |
| 6,755,783 B2 | 6/2004 | Cosentino |
| 6,757,523 B2 | 6/2004 | Fry |
| 6,759,968 B2 | 7/2004 | Zierolf |
| 6,771,174 B2 | 8/2004 | Broas |
| 6,773,429 B2 | 8/2004 | Sheppard et al. |
| 6,800,060 B2 | 10/2004 | Marshall |
| 6,801,137 B2 | 10/2004 | Eggers et al. |
| 6,804,558 B2 | 10/2004 | Haller et al. |
| 6,814,706 B2 | 11/2004 | Barton et al. |
| 6,822,554 B2 | 11/2004 | Vrijens et al. |
| 6,836,862 B1 | 12/2004 | Erekson et al. |
| 6,839,659 B2 | 1/2005 | Tarassenko et al. |
| 6,840,904 B2 | 1/2005 | Goldberg |
| 6,842,636 B2 | 1/2005 | Perrault |
| 6,845,272 B1 | 1/2005 | Thomsen |
| 6,864,780 B2 | 3/2005 | Doi |
| 6,879,810 B2 | 4/2005 | Bouet |
| 6,882,881 B1 | 4/2005 | Lesser et al. |
| 6,897,788 B2 | 5/2005 | Khair et al. |
| 6,909,878 B2 | 6/2005 | Haller |
| 6,922,592 B2 | 7/2005 | Thompson et al. |
| 6,928,370 B2 | 8/2005 | Anuzis et al. |
| 6,929,636 B1 | 8/2005 | Von Alten |
| 6,937,150 B2 | 8/2005 | Medema |
| 6,939,292 B2 | 9/2005 | Mizuno |
| 6,942,616 B2 | 9/2005 | Kerr |
| 6,951,536 B2 | 10/2005 | Yokoi |
| 6,957,107 B2 | 10/2005 | Rogers et al. |
| 6,959,929 B2 | 11/2005 | Pugnet et al. |
| 6,968,153 B1 | 11/2005 | Heinonen |
| 6,987,965 B2 | 1/2006 | Ng et al. |
| 6,990,082 B1 | 1/2006 | Zehavi et al. |
| 7,002,476 B2 | 2/2006 | Rapchak |
| 7,004,395 B2 | 2/2006 | Koenck |
| 7,009,634 B2 | 3/2006 | Iddan et al. |
| 7,009,946 B1 | 3/2006 | Kardach |
| 7,013,162 B2 | 3/2006 | Gorsuch |
| 7,016,648 B2 | 3/2006 | Haller |
| 7,020,508 B2 | 3/2006 | Stivoric |
| 7,023,940 B2 | 4/2006 | Nakamura et al. |
| 7,024,248 B2 | 4/2006 | Penner et al. |
| 7,031,745 B2 | 4/2006 | Shen |
| 7,031,857 B2 | 4/2006 | Tarassenko et al. |
| 7,039,453 B2 | 5/2006 | Mullick |
| 7,044,911 B2 | 5/2006 | Drinan et al. |
| 7,046,649 B2 | 5/2006 | Awater et al. |
| 7,050,419 B2 | 5/2006 | Azenkot et al. |
| 7,062,308 B1 | 6/2006 | Jackson |
| 7,069,062 B2 | 6/2006 | Minotani et al. |
| 7,076,437 B1 | 7/2006 | Levy |
| 7,081,693 B2 | 7/2006 | Hamel et al. |
| 7,091,726 B2 | 8/2006 | Sano et al. |
| 7,118,531 B2 | 10/2006 | Krill |
| 7,125,382 B2 | 10/2006 | Zhou et al. |
| 7,127,300 B2 | 10/2006 | Mazar et al. |
| 7,146,228 B2 | 12/2006 | Nielsen |
| 7,146,449 B2 | 12/2006 | Do et al. |
| 7,149,581 B2 | 12/2006 | Goedeke et al. |
| 7,154,071 B2 | 12/2006 | Sattler et al. |
| 7,155,232 B2 | 12/2006 | Godfrey et al. |
| 7,160,258 B2 | 1/2007 | Imran |
| 7,161,484 B2 | 1/2007 | Tsoukalis |
| 7,164,942 B2 | 1/2007 | Avrahami |
| 7,171,166 B2 | 1/2007 | Ng et al. |
| 7,171,177 B2 | 1/2007 | Park et al. |
| 7,171,259 B2 | 1/2007 | Rytky |
| 7,176,784 B2 | 2/2007 | Gilbert et al. |
| 7,187,960 B2 | 3/2007 | Abreu |
| 7,188,767 B2 | 3/2007 | Penuela |
| 7,194,038 B1 | 3/2007 | Inkinen |
| 7,206,630 B1 | 4/2007 | Tarler |
| 7,209,790 B2 | 4/2007 | Thompson et al. |
| 7,215,660 B2 | 5/2007 | Perlman |

(56) References Cited

U.S. PATENT DOCUMENTS

| | | |
|---|---|---|
| 7,215,991 B2 | 5/2007 | Besson |
| 7,218,967 B2 | 5/2007 | Bergelson |
| 7,231,451 B2 | 6/2007 | Law |
| 7,243,118 B2 | 7/2007 | Lou |
| 7,246,521 B2 | 7/2007 | Kim |
| 7,249,212 B2 | 7/2007 | Do |
| 7,252,792 B2 | 8/2007 | Perrault |
| 7,253,716 B2 | 8/2007 | Lovoi et al. |
| 7,261,690 B2 | 8/2007 | Teller |
| 7,270,633 B1 | 9/2007 | Goscha |
| 7,273,454 B2 | 9/2007 | Raymond et al. |
| 7,285,090 B2 | 10/2007 | Stivoric et al. |
| 7,289,855 B2 | 10/2007 | Nghiem |
| 7,291,014 B2 | 11/2007 | Chung et al. |
| 7,291,497 B2 | 11/2007 | Holmes |
| 7,292,139 B2 | 11/2007 | Mazar et al. |
| 7,294,105 B1 | 11/2007 | Islam |
| 7,295,877 B2 | 11/2007 | Govari |
| 7,311,665 B2 | 12/2007 | Hawthorne |
| 7,313,163 B2 | 12/2007 | Liu |
| 7,317,378 B2 | 1/2008 | Jarvis et al. |
| 7,318,808 B2 | 1/2008 | Tarassenko et al. |
| 7,336,732 B1 | 2/2008 | Wiss |
| 7,336,929 B2 | 2/2008 | Yasuda |
| 7,342,895 B2 | 3/2008 | Serpa |
| 7,346,380 B2 | 3/2008 | Axelgaard et al. |
| 7,349,722 B2 | 3/2008 | Witkowski et al. |
| 7,352,998 B2 | 4/2008 | Palin |
| 7,353,258 B2 | 4/2008 | Washburn |
| 7,357,891 B2 | 4/2008 | Yang et al. |
| 7,359,674 B2 | 4/2008 | Markki |
| 7,366,558 B2 | 4/2008 | Virtanen et al. |
| 7,366,675 B1 | 4/2008 | Walker et al. |
| 7,368,190 B2 | 5/2008 | Heller et al. |
| 7,368,191 B2 | 5/2008 | Andelman et al. |
| 7,373,196 B2 | 5/2008 | Ryu et al. |
| 7,375,739 B2 | 5/2008 | Robbins |
| 7,376,435 B2 | 5/2008 | McGowan |
| 7,382,247 B2 | 6/2008 | Welch et al. |
| 7,382,263 B2 | 6/2008 | Danowski et al. |
| 7,387,607 B2 | 6/2008 | Holt |
| 7,388,903 B2 | 6/2008 | Godfrey et al. |
| 7,389,088 B2 | 6/2008 | Kim |
| 7,392,015 B1 | 6/2008 | Farlow |
| 7,395,106 B2 | 7/2008 | Ryu et al. |
| 7,396,330 B2 | 7/2008 | Banet |
| 7,404,968 B2 | 7/2008 | Abrams et al. |
| 7,413,544 B2 | 8/2008 | Kerr |
| 7,414,534 B1 | 8/2008 | Kroll et al. |
| 7,414,543 B2 | 8/2008 | Rye et al. |
| 7,415,242 B1 | 8/2008 | Ngan |
| 7,419,468 B2 | 9/2008 | Shimizu et al. |
| 7,424,268 B2 | 9/2008 | Diener |
| 7,424,319 B2 | 9/2008 | Muehlsteff |
| 7,427,266 B2 | 9/2008 | Ayer et al. |
| 7,449,262 B2 | 11/2008 | Christie et al. |
| 7,462,150 B1 | 12/2008 | Bharmi |
| 7,471,665 B2 | 12/2008 | Perlman |
| 7,485,093 B2 | 2/2009 | Glukhovsky |
| 7,485,095 B2 | 2/2009 | Shusterman |
| 7,499,674 B2 | 3/2009 | Salokannel |
| 7,502,643 B2 | 3/2009 | Farringdon et al. |
| 7,505,795 B1 | 3/2009 | Lim et al. |
| 7,508,248 B2 | 3/2009 | Yoshida |
| 7,510,121 B2 | 3/2009 | Koenck |
| 7,512,448 B2 | 3/2009 | Malick |
| 7,512,860 B2 | 3/2009 | Miyazaki et al. |
| 7,515,043 B2 | 4/2009 | Welch |
| 7,519,416 B2 | 4/2009 | Sula et al. |
| 7,523,756 B2 | 4/2009 | Minai |
| 7,525,426 B2 | 4/2009 | Edelstein |
| 7,539,533 B2 | 5/2009 | Tran |
| 7,542,878 B2 | 6/2009 | Nanikashvili |
| 7,547,278 B2 | 6/2009 | Miyazaki et al. |
| 7,551,590 B2 | 6/2009 | Haller |
| 7,554,452 B2 | 6/2009 | Cole |
| 7,558,620 B2 | 7/2009 | Ishibashi |
| 7,558,965 B2 | 7/2009 | Wheeler et al. |
| 7,575,005 B2 | 8/2009 | Mumford |
| 7,614,743 B2 | 11/2009 | Geiger |
| 7,616,111 B2 | 11/2009 | Covannon |
| 7,616,710 B2 | 11/2009 | Kim et al. |
| 7,617,001 B2 | 11/2009 | Penner et al. |
| 7,639,473 B2 | 12/2009 | Hsu et al. |
| 7,640,802 B2 | 1/2010 | King et al. |
| 7,647,112 B2 | 1/2010 | Tracey |
| 7,647,185 B2 | 1/2010 | Tarassenko et al. |
| 7,653,031 B2 | 1/2010 | Godfrey et al. |
| 7,668,437 B1 | 2/2010 | Yamada et al. |
| 7,672,703 B2 | 3/2010 | Yeo et al. |
| 7,672,714 B2 | 3/2010 | Kuo |
| 7,673,679 B2 | 3/2010 | Harrison et al. |
| 7,678,043 B2 | 3/2010 | Gilad |
| 7,689,437 B1 | 3/2010 | Teller et al. |
| 7,689,833 B2 | 3/2010 | Lange |
| 7,697,994 B2 | 4/2010 | VanDanacker et al. |
| 7,712,288 B2 | 5/2010 | Ramasubramanian et al. |
| 7,720,036 B2 | 5/2010 | Sadri |
| 7,729,776 B2 | 6/2010 | Von Arx et al. |
| 7,733,224 B2 | 6/2010 | Tran |
| 7,736,318 B2 | 6/2010 | Costentino |
| 7,747,454 B2 | 6/2010 | Bartfeld et al. |
| 7,756,587 B2 | 7/2010 | Penner et al. |
| 7,764,996 B2 | 7/2010 | Zhang et al. |
| 7,779,614 B1 | 8/2010 | McGonagle et al. |
| 7,796,043 B2 | 9/2010 | Euliano et al. |
| 7,797,033 B2 | 9/2010 | D'Andrea et al. |
| 7,806,852 B1 | 10/2010 | Jursen |
| 7,809,399 B2 | 10/2010 | Lu |
| 7,811,231 B2 | 10/2010 | Jin et al. |
| 7,844,341 B2 | 11/2010 | Von Arx et al. |
| 7,857,766 B2 | 12/2010 | Lasater et al. |
| 7,860,731 B2 | 12/2010 | Jackson et al. |
| 7,871,734 B2 | 1/2011 | Hertz et al. |
| 7,899,526 B2 | 3/2011 | Benditt et al. |
| 7,904,133 B2 | 3/2011 | Gehman et al. |
| D639,437 S | 6/2011 | Bishay et al. |
| 7,978,064 B2 | 7/2011 | Zdeblick et al. |
| 8,025,149 B2 | 9/2011 | Sterry et al. |
| 8,036,731 B2 | 10/2011 | Kimchy et al. |
| 8,036,748 B2 | 10/2011 | Zdeblick et al. |
| 8,055,334 B2 | 11/2011 | Savage et al. |
| 8,060,249 B2 | 11/2011 | Bear et al. |
| 8,073,707 B2 | 12/2011 | Teller et al. |
| 8,083,128 B2 | 12/2011 | Dembo et al. |
| 8,115,618 B2 | 2/2012 | Robertson et al. |
| 8,123,576 B2 | 2/2012 | Kim |
| 8,135,596 B2 | 3/2012 | Jung et al. |
| 8,177,611 B2 | 5/2012 | Kang |
| 8,180,425 B2 | 5/2012 | Selvitelli et al. |
| 8,185,191 B1 | 5/2012 | Shapiro et al. |
| 8,185,646 B2 | 5/2012 | Headley |
| 8,200,320 B2 | 6/2012 | Kovacs |
| 8,209,018 B2 | 6/2012 | Osorio et al. |
| 8,214,007 B2 | 7/2012 | Baker et al. |
| 8,224,667 B1 | 7/2012 | Miller et al. |
| 8,238,998 B2 | 8/2012 | Park |
| 8,249,686 B2 | 8/2012 | Libbus et al. |
| 8,253,586 B1 | 8/2012 | Matak |
| 8,254,853 B2 | 8/2012 | Rofougaran |
| 8,258,962 B2 | 9/2012 | Robertson et al. |
| 8,262,394 B2 | 9/2012 | Walker et al. |
| 8,271,106 B2 | 9/2012 | Wehba et al. |
| 8,285,356 B2 | 10/2012 | Bly et al. |
| 8,290,574 B2 | 10/2012 | Felid et al. |
| 8,301,232 B2 | 10/2012 | Albert et al. |
| 8,308,640 B2 | 11/2012 | Baldus et al. |
| 8,314,619 B2 | 11/2012 | Takiguchi |
| 8,315,687 B2 | 11/2012 | Cross et al. |
| 8,343,068 B2 | 1/2013 | Najafi et al. |
| 8,369,936 B2 | 2/2013 | Farringdon et al. |
| 8,386,009 B2 | 2/2013 | Lindberg et al. |
| 8,389,003 B2 | 3/2013 | Mintchev et al. |
| 8,404,275 B2 | 3/2013 | Habboushe |

(56) References Cited

U.S. PATENT DOCUMENTS

| | | | |
|---|---|---|---|
| 8,440,274 | B2 | 5/2013 | Wang |
| 8,454,528 | B2 | 6/2013 | Yuen et al. |
| 8,454,561 | B2 | 6/2013 | Uber, III et al. |
| 8,514,086 | B2 | 8/2013 | Harper et al. |
| 8,540,632 | B2 | 9/2013 | Robertson et al. |
| 8,542,123 | B2 | 9/2013 | Robertson |
| 8,547,248 | B2 | 10/2013 | Zdeblick et al. |
| 8,564,432 | B2 | 10/2013 | Covannon et al. |
| 8,564,627 | B2 | 10/2013 | Suzuki et al. |
| 8,583,227 | B2 | 11/2013 | Savage et al. |
| 8,597,186 | B2 | 12/2013 | Hafezi et al. |
| 8,634,838 | B2 | 1/2014 | Hellwig et al. |
| 8,660,645 | B2 | 2/2014 | Stevenson et al. |
| 8,668,280 | B2 | 3/2014 | Heller et al. |
| 8,668,643 | B2 | 3/2014 | Kinast |
| 8,674,825 | B2 | 3/2014 | Robertson et al. |
| 8,718,193 | B2 | 5/2014 | Arne et al. |
| 8,722,085 | B2 | 5/2014 | McKinney et al. |
| 8,762,733 | B2 | 6/2014 | Derchak et al. |
| 8,771,183 | B2 | 7/2014 | Sloan |
| 8,810,260 | B1 | 8/2014 | Zhou |
| 8,810,409 | B2 | 8/2014 | Robertson et al. |
| 8,823,510 | B2 | 9/2014 | Downey et al. |
| 8,836,513 | B2 | 9/2014 | Hafezi et al. |
| 8,838,217 | B2 | 9/2014 | Myr |
| 8,847,766 | B2 | 9/2014 | Zdeblick et al. |
| 8,858,432 | B2 | 10/2014 | Robertson |
| 8,868,453 | B2 | 10/2014 | Zdeblick |
| 8,908,943 | B2 | 12/2014 | Berry et al. |
| 8,926,509 | B2 | 1/2015 | Magar et al. |
| 8,932,221 | B2 | 1/2015 | Colliou et al. |
| 8,945,005 | B2 | 2/2015 | Hafezi et al. |
| 8,956,287 | B2 | 2/2015 | Zdeblick et al. |
| 8,956,288 | B2 | 2/2015 | Hafezi et al. |
| 8,961,412 | B2 | 2/2015 | Hafezi et al. |
| 8,966,973 | B1 | 3/2015 | Milone |
| 8,989,837 | B2 | 3/2015 | Weinstein et al. |
| 9,031,658 | B2 | 5/2015 | Chiao et al. |
| 9,047,746 | B1 | 6/2015 | Euliano et al. |
| 9,060,708 | B2 | 6/2015 | Robertson et al. |
| 9,083,589 | B2 | 7/2015 | Arne et al. |
| 9,088,168 | B2 | 7/2015 | Mach et al. |
| 9,125,868 | B2 | 9/2015 | McKinney et al. |
| 9,189,941 | B2 | 11/2015 | Eschelman et al. |
| 9,198,608 | B2 | 12/2015 | Hafezi et al. |
| 9,226,663 | B2 | 1/2016 | Fei |
| 9,226,679 | B2 | 1/2016 | Balda |
| 9,235,683 | B2 | 1/2016 | Robertson et al. |
| 9,258,035 | B2 | 2/2016 | Robertson et al. |
| 9,270,025 | B2 | 2/2016 | Robertson et al. |
| 9,277,864 | B2 | 3/2016 | Yang et al. |
| 9,278,177 | B2 | 3/2016 | Edwards et al. |
| 9,433,371 | B2 | 9/2016 | Hafezi et al. |
| 9,439,582 | B2 | 9/2016 | Berkman et al. |
| 9,439,599 | B2 | 9/2016 | Thompson et al. |
| 9,444,503 | B2 | 9/2016 | Arne et al. |
| 9,517,012 | B2 | 12/2016 | Lane et al. |
| 9,597,010 | B2 | 3/2017 | Thompson et al. |
| 9,603,550 | B2 | 3/2017 | Behzadi |
| 9,756,874 | B2 | 9/2017 | Arne et al. |
| 9,883,819 | B2 | 2/2018 | Jensen et al. |
| 9,941,931 | B2 | 4/2018 | Zdeblick |
| 2001/0027331 | A1 | 10/2001 | Thompson |
| 2001/0031071 | A1 | 10/2001 | Nichols et al. |
| 2001/0039503 | A1 | 11/2001 | Chan et al. |
| 2001/0044588 | A1 | 11/2001 | Mault |
| 2001/0051766 | A1 | 12/2001 | Gazdinski |
| 2001/0056262 | A1 | 12/2001 | Cabiri et al. |
| 2002/0002326 | A1 | 1/2002 | Causey et al. |
| 2002/0019586 | A1 | 2/2002 | Teller et al. |
| 2002/0026111 | A1 | 2/2002 | Ackerman |
| 2002/0032384 | A1 | 3/2002 | Raymond et al. |
| 2002/0032385 | A1 | 3/2002 | Raymond et al. |
| 2002/0040278 | A1 | 4/2002 | Anuzis et al. |
| 2002/0067270 | A1 | 6/2002 | Yarin et al. |
| 2002/0077620 | A1 | 6/2002 | Sweeney et al. |
| 2002/0082665 | A1* | 6/2002 | Haller ............... A61N 1/37264 607/60 |
| 2002/0128934 | A1 | 9/2002 | Shaer |
| 2002/0132226 | A1* | 9/2002 | Nair .................... A61B 5/0031 435/4 |
| 2002/0138009 | A1 | 9/2002 | Brockway et al. |
| 2002/0184415 | A1 | 12/2002 | Naghavi et al. |
| 2002/0192159 | A1 | 12/2002 | Reitberg |
| 2002/0193669 | A1 | 12/2002 | Glukhovsky |
| 2002/0193846 | A1 | 12/2002 | Pool et al. |
| 2002/0198470 | A1 | 12/2002 | Imran et al. |
| 2003/0017826 | A1 | 1/2003 | Fishman |
| 2003/0023150 | A1* | 1/2003 | Yokoi ................ A61B 1/00016 600/300 |
| 2003/0028226 | A1 | 2/2003 | Thompson |
| 2003/0037063 | A1 | 2/2003 | Schwartz |
| 2003/0063522 | A1 | 4/2003 | Sagar |
| 2003/0065536 | A1 | 4/2003 | Hansen |
| 2003/0076179 | A1 | 4/2003 | Branch et al. |
| 2003/0083559 | A1 | 5/2003 | Thompson |
| 2003/0126593 | A1 | 7/2003 | Mault |
| 2003/0130714 | A1 | 7/2003 | Nielsen et al. |
| 2003/0135128 | A1 | 7/2003 | Suffin et al. |
| 2003/0135392 | A1 | 7/2003 | Vrijens et al. |
| 2003/0152622 | A1 | 8/2003 | Louie-Helm et al. |
| 2003/0158466 | A1 | 8/2003 | Lynn et al. |
| 2003/0158756 | A1 | 8/2003 | Abramson |
| 2003/0162556 | A1 | 8/2003 | Libes |
| 2003/0164401 | A1 | 9/2003 | Andreasson et al. |
| 2003/0167000 | A1 | 9/2003 | Mullick et al. |
| 2003/0171791 | A1 | 9/2003 | KenKnight |
| 2003/0171898 | A1 | 9/2003 | Tarassenko et al. |
| 2003/0181788 | A1 | 9/2003 | Yokoi et al. |
| 2003/0181815 | A1 | 9/2003 | Ebner et al. |
| 2003/0185286 | A1 | 10/2003 | Yuen |
| 2003/0187337 | A1 | 10/2003 | Tarassenko et al. |
| 2003/0187338 | A1 | 10/2003 | Say et al. |
| 2003/0195403 | A1 | 10/2003 | Berner et al. |
| 2003/0198619 | A1 | 10/2003 | Dong et al. |
| 2003/0213495 | A1 | 11/2003 | Fujita et al. |
| 2003/0214579 | A1 | 11/2003 | Iddan |
| 2003/0216622 | A1 | 11/2003 | Meron et al. |
| 2003/0216625 | A1 | 11/2003 | Phipps |
| 2003/0216666 | A1 | 11/2003 | Ericson et al. |
| 2003/0216729 | A1 | 11/2003 | Marchitto |
| 2003/0216793 | A1 | 11/2003 | Karlsson et al. |
| 2003/0229382 | A1 | 12/2003 | Sun et al. |
| 2003/0232895 | A1 | 12/2003 | Omidian et al. |
| 2004/0008123 | A1 | 1/2004 | Carrender et al. |
| 2004/0018476 | A1 | 1/2004 | LaDue |
| 2004/0019172 | A1 | 1/2004 | Yang et al. |
| 2004/0034295 | A1 | 2/2004 | Salganicoff |
| 2004/0049245 | A1 | 3/2004 | Gass |
| 2004/0073095 | A1 | 4/2004 | Causey et al. |
| 2004/0073454 | A1 | 4/2004 | Urquhart et al. |
| 2004/0077995 | A1 | 4/2004 | Ferek-Petric |
| 2004/0082982 | A1 | 4/2004 | Gord et al. |
| 2004/0087839 | A1 | 5/2004 | Raymond et al. |
| 2004/0092801 | A1 | 5/2004 | Drakulic |
| 2004/0106859 | A1 | 6/2004 | Say et al. |
| 2004/0111011 | A1 | 6/2004 | Uchiyama et al. |
| 2004/0115507 | A1 | 6/2004 | Potter et al. |
| 2004/0115517 | A1 | 6/2004 | Fukada et al. |
| 2004/0121015 | A1 | 6/2004 | Chidlaw et al. |
| 2004/0122296 | A1 | 6/2004 | Hatlestad |
| 2004/0122297 | A1 | 6/2004 | Stahmann et al. |
| 2004/0138558 | A1 | 7/2004 | Dunki-Jacobs et al. |
| 2004/0147326 | A1 | 7/2004 | Stiles |
| 2004/0148140 | A1 | 7/2004 | Tarassenko et al. |
| 2004/0153007 | A1 | 8/2004 | Harris |
| 2004/0167226 | A1 | 8/2004 | Serafini |
| 2004/0167801 | A1 | 8/2004 | Say et al. |
| 2004/0171914 | A1 | 9/2004 | Avni |
| 2004/0193020 | A1 | 9/2004 | Chiba |
| 2004/0193029 | A1 | 9/2004 | Gluhovsky |
| 2004/0193446 | A1 | 9/2004 | Mayer et al. |
| 2004/0199222 | A1 | 10/2004 | Sun et al. |
| 2004/0215084 | A1 | 10/2004 | Shimizu et al. |

(56) References Cited

U.S. PATENT DOCUMENTS

| | | |
|---|---|---|
| 2004/0218683 A1 | 11/2004 | Batra |
| 2004/0220643 A1 | 11/2004 | Schmidt |
| 2004/0224644 A1 | 11/2004 | Wu |
| 2004/0225199 A1 | 11/2004 | Evanyk |
| 2004/0253304 A1 | 12/2004 | Gross et al. |
| 2004/0258571 A1 | 12/2004 | Lee et al. |
| 2004/0260154 A1 | 12/2004 | Sidelnik |
| 2004/0267240 A1 | 12/2004 | Gross et al. |
| 2005/0017841 A1 | 1/2005 | Doi |
| 2005/0020887 A1 | 1/2005 | Goldberg |
| 2005/0021103 A1 | 1/2005 | DiLorenzo |
| 2005/0021370 A1 | 1/2005 | Riff |
| 2005/0021372 A1 | 1/2005 | Mikkelsen |
| 2005/0024198 A1 | 2/2005 | Ward |
| 2005/0027175 A1 | 2/2005 | Yang |
| 2005/0027205 A1 | 2/2005 | Tarassenko et al. |
| 2005/0038321 A1 | 2/2005 | Fujita et al. |
| 2005/0038680 A1 | 2/2005 | McMahon |
| 2005/0043583 A1 | 2/2005 | Killmann et al. |
| 2005/0043634 A1 | 2/2005 | Yokoi et al. |
| 2005/0043894 A1 | 2/2005 | Fernandez |
| 2005/0054897 A1 | 3/2005 | Hashimoto et al. |
| 2005/0055014 A1 | 3/2005 | Coppeta et al. |
| 2005/0062644 A1 | 3/2005 | Leci |
| 2005/0065407 A1 | 3/2005 | Nakamura et al. |
| 2005/0070778 A1 | 3/2005 | Lackey |
| 2005/0075145 A1 | 4/2005 | Dvorak et al. |
| 2005/0090753 A1 | 4/2005 | Goor et al. |
| 2005/0092108 A1 | 5/2005 | Andermo |
| 2005/0096514 A1 | 5/2005 | Starkebaum |
| 2005/0096562 A1 | 5/2005 | Delalic et al. |
| 2005/0101843 A1 | 5/2005 | Quinn |
| 2005/0101872 A1 | 5/2005 | Sattler |
| 2005/0107714 A1* | 5/2005 | Matsumura .......... A61B 5/0006 600/509 |
| 2005/0115561 A1 | 6/2005 | Stahmann et al. |
| 2005/0116820 A1 | 6/2005 | Goldreich |
| 2005/0117389 A1 | 6/2005 | Worledge |
| 2005/0121322 A1 | 6/2005 | Say et al. |
| 2005/0131281 A1 | 6/2005 | Ayer et al. |
| 2005/0137480 A1 | 6/2005 | Alt et al. |
| 2005/0143623 A1 | 6/2005 | Kojima |
| 2005/0146594 A1 | 7/2005 | Nakatani et al. |
| 2005/0148883 A1 | 7/2005 | Boesen |
| 2005/0151625 A1 | 7/2005 | Lai |
| 2005/0154277 A1 | 7/2005 | Tang et al. |
| 2005/0154428 A1 | 7/2005 | Bruinsma |
| 2005/0156709 A1 | 7/2005 | Gilbert et al. |
| 2005/0159789 A1 | 7/2005 | Brockway |
| 2005/0165323 A1 | 7/2005 | Montgomery |
| 2005/0177069 A1 | 8/2005 | Takizawa |
| 2005/0182389 A1 | 8/2005 | LaPorte |
| 2005/0187789 A1 | 8/2005 | Hatlestad et al. |
| 2005/0192489 A1 | 9/2005 | Marshall |
| 2005/0197680 A1 | 9/2005 | DelMain et al. |
| 2005/0228268 A1 | 10/2005 | Cole |
| 2005/0234307 A1 | 10/2005 | Heinonen |
| 2005/0240305 A1 | 10/2005 | Bogash et al. |
| 2005/0245794 A1 | 11/2005 | Dinsmoor |
| 2005/0245839 A1 | 11/2005 | Stivoric et al. |
| 2005/0259768 A1 | 11/2005 | Yang et al. |
| 2005/0261559 A1 | 11/2005 | Mumford |
| 2005/0267550 A1 | 12/2005 | Hess et al. |
| 2005/0267556 A1 | 12/2005 | Shuros et al. |
| 2005/0267756 A1 | 12/2005 | Schultz et al. |
| 2005/0277912 A1 | 12/2005 | John |
| 2005/0277999 A1 | 12/2005 | Strother et al. |
| 2005/0280539 A1 | 12/2005 | Pettus |
| 2005/0285732 A1 | 12/2005 | Sengupta et al. |
| 2005/0285746 A1 | 12/2005 | Sengupta |
| 2005/0288594 A1 | 12/2005 | Lewkowicz et al. |
| 2006/0001496 A1 | 1/2006 | Abrosimov et al. |
| 2006/0028727 A1 | 2/2006 | Moon et al. |
| 2006/0036134 A1 | 2/2006 | Tarassenko et al. |
| 2006/0058602 A1 | 3/2006 | Kwiatkowski et al. |
| 2006/0061472 A1 | 3/2006 | Lovoi et al. |
| 2006/0065713 A1 | 3/2006 | Kingery |
| 2006/0068006 A1 | 3/2006 | Begleiter |
| 2006/0074283 A1 | 4/2006 | Henderson |
| 2006/0074319 A1 | 4/2006 | Barnes et al. |
| 2006/0078765 A1 | 4/2006 | Yang et al. |
| 2006/0089858 A1 | 4/2006 | Ling |
| 2006/0095091 A1 | 5/2006 | Drew |
| 2006/0095093 A1 | 5/2006 | Bettesh et al. |
| 2006/0100533 A1 | 5/2006 | Han |
| 2006/0109058 A1 | 5/2006 | Keating |
| 2006/0110962 A1 | 5/2006 | Powell |
| 2006/0122474 A1 | 6/2006 | Teller et al. |
| 2006/0122667 A1 | 6/2006 | Chavan et al. |
| 2006/0129060 A1 | 6/2006 | Lee et al. |
| 2006/0136266 A1 | 6/2006 | Tarassenko et al. |
| 2006/0142648 A1 | 6/2006 | Banet |
| 2006/0145876 A1 | 7/2006 | Kimura |
| 2006/0148254 A1 | 7/2006 | McLean |
| 2006/0149339 A1 | 7/2006 | Burnes |
| 2006/0155174 A1 | 7/2006 | Glukhovsky et al. |
| 2006/0155183 A1 | 7/2006 | Kroecker |
| 2006/0158820 A1 | 7/2006 | Takiguchi |
| 2006/0161225 A1 | 7/2006 | Sormann et al. |
| 2006/0179949 A1 | 8/2006 | Kim |
| 2006/0183992 A1 | 8/2006 | Kawashima |
| 2006/0183993 A1 | 8/2006 | Horn |
| 2006/0184092 A1 | 8/2006 | Atanasoska et al. |
| 2006/0204738 A1 | 9/2006 | Dubrow et al. |
| 2006/0204764 A1 | 9/2006 | Hirao et al. |
| 2006/0210626 A1 | 9/2006 | Spaeder |
| 2006/0216603 A1 | 9/2006 | Choi |
| 2006/0218011 A1 | 9/2006 | Walker |
| 2006/0229053 A1 | 10/2006 | Sivard |
| 2006/0235489 A1 | 10/2006 | Drew |
| 2006/0243288 A1 | 11/2006 | Kim et al. |
| 2006/0247505 A1 | 11/2006 | Siddiqui |
| 2006/0253004 A1 | 11/2006 | Frisch et al. |
| 2006/0253005 A1 | 11/2006 | Drinan |
| 2006/0255064 A1 | 11/2006 | Donaldson |
| 2006/0265246 A1 | 11/2006 | Hoag |
| 2006/0267774 A1 | 11/2006 | Feinberg et al. |
| 2006/0270346 A1 | 11/2006 | Ibrahim |
| 2006/0273882 A1 | 12/2006 | Posamentier |
| 2006/0276702 A1 | 12/2006 | McGinnis |
| 2006/0280227 A1 | 12/2006 | Pinkney |
| 2006/0282001 A1 | 12/2006 | Noel |
| 2006/0285607 A1 | 12/2006 | Strodtbeck et al. |
| 2006/0287693 A1 | 12/2006 | Kraft et al. |
| 2006/0289640 A1 | 12/2006 | Mercure |
| 2006/0293607 A1 | 12/2006 | Alt |
| 2007/0000776 A1 | 1/2007 | Karube et al. |
| 2007/0002038 A1 | 1/2007 | Suzuki |
| 2007/0006636 A1 | 1/2007 | King et al. |
| 2007/0008113 A1 | 1/2007 | Spoonhower et al. |
| 2007/0016089 A1 | 1/2007 | Fischell et al. |
| 2007/0027386 A1 | 2/2007 | Such |
| 2007/0027388 A1 | 2/2007 | Chou |
| 2007/0038054 A1 | 2/2007 | Zhou |
| 2007/0049339 A1 | 3/2007 | Barak et al. |
| 2007/0055098 A1 | 3/2007 | Shimizu et al. |
| 2007/0060797 A1 | 3/2007 | Ball |
| 2007/0060800 A1 | 3/2007 | Drinan et al. |
| 2007/0066929 A1 | 3/2007 | Ferren et al. |
| 2007/0072156 A1 | 3/2007 | Kaufman et al. |
| 2007/0073353 A1 | 3/2007 | Rooney et al. |
| 2007/0088194 A1 | 4/2007 | Tahar |
| 2007/0096765 A1 | 5/2007 | Kagan |
| 2007/0106346 A1 | 5/2007 | Bergelson |
| 2007/0123772 A1 | 5/2007 | Euliano |
| 2007/0129622 A1 | 6/2007 | Bourget |
| 2007/0130287 A1 | 6/2007 | Kumar |
| 2007/0135691 A1 | 6/2007 | Zingelewicz et al. |
| 2007/0135803 A1 | 6/2007 | Belson |
| 2007/0142721 A1 | 6/2007 | Berner et al. |
| 2007/0156016 A1 | 7/2007 | Betesh |
| 2007/0160789 A1 | 7/2007 | Merical |
| 2007/0162089 A1 | 7/2007 | Mosesov |
| 2007/0162090 A1 | 7/2007 | Penner |

(56) References Cited

U.S. PATENT DOCUMENTS

| | | |
|---|---|---|
| 2007/0167495 A1 | 7/2007 | Brown et al. |
| 2007/0167848 A1 | 7/2007 | Kuo et al. |
| 2007/0173701 A1 | 7/2007 | Al-Ali |
| 2007/0179347 A1 | 8/2007 | Tarassenko et al. |
| 2007/0179371 A1 | 8/2007 | Peyser et al. |
| 2007/0180047 A1 | 8/2007 | Dong et al. |
| 2007/0185393 A1 | 8/2007 | Zhou |
| 2007/0191002 A1 | 8/2007 | Ge |
| 2007/0196456 A1 | 8/2007 | Stevens |
| 2007/0207793 A1 | 9/2007 | Myer |
| 2007/0207858 A1 | 9/2007 | Breving |
| 2007/0208233 A1 | 9/2007 | Kovacs |
| 2007/0213659 A1 | 9/2007 | Trovato et al. |
| 2007/0237719 A1 | 10/2007 | Jones |
| 2007/0244370 A1 | 10/2007 | Kuo et al. |
| 2007/0244810 A1 | 10/2007 | Rudolph |
| 2007/0249946 A1 | 10/2007 | Kumar et al. |
| 2007/0255198 A1 | 11/2007 | Leong et al. |
| 2007/0255330 A1 | 11/2007 | Lee |
| 2007/0270672 A1 | 11/2007 | Hayter |
| 2007/0279217 A1 | 12/2007 | Venkatraman |
| 2007/0282174 A1 | 12/2007 | Sabatino |
| 2007/0282177 A1 | 12/2007 | Pilz |
| 2007/0291715 A1 | 12/2007 | Laroia et al. |
| 2007/0299480 A1 | 12/2007 | Hill |
| 2008/0004503 A1 | 1/2008 | Nisani et al. |
| 2008/0014866 A1 | 1/2008 | Lipowshi |
| 2008/0015421 A1 | 1/2008 | Penner |
| 2008/0015494 A1 | 1/2008 | Santini et al. |
| 2008/0015893 A1 | 1/2008 | Miller et al. |
| 2008/0020037 A1 | 1/2008 | Robertson et al. |
| 2008/0021519 A1 | 1/2008 | DeGeest |
| 2008/0021521 A1 | 1/2008 | Shah |
| 2008/0027679 A1 | 1/2008 | Shklarski |
| 2008/0033273 A1 | 2/2008 | Zhou |
| 2008/0033301 A1 | 2/2008 | Dellavecchia et al. |
| 2008/0038588 A1 | 2/2008 | Lee |
| 2008/0039700 A1 | 2/2008 | Drinan et al. |
| 2008/0045843 A1 | 2/2008 | Tsuji et al. |
| 2008/0046038 A1 | 2/2008 | Hill |
| 2008/0051647 A1 | 2/2008 | Wu et al. |
| 2008/0051667 A1 | 2/2008 | Goldreich |
| 2008/0051767 A1 | 2/2008 | Rossing et al. |
| 2008/0058614 A1 | 3/2008 | Banet |
| 2008/0062856 A1 | 3/2008 | Feher |
| 2008/0065168 A1 | 3/2008 | Bitton et al. |
| 2008/0074307 A1 | 3/2008 | Boric-Lubecke |
| 2008/0077015 A1 | 3/2008 | Botic-Lubecke |
| 2008/0077028 A1 | 3/2008 | Schaldach et al. |
| 2008/0077188 A1 | 3/2008 | Denker et al. |
| 2008/0077430 A1 | 3/2008 | Singer et al. |
| 2008/0091089 A1 | 4/2008 | Guillory et al. |
| 2008/0091114 A1 | 4/2008 | Min |
| 2008/0097549 A1 | 4/2008 | Colbaugh |
| 2008/0097917 A1 | 4/2008 | Dicks |
| 2008/0099366 A1 | 5/2008 | Niemic et al. |
| 2008/0103440 A1 | 5/2008 | Ferren et al. |
| 2008/0112885 A1 | 5/2008 | Okunev et al. |
| 2008/0114224 A1 | 5/2008 | Bandy et al. |
| 2008/0119705 A1 | 5/2008 | Patel |
| 2008/0119716 A1 | 5/2008 | Boric-Lubecke |
| 2008/0121825 A1 | 5/2008 | Trovato et al. |
| 2008/0137566 A1 | 6/2008 | Marholev |
| 2008/0139907 A1 | 6/2008 | Rao et al. |
| 2008/0140403 A1 | 6/2008 | Hughes et al. |
| 2008/0146871 A1 | 6/2008 | Arneson et al. |
| 2008/0146889 A1 | 6/2008 | Young |
| 2008/0146892 A1 | 6/2008 | LeBoeuf |
| 2008/0154104 A1 | 6/2008 | Lamego |
| 2008/0166992 A1 | 7/2008 | Ricordi |
| 2008/0175898 A1 | 7/2008 | Jones et al. |
| 2008/0183245 A1 | 7/2008 | Van Oort |
| 2008/0188763 A1 | 8/2008 | John et al. |
| 2008/0188837 A1 | 8/2008 | Belsky et al. |
| 2008/0194912 A1 | 8/2008 | Trovato et al. |
| 2008/0208009 A1 | 8/2008 | Shklarski |
| 2008/0214901 A1 | 9/2008 | Gehman |
| 2008/0214903 A1 | 9/2008 | Orbach |
| 2008/0214985 A1 | 9/2008 | Yanaki |
| 2008/0223936 A1 | 9/2008 | Mickle et al. |
| 2008/0243020 A1 | 10/2008 | Chou |
| 2008/0249360 A1 | 10/2008 | Li |
| 2008/0262320 A1 | 10/2008 | Schaefer et al. |
| 2008/0262336 A1 | 10/2008 | Ryu |
| 2008/0269664 A1 | 10/2008 | Trovato et al. |
| 2008/0275312 A1 | 11/2008 | Mosesov |
| 2008/0281636 A1 | 11/2008 | Jung et al. |
| 2008/0288026 A1 | 11/2008 | Cross et al. |
| 2008/0288027 A1 | 11/2008 | Kroll |
| 2008/0294020 A1 | 11/2008 | Sapounas |
| 2008/0299197 A1 | 12/2008 | Toneguzzo et al. |
| 2008/0300572 A1 | 12/2008 | Rankers |
| 2008/0303638 A1 | 12/2008 | Nguyen |
| 2008/0303665 A1 | 12/2008 | Naik et al. |
| 2008/0306357 A1 | 12/2008 | Korman |
| 2008/0306362 A1 | 12/2008 | Davis |
| 2008/0311852 A1 | 12/2008 | Hansen |
| 2008/0312522 A1 | 12/2008 | Rowlandson |
| 2009/0006133 A1 | 1/2009 | Weinert |
| 2009/0009330 A1 | 1/2009 | Sakama et al. |
| 2009/0009332 A1 | 1/2009 | Nunez et al. |
| 2009/0024045 A1 | 1/2009 | Prakash |
| 2009/0024112 A1 | 1/2009 | Edwards et al. |
| 2009/0030293 A1 | 1/2009 | Cooper et al. |
| 2009/0030297 A1 | 1/2009 | Miller |
| 2009/0034209 A1 | 2/2009 | Joo |
| 2009/0043171 A1 | 2/2009 | Rule |
| 2009/0048498 A1 | 2/2009 | Riskey |
| 2009/0062634 A1 | 3/2009 | Say et al. |
| 2009/0062670 A1 | 3/2009 | Sterling |
| 2009/0062730 A1 | 3/2009 | Woo |
| 2009/0069642 A1 | 3/2009 | Gao |
| 2009/0069655 A1 | 3/2009 | Say et al. |
| 2009/0069656 A1 | 3/2009 | Say et al. |
| 2009/0069657 A1 | 3/2009 | Say et al. |
| 2009/0069658 A1 | 3/2009 | Say et al. |
| 2009/0076340 A1 | 3/2009 | Libbus et al. |
| 2009/0076343 A1 | 3/2009 | James |
| 2009/0076350 A1 | 3/2009 | Bly et al. |
| 2009/0076397 A1 | 3/2009 | Libbus et al. |
| 2009/0087483 A1 | 4/2009 | Sison |
| 2009/0088618 A1 | 4/2009 | Arneson |
| 2009/0099435 A1 | 4/2009 | Say et al. |
| 2009/0105561 A1 | 4/2009 | Boydon et al. |
| 2009/0110148 A1 | 4/2009 | Zhang |
| 2009/0112626 A1 | 4/2009 | Talbot |
| 2009/0124871 A1 | 5/2009 | Arshak |
| 2009/0131774 A1 | 5/2009 | Sweitzer |
| 2009/0134181 A1 | 5/2009 | Wachman et al. |
| 2009/0135886 A1 | 5/2009 | Robertson et al. |
| 2009/0142853 A1 | 6/2009 | Warrington et al. |
| 2009/0149708 A1 | 6/2009 | Hyde et al. |
| 2009/0149839 A1 | 6/2009 | Hyde et al. |
| 2009/0157113 A1 | 6/2009 | Marcotte |
| 2009/0157358 A1 | 6/2009 | Kim |
| 2009/0161602 A1 | 6/2009 | Matsumoto |
| 2009/0163789 A1 | 6/2009 | Say et al. |
| 2009/0171180 A1 | 7/2009 | Pering |
| 2009/0173628 A1 | 7/2009 | Say et al. |
| 2009/0177055 A1 | 7/2009 | Say et al. |
| 2009/0177056 A1 | 7/2009 | Say et al. |
| 2009/0177057 A1 | 7/2009 | Say et al. |
| 2009/0177058 A1 | 7/2009 | Say et al. |
| 2009/0177059 A1 | 7/2009 | Say et al. |
| 2009/0177060 A1 | 7/2009 | Say et al. |
| 2009/0177061 A1 | 7/2009 | Say et al. |
| 2009/0177062 A1 | 7/2009 | Say et al. |
| 2009/0177063 A1 | 7/2009 | Say et al. |
| 2009/0177064 A1 | 7/2009 | Say et al. |
| 2009/0177065 A1 | 7/2009 | Say et al. |
| 2009/0177066 A1 | 7/2009 | Say et al. |
| 2009/0182206 A1 | 7/2009 | Najafi |
| 2009/0182207 A1 | 7/2009 | Riskey et al. |
| 2009/0182212 A1 | 7/2009 | Say et al. |

(56) References Cited

U.S. PATENT DOCUMENTS

| | | |
|---|---|---|
| 2009/0182213 A1 | 7/2009 | Say et al. |
| 2009/0182214 A1 | 7/2009 | Say et al. |
| 2009/0182215 A1 | 7/2009 | Say et al. |
| 2009/0182388 A1 | 7/2009 | Von Arx |
| 2009/0187088 A1 | 7/2009 | Say et al. |
| 2009/0187089 A1 | 7/2009 | Say et al. |
| 2009/0187090 A1 | 7/2009 | Say et al. |
| 2009/0187091 A1 | 7/2009 | Say et al. |
| 2009/0187092 A1 | 7/2009 | Say et al. |
| 2009/0187093 A1 | 7/2009 | Say et al. |
| 2009/0187094 A1 | 7/2009 | Say et al. |
| 2009/0187095 A1 | 7/2009 | Say et al. |
| 2009/0187381 A1 | 7/2009 | King et al. |
| 2009/0192351 A1 | 7/2009 | Nishino |
| 2009/0192368 A1 | 7/2009 | Say et al. |
| 2009/0192369 A1 | 7/2009 | Say et al. |
| 2009/0192370 A1 | 7/2009 | Say et al. |
| 2009/0192371 A1 | 7/2009 | Say et al. |
| 2009/0192372 A1 | 7/2009 | Say et al. |
| 2009/0192373 A1 | 7/2009 | Say et al. |
| 2009/0192374 A1 | 7/2009 | Say et al. |
| 2009/0192375 A1 | 7/2009 | Say et al. |
| 2009/0192376 A1 | 7/2009 | Say et al. |
| 2009/0192377 A1 | 7/2009 | Say et al. |
| 2009/0192378 A1 | 7/2009 | Say et al. |
| 2009/0192379 A1 | 7/2009 | Say et al. |
| 2009/0198115 A1 | 8/2009 | Say et al. |
| 2009/0198116 A1 | 8/2009 | Say et al. |
| 2009/0198175 A1 | 8/2009 | Say et al. |
| 2009/0203964 A1* | 8/2009 | Shimizu ............... A61B 1/041 600/109 |
| 2009/0203971 A1 | 8/2009 | Sciarappa |
| 2009/0203972 A1 | 8/2009 | Heneghan |
| 2009/0203978 A1 | 8/2009 | Say et al. |
| 2009/0204265 A1 | 8/2009 | Hackett |
| 2009/0210164 A1 | 8/2009 | Say et al. |
| 2009/0216101 A1 | 8/2009 | Say et al. |
| 2009/0216102 A1 | 8/2009 | Say et al. |
| 2009/0227876 A1 | 9/2009 | Tran |
| 2009/0227940 A1 | 9/2009 | Say et al. |
| 2009/0227941 A1 | 9/2009 | Say et al. |
| 2009/0227988 A1 | 9/2009 | Wood et al. |
| 2009/0228214 A1 | 9/2009 | Say et al. |
| 2009/0231125 A1 | 9/2009 | Baldus |
| 2009/0234200 A1 | 9/2009 | Husheer |
| 2009/0243833 A1 | 10/2009 | Huang |
| 2009/0247836 A1 | 10/2009 | Cole et al. |
| 2009/0253960 A1 | 10/2009 | Takenaka et al. |
| 2009/0264714 A1 | 10/2009 | Chou |
| 2009/0264964 A1 | 10/2009 | Abrahamson |
| 2009/0265186 A1 | 10/2009 | Tarassenko et al. |
| 2009/0273467 A1 | 11/2009 | Elixmann |
| 2009/0277815 A1 | 11/2009 | Kohl et al. |
| 2009/0281539 A1 | 11/2009 | Selig |
| 2009/0287109 A1 | 11/2009 | Ferren et al. |
| 2009/0292194 A1 | 11/2009 | Libbus et al. |
| 2009/0295548 A1 | 12/2009 | Ronkka |
| 2009/0296677 A1 | 12/2009 | Mahany |
| 2009/0301925 A1 | 12/2009 | Alloro et al. |
| 2009/0303920 A1 | 12/2009 | Mahany |
| 2009/0306633 A1 | 12/2009 | Trovato et al. |
| 2009/0312619 A1 | 12/2009 | Say et al. |
| 2009/0318303 A1 | 12/2009 | Delamarche et al. |
| 2009/0318761 A1 | 12/2009 | Rabinovitz |
| 2009/0318779 A1 | 12/2009 | Tran |
| 2009/0318783 A1 | 12/2009 | Rohde |
| 2009/0318793 A1 | 12/2009 | Datta |
| 2010/0001841 A1 | 1/2010 | Cardullo |
| 2010/0006585 A1 | 1/2010 | Flowers et al. |
| 2010/0010330 A1 | 1/2010 | Rankers |
| 2010/0015584 A1 | 1/2010 | Singer et al. |
| 2010/0033324 A1 | 2/2010 | Shimizu et al. |
| 2010/0036269 A1 | 2/2010 | Ferren et al. |
| 2010/0049004 A1 | 2/2010 | Edman et al. |
| 2010/0049006 A1 | 2/2010 | Magar |
| 2010/0049012 A1 | 2/2010 | Dijksman et al. |
| 2010/0049069 A1 | 2/2010 | Tarassenko et al. |
| 2010/0056878 A1 | 3/2010 | Partin |
| 2010/0056891 A1 | 3/2010 | Say et al. |
| 2010/0056939 A1 | 3/2010 | Tarassenko et al. |
| 2010/0057041 A1 | 3/2010 | Hayter |
| 2010/0062709 A1 | 3/2010 | Kato |
| 2010/0063438 A1 | 3/2010 | Bengtsson |
| 2010/0063841 A1 | 3/2010 | D'Ambrosia et al. |
| 2010/0069002 A1 | 3/2010 | Rong |
| 2010/0081894 A1* | 4/2010 | Zdeblick ............... A61B 5/0031 600/302 |
| 2010/0082367 A1 | 4/2010 | Hains et al. |
| 2010/0099967 A1 | 4/2010 | Say et al. |
| 2010/0099968 A1 | 4/2010 | Say et al. |
| 2010/0099969 A1 | 4/2010 | Say et al. |
| 2010/0100077 A1 | 4/2010 | Rush |
| 2010/0100078 A1 | 4/2010 | Say et al. |
| 2010/0100237 A1 | 4/2010 | Ratnakar |
| 2010/0106001 A1 | 4/2010 | Say et al. |
| 2010/0118853 A1 | 5/2010 | Godfrey |
| 2010/0131434 A1 | 5/2010 | Magent et al. |
| 2010/0139672 A1 | 6/2010 | Kroll et al. |
| 2010/0160742 A1 | 6/2010 | Seidl et al. |
| 2010/0168659 A1 | 7/2010 | Say et al. |
| 2010/0179398 A1 | 7/2010 | Say et al. |
| 2010/0183199 A1 | 7/2010 | Smith et al. |
| 2010/0185055 A1* | 7/2010 | Robertson ............ A61B 5/0031 600/117 |
| 2010/0191073 A1 | 7/2010 | Tarassenko et al. |
| 2010/0203394 A1 | 8/2010 | Bae et al. |
| 2010/0210299 A1 | 8/2010 | Gorbachov |
| 2010/0217100 A1* | 8/2010 | LeBoeuf ................. G06F 19/00 600/382 |
| 2010/0222652 A1 | 9/2010 | Cho |
| 2010/0228113 A1 | 9/2010 | Solosko |
| 2010/0233026 A1 | 9/2010 | Ismagilov et al. |
| 2010/0234706 A1 | 9/2010 | Gilland |
| 2010/0234715 A1 | 9/2010 | Shin |
| 2010/0234914 A1 | 9/2010 | Shen |
| 2010/0245091 A1 | 9/2010 | Singh |
| 2010/0249541 A1 | 9/2010 | Geva et al. |
| 2010/0249881 A1 | 9/2010 | Corndorf |
| 2010/0256461 A1 | 10/2010 | Mohamedali |
| 2010/0259543 A1 | 10/2010 | Tarassenko et al. |
| 2010/0268048 A1 | 10/2010 | Say et al. |
| 2010/0268049 A1 | 10/2010 | Say et al. |
| 2010/0268050 A1 | 10/2010 | Say et al. |
| 2010/0268288 A1 | 10/2010 | Hunter et al. |
| 2010/0274111 A1 | 10/2010 | Say et al. |
| 2010/0280345 A1 | 11/2010 | Say et al. |
| 2010/0280346 A1 | 11/2010 | Say et al. |
| 2010/0295694 A1 | 11/2010 | Kauffman et al. |
| 2010/0298668 A1 | 11/2010 | Hafezi et al. |
| 2010/0298730 A1 | 11/2010 | Tarassenko et al. |
| 2010/0299155 A1 | 11/2010 | Findlay et al. |
| 2010/0312188 A1 | 12/2010 | Robertson et al. |
| 2010/0312577 A1 | 12/2010 | Goodnow et al. |
| 2010/0312580 A1 | 12/2010 | Tarassenko et al. |
| 2010/0332443 A1 | 12/2010 | Gartenberg |
| 2011/0004079 A1 | 1/2011 | Al Ali et al. |
| 2011/0009715 A1 | 1/2011 | O'Reilly et al. |
| 2011/0021983 A1 | 1/2011 | Jurson |
| 2011/0029622 A1 | 2/2011 | Walker et al. |
| 2011/0050431 A1 | 3/2011 | Hood et al. |
| 2011/0054265 A1 | 3/2011 | Hafezi et al. |
| 2011/0065983 A1 | 3/2011 | Hafezi et al. |
| 2011/0077660 A1 | 3/2011 | Janik et al. |
| 2011/0081860 A1 | 4/2011 | Brown et al. |
| 2011/0105864 A1 | 5/2011 | Robertson et al. |
| 2011/0112686 A1 | 5/2011 | Nolan et al. |
| 2011/0124983 A1 | 5/2011 | Kroll et al. |
| 2011/0144470 A1 | 6/2011 | Mazar et al. |
| 2011/0160549 A1 | 6/2011 | Saroka et al. |
| 2011/0212782 A1 | 9/2011 | Thompson et al. |
| 2011/0224912 A1 | 9/2011 | Bhavaraju et al. |
| 2011/0230732 A1 | 9/2011 | Edman et al. |
| 2011/0237924 A1 | 9/2011 | McGusty et al. |
| 2011/0270112 A1 | 11/2011 | Manera et al. |

(56) References Cited

U.S. PATENT DOCUMENTS

| | | |
|---|---|---|
| 2011/0270135 A1 | 11/2011 | Dooley et al. |
| 2011/0279963 A1 | 11/2011 | Kumar et al. |
| 2012/0024889 A1 | 2/2012 | Robertson et al. |
| 2012/0029309 A1 | 2/2012 | Paquet et al. |
| 2012/0032816 A1 | 2/2012 | Cho et al. |
| 2012/0062371 A1 | 3/2012 | Radivojevic et al. |
| 2012/0071743 A1 | 3/2012 | Todorov et al. |
| 2012/0083715 A1 | 4/2012 | Yuen et al. |
| 2012/0089000 A1 | 4/2012 | Bishay et al. |
| 2012/0101396 A1 | 4/2012 | Solosko et al. |
| 2012/0116184 A1* | 5/2012 | Shieh ............... A61B 5/01 600/301 |
| 2012/0179004 A1 | 7/2012 | Roesicke et al. |
| 2012/0197144 A1 | 8/2012 | Christ et al. |
| 2012/0214140 A1 | 8/2012 | Brynelson et al. |
| 2012/0265544 A1 | 10/2012 | Hwang et al. |
| 2012/0310070 A1 | 12/2012 | Kumar et al. |
| 2012/0316413 A1 | 12/2012 | Liu et al. |
| 2013/0002423 A1 | 1/2013 | Robertson et al. |
| 2013/0030259 A1 | 1/2013 | Thomsen et al. |
| 2013/0057385 A1 | 3/2013 | Murakami et al. |
| 2013/0060115 A1 | 3/2013 | Gehman et al. |
| 2013/0073312 A1 | 3/2013 | Thompson et al. |
| 2013/0171596 A1 | 7/2013 | French |
| 2013/0185228 A1 | 7/2013 | Dresner |
| 2013/0196012 A1 | 8/2013 | Dill |
| 2013/0275296 A1 | 10/2013 | Tietzen et al. |
| 2013/0328416 A1 | 12/2013 | Whitworth et al. |
| 2013/0338452 A1 | 12/2013 | Robertson et al. |
| 2014/0004492 A1 | 1/2014 | O'Reilly et al. |
| 2014/0039445 A1 | 2/2014 | Austin et al. |
| 2014/0051965 A1 | 2/2014 | Zdeblick et al. |
| 2014/0203950 A1 | 7/2014 | Zdeblick et al. |
| 2014/0280125 A1 | 9/2014 | Bhardwaj et al. |
| 2014/0308930 A1 | 10/2014 | Tran |
| 2014/0315170 A1 | 10/2014 | Ionescu et al. |
| 2014/0349256 A1 | 11/2014 | Connor |
| 2014/0374276 A1 | 12/2014 | Guthrie et al. |
| 2015/0051465 A1 | 2/2015 | Robertson et al. |
| 2015/0080678 A1 | 3/2015 | Frank et al. |
| 2015/0080679 A1 | 3/2015 | Frank et al. |
| 2015/0080680 A1 | 3/2015 | Zdeblick et al. |
| 2015/0080681 A1 | 3/2015 | Hafezi et al. |
| 2015/0127737 A1 | 5/2015 | Thompson et al. |
| 2015/0127738 A1 | 5/2015 | Thompson et al. |
| 2015/0149375 A1 | 5/2015 | Thompson et al. |
| 2015/0165313 A1 | 6/2015 | Thompson et al. |
| 2015/0182463 A1 | 7/2015 | Hafezi et al. |
| 2015/0193593 A1 | 7/2015 | Zdeblick et al. |
| 2015/0230728 A1 | 8/2015 | Hafezi et al. |
| 2016/0106339 A1 | 4/2016 | Behzadi et al. |
| 2016/0155316 A1 | 6/2016 | Hafezi et al. |
| 2017/0215761 A1 | 8/2017 | Zdeblick |
| 2017/0290513 A1 | 10/2017 | O'Reilly et al. |
| 2017/0303818 A1 | 10/2017 | Behzadi et al. |
| 2018/0026680 A1 | 1/2018 | Shirvani et al. |

FOREIGN PATENT DOCUMENTS

| | | |
|---|---|---|
| CN | 2748032 | 12/2005 |
| CN | 1991868 | 7/2007 |
| CN | 101005470 | 7/2007 |
| CN | 201076456 | 6/2008 |
| CN | 101524267 | 9/2009 |
| DE | 10313005 | 10/2004 |
| EP | 0344939 | 12/1989 |
| EP | 0526166 | 2/1993 |
| EP | 1199670 | 4/2002 |
| EP | 1246356 | 10/2002 |
| EP | 1342447 | 9/2003 |
| EP | 1534054 | 5/2005 |
| EP | 1702553 | 9/2006 |
| EP | 1098591 | 1/2007 |
| EP | 1789128 | 5/2007 |
| EP | 2143369 | 1/2010 |
| GB | 775071 | 5/1957 |
| GB | 2432862 | 6/2007 |
| IL | 172917 | 6/2010 |
| JP | S6117949 | 1/1986 |
| JP | S63280393 | 11/1988 |
| JP | H01285247 | 11/1989 |
| JP | 05228128 | 9/1993 |
| JP | H0884779 | 4/1996 |
| JP | 09330159 | 12/1997 |
| JP | 1014898 | 1/1998 |
| JP | H11195415 | 7/1999 |
| JP | 2000506410 | 5/2000 |
| JP | 2001078974 | 3/2001 |
| JP | 2002224053 | 8/2002 |
| JP | 2002263185 | 9/2002 |
| JP | 2002282218 | 10/2002 |
| JP | 2002282219 | 10/2002 |
| JP | 2002291684 | 10/2002 |
| JP | 2003210395 | 7/2003 |
| JP | 3454525 | 10/2003 |
| JP | 2003325440 | 11/2003 |
| JP | 2004007187 | 1/2004 |
| JP | 2004507188 | 3/2004 |
| JP | 2004134384 | 4/2004 |
| JP | 2004274452 | 9/2004 |
| JP | 2004313242 | 11/2004 |
| JP | 2004318534 | 11/2004 |
| JP | 2004364016 | 12/2004 |
| JP | 2005031840 | 2/2005 |
| JP | 2005073886 | 3/2005 |
| JP | 2005124708 | 5/2005 |
| JP | 2005148021 | 6/2005 |
| JP | 2005152037 | 6/2005 |
| JP | 2005287691 | 10/2005 |
| JP | 2005304880 | 11/2005 |
| JP | 2005532841 | 11/2005 |
| JP | 2005532849 | 11/2005 |
| JP | 2005343515 | 12/2005 |
| JP | 2006006377 | 1/2006 |
| JP | 2006509574 | 3/2006 |
| JP | 2006177699 | 7/2006 |
| JP | 2006187611 | 7/2006 |
| JP | 2006278091 | 10/2006 |
| JP | 2006346000 | 12/2006 |
| JP | 3876573 | 1/2007 |
| JP | 2007151809 | 6/2007 |
| JP | 2007159631 | 6/2007 |
| JP | 2007200739 | 8/2007 |
| JP | 2007313340 | 12/2007 |
| JP | 2007330677 | 12/2007 |
| JP | 2008011865 | 1/2008 |
| JP | 2008501415 | 1/2008 |
| JP | 2008176434 | 7/2008 |
| JP | 2008191955 | 8/2008 |
| JP | 2008289724 | 12/2008 |
| JP | 2009034345 | 2/2009 |
| JP | 2009050541 | 3/2009 |
| JP | 2009061236 | 3/2009 |
| JP | 2011519583 | 7/2011 |
| KR | 20020015907 | 3/2002 |
| KR | 20020061744 | 7/2002 |
| KR | 200600977523 | 7/2006 |
| KR | 100927471 | 11/2009 |
| KR | 20110137001 | 12/2011 |
| KR | 10-2012-099995 | 9/2012 |
| TW | 200301864 | 7/2003 |
| TW | 553735 | 9/2003 |
| TW | 200724094 | 7/2007 |
| TW | 200812556 | 3/2008 |
| TW | 201120673 | 6/2011 |
| WO | WO1988002237 | 4/1988 |
| WO | WO1992021307 | 12/1992 |
| WO | WO1993008734 | 5/1993 |
| WO | WO1993019667 | 10/1993 |
| WO | WO1994001165 | 1/1994 |
| WO | WO9516393 | 6/1995 |
| WO | WO1997014112 | 4/1997 |
| WO | WO1997039963 | 10/1997 |

(56) References Cited

FOREIGN PATENT DOCUMENTS

| | | |
|---|---|---|
| WO | WO1998043537 | 10/1998 |
| WO | WO1999037290 | 7/1999 |
| WO | WO1999059465 | 11/1999 |
| WO | WO2000033246 | 6/2000 |
| WO | WO2001000085 | 1/2001 |
| WO | WO2001047466 | 7/2001 |
| WO | WO2001049364 | 7/2001 |
| WO | WO2001074011 | 10/2001 |
| WO | WO2001080731 | 11/2001 |
| WO | WO200235997 | 5/2002 |
| WO | WO2002045489 | 6/2002 |
| WO | WO2002058330 | 7/2002 |
| WO | WO2002062276 | 8/2002 |
| WO | WO2002087681 | 11/2002 |
| WO | WO2002095351 | 11/2002 |
| WO | WO2003005877 | 1/2003 |
| WO | WO2003050643 | 6/2003 |
| WO | WO2003068061 | 8/2003 |
| WO | WO2004014225 | 2/2004 |
| WO | WO2004019172 | 3/2004 |
| WO | WO2004039256 | 5/2004 |
| WO | WO2004059551 | 7/2004 |
| WO | WO2004066833 | 8/2004 |
| WO | WO2004066834 | 8/2004 |
| WO | WO2004066903 | 8/2004 |
| WO | WO2004068748 | 8/2004 |
| WO | WO2004068881 | 8/2004 |
| WO | WO2004075751 | 9/2004 |
| WO | WO2004109316 | 12/2004 |
| WO | WO2004110555 | 12/2004 |
| WO | WO2005011237 | 2/2005 |
| WO | WO2005020023 | 3/2005 |
| WO | WO2005024687 | 3/2005 |
| WO | WO2005041767 | 5/2005 |
| WO | WO2005047837 | 5/2005 |
| WO | WO2005051166 | 6/2005 |
| WO | WO2005053517 | 6/2005 |
| WO | WO2005069887 | 8/2005 |
| WO | WO2005082436 | 9/2005 |
| WO | WO2005083621 | 9/2005 |
| WO | WO2005110238 | 11/2005 |
| WO | WO2005117697 | 12/2005 |
| WO | WO2006009404 | 1/2006 |
| WO | WO2006016370 | 2/2006 |
| WO | WO2006021932 | 3/2006 |
| WO | WO2006027586 | 3/2006 |
| WO | WO2006028347 | 3/2006 |
| WO | WO2006035351 | 4/2006 |
| WO | WO2006037802 | 4/2006 |
| WO | WO2006046648 | 5/2006 |
| WO | WO2006055892 | 5/2006 |
| WO | WO2006055956 | 5/2006 |
| WO | WO2006059338 | 6/2006 |
| WO | WO2006075016 | 7/2006 |
| WO | WO2006100620 | 9/2006 |
| WO | WO2006104843 | 10/2006 |
| WO | WO2006109072 | 10/2006 |
| WO | WO2006116718 | 11/2006 |
| WO | WO2006119345 | 11/2006 |
| WO | WO2006123346 | 11/2006 |
| WO | WO2006127355 | 11/2006 |
| WO | WO2007001724 | 1/2007 |
| WO | WO2007001742 | 1/2007 |
| WO | WO2007013952 | 2/2007 |
| WO | WO2007014084 | 2/2007 |
| WO | WO2007014527 | 2/2007 |
| WO | WO2007021496 | 2/2007 |
| WO | WO2007027660 | 3/2007 |
| WO | WO2007028035 | 3/2007 |
| WO | WO2007036687 | 4/2007 |
| WO | WO2007036741 | 4/2007 |
| WO | WO2007036746 | 4/2007 |
| WO | WO2007040878 | 4/2007 |
| WO | WO2007067054 | 6/2007 |
| WO | WO2007071180 | 6/2007 |
| WO | WO2007096810 | 8/2007 |
| WO | WO2007101141 | 9/2007 |
| WO | WO2007115087 | 10/2007 |
| WO | WO2007120946 | 10/2007 |
| WO | WO2007123923 | 11/2007 |
| WO | WO2007127316 | 11/2007 |
| WO | WO2007127879 | 11/2007 |
| WO | WO2007127945 | 11/2007 |
| WO | WO2007128165 | 11/2007 |
| WO | WO2007130491 | 11/2007 |
| WO | WO2007133526 | 11/2007 |
| WO | WO2007143535 | 12/2007 |
| WO | WO2007149546 | 12/2007 |
| WO | WO2008008281 | 1/2008 |
| WO | WO2008012700 | 1/2008 |
| WO | WO2008030482 | 3/2008 |
| WO | WO2008039030 | 4/2008 |
| WO | WO2008052136 | 5/2008 |
| WO | WO2008061138 | 5/2008 |
| WO | WO2008063626 | 5/2008 |
| WO | WO2008066617 | 6/2008 |
| WO | WO2008076464 | 6/2008 |
| WO | WO2008085131 | 7/2008 |
| WO | WO2008089232 | 7/2008 |
| WO | WO2008091683 | 7/2008 |
| WO | WO2008095183 | 8/2008 |
| WO | WO2008097652 | 8/2008 |
| WO | WO2008101107 | 8/2008 |
| WO | WO2008112577 | 9/2008 |
| WO | WO2008112578 | 9/2008 |
| WO | WO2008120156 | 10/2008 |
| WO | WO2008133394 | 11/2008 |
| WO | WO2008134185 | 11/2008 |
| WO | WO2008150633 | 12/2008 |
| WO | WO2009001108 | 12/2008 |
| WO | WO2009005759 | 1/2009 |
| WO | WO2009006615 | 1/2009 |
| WO | WO2009022343 | 2/2009 |
| WO | WO2009029453 | 3/2009 |
| WO | WO2009032381 | 3/2009 |
| WO | WO2009036334 | 3/2009 |
| WO | WO2009051829 | 4/2009 |
| WO | WO2009051830 | 4/2009 |
| WO | WO2009063377 | 5/2009 |
| WO | WO2009081348 | 7/2009 |
| WO | WO2009111664 | 9/2009 |
| WO | WO2009146082 | 12/2009 |
| WO | WO2010009100 | 1/2010 |
| WO | WO2010011833 | 1/2010 |
| WO | WO2010019778 | 2/2010 |
| WO | WO2010057049 | 5/2010 |
| WO | WO2010075115 | 7/2010 |
| WO | WO2010080765 | 7/2010 |
| WO | WO2010080843 | 7/2010 |
| WO | WO2010107563 | 9/2010 |
| WO | WO2010107980 | 9/2010 |
| WO | WO2010115194 | 10/2010 |
| WO | WO2010132331 | 11/2010 |
| WO | WO2010135516 | 11/2010 |
| WO | WO2011024560 | 3/2011 |
| WO | WO2011068963 | 6/2011 |
| WO | WO2011133799 | 10/2011 |
| WO | WO2011159336 | 12/2011 |
| WO | WO2011159337 | 12/2011 |
| WO | WO2011159338 | 12/2011 |
| WO | WO2011159339 | 12/2011 |
| WO | WO2012104657 | 8/2012 |
| WO | WO2012158190 | 11/2012 |
| WO | WO2013012869 | 1/2013 |
| WO | WO2015112603 | 7/2015 |

OTHER PUBLICATIONS

Aronson, J., "Meyer's Side Effects of Cardiovascular Drugs," Elsevier, Mar. 2, 2009, Medical , 840 pages. (Not Attached).
Arshak et al., A Review and Adaptation of Methods of Object Tracking to Telemetry Capsules IC-Med; Jan. 2007 vol. 1, No. 1, Issue 1, 12pp.

(56) References Cited

OTHER PUBLICATIONS

"ASGE Technology Status Evaluation Report: wireless capsule endoscopy" American Soc. for Gastrointestinal Endoscopy; Apr. 2006 vol. 63, No. 4; 7 pp.
Au-Yeung, K., et al., "A Networked System for Self-Management of Drug Therapy and Wellness", Wireless Health '10, Oct. 5-7, 2010, San Diego, 9 pp.
Aydin et al., "Design and implementation considerations for an advanced wireless interface in miniaturized integrated sensor Microsystems" Sch. of Eng. & Electron., Edinburgh Univ., UK; Sep. 2003; Abstract Only (1 page).
Barrie, Heidelberg pH capsule gastric analysis. Texbook of Natural Medicine, (1992), Pizzorno, Murray & Barrie (4 pages).
Baskiyar, S. "A Real-time Fault Tolerant Intra-body Network" Dept. of Comp. Sci & Soft Eng; Auburn University; Proceedings of the 27th Annual IEEE Conference; 0742-1303/02 (2002) IEEE; 6 pp.
Bohidar et al., "Dielectric Behavior of Gelatin Solutions and Gels" Colloid Polym Sci (1998) 276:81-86.
Brock, "Smart Medicine: The Application of Auto-ID Technology to Healthcare" Auto-ID Labs (2002) http://www.autoidlabs.org/uploads/media/MIT-AUTOID-WH-010.pdf (14 pages).
Carlson et al., "Evaluation of a non-invasive respiratory monitoring system for sleeping subjects" Physiological Measurement (1999) 20(1): 53.
Chan, Adrian D.C., et al.,; "Wavelet Distance Measure for Person Identification Using Electrocardiograms," IEEE Transactions on Instrumentation and Measurement, IEEE Service Center, Piscataway, NJ, US, vol. 57, No. 2, Feb. 1, 2008, pp. 248-253.
Consolvo, Sunny et al., "Design Requirement for Technologies that Encourage Physical Activity," CHI 2006 Proceedings, Designing for Tangible Interactions, Apr. 22, 2006, Montreal, Quebec, Canada, pp. 457-466.
Coury, L. "Conductance Measurement Part 1: Theory"; Current Separations, 18:3 (1999) p. 91-96.
Delvaux et al., "Capsule endoscopy: Technique and indications" Clinical Gastoenterology; Oct. 2008 vol. 22, Issue 5, 1pp. (Abstract Only).
Description of ePatch Technology Platform for ECG and EMG, located it http://www.madebydelta.com/imported/images/DELTA_Web/documents/ME/ePatch_ECG_EMG.pdf, Dated Sep. 2, 2010 (1 page).
Dhar et al., "Electroless nickel plated contacts on porous silicon" Appl. Phys. Lett. 68 (10) pp. 1392-1393 (1996).
Eldek A., "Design of double dipole antenna with enhanced usable bandwidth for wideband phased array applications" Progress in Electromagnetics Research PIER 59, 1-15 (2006).
Evanczuk, S., "PIC MCU software library uses human body for secure communications link" ; EDN Network; edn.com; Retrieved from internet Jun. 19, 2013 at http://www.edn.com/electronics-products/other/4407842/PIC-MCU-software-library-uses-human-body-for-secure-communications-link; Feb. 26, 2013; 5 pages.
Fawaz et al., "Enhanced Telemetry System using CP-QPSK Band-Pass Modulation Technique Suitable for Smart Pill Medical Application" IFIP IEEE Dubai Conference Apr. 2008; http://www.asic.fh-offenburg.de/downloads/ePille/IFIP_IEEE_Dubai_Conference.pdf (5 pages).
Ferguson et al., "Dielectric Constant Studies III Aqueous Gelatin Solutions" J. Chem. Phys. 2, 94 (1934) p. 94-98.
Ferguson et al., "Wireless communication with implanted medical devices using the conductive properties of the body," Expert Rev Med Devices, Jul. 2011, 8(4): 427-433.
Furse C. M., "Dipole Antennas" J. Webster (ed). Wiley Encyclopedia of Electrical and Electronics Engineering (1999) p. 575-581.
Gaglani S. "Put Your Phone, or Skin, on Vibrate" MedGadget; Mar. 2012 http://medgadget.com/2012/03/put-your-phone-or-skin-on-vibrate.html 8pp.
Gilson, D.R. "Molecular dynamics simulation of dipole interactions", Department of Physics, Hull University, Dec. 2002, p. 1-43.
Given Imaging, "Agile Patency Brochure" (2006) http://www.inclino.no/documents/AgilePatencyBrochure_Global_GMB-0118-01.pdf; 4pp.
Gonzalez-Guillaumin et al., "Ingestible capsule for impedance and pH monitoring in the esophagus" IEEE Trans Biomed Eng; Dec. 2007 54(12) 1pp. (Abstract Only).
Greene, "Edible RFID microchip monitor can tell if you take your medicine" Bloomberg Businessweek; Mar. 2010 2 pp.; http://www.businessweek.com/idg/2010-03-31/edible-rfid-microchip-monitor-can-tell-if-you-take-your-medicine.html.
Greene, "Medicaid Efforts to Incentivize Healthy Behaviours", Center for Health Care Strategies, Inc., Resource Paper, Jul. 2007 (20 pages).
Halthion Medical Technologies "Providing Ambulatory Medical Devices Which Monitor, Measure and Record" webpage. Online website: http://www.halthion.com/; downloaded May 30, 2012; 2 pp.
Herbig, S.M., "Asymmetric-membrane tablet coatings for osmotic drug delivery", Journal of Controlled Release 35 (1995) 127-136.
Heydari et al., "Analysis of the PLL jitter due to power/ground and substrate noise"; IEEE Transactions on Circuits and Systems (2004) 51(12): 2404-16.
Hoeksma, J. "New 'smart pill' to track adherence" E-Health-Insider; http://www.e-health-insider.com/news/5910/new_'smart_pill'_monitors_medicines; May 17, 2010 (2010); 1pp.
Hoover et al., "Rx for health: Engineers design pill that signals it has been swallowed" University of Florida News; Mar. 2010 2pp.; http://news.ufl.edu/2010/03/31/antenna-pill-2/.
Hotz "The Really Smart Phone" The Wall Street Journal, What They Know (2011); 6 pp.; http://online.wsj.com/article/SB10001424052748704547604576263261679848814.html?mod=djemTECH_t.
Intromedic, MicroCam Innovative Capsule Endoscope Pamphlet. (2006) 8 pp. (http://www.intromedic.com/en/product/productinfo.asp).
ISFET—Ion Sensitive Field-Effect Transistor; Microsens S.A. pdf document. Office Action dated Jun. 13, 2011 for U.S. Appl. No. 12/238,345; 4pp.
Jimbo et al., "Gastric-fluid-utilized micro battery for micro medical devices" The Sixth International Workshop on Micro and Nano-technology for Power Geneartion and Energy Conservation Applications, (2006) pp. 97-100.
Jung, S. "Dissolvable 'Transient Electronics' Will Be Good for Your Body and the Environment" MedGadget; Oct. 1, 2012; Onlne website: http://medgadget.com/2012/10/dissolvable-transient-electronics-will-be-good-for-your-body-and-the-environment.html; downloaded Oct. 24, 2012; 4 pp.
Juvenile Diabetes Research Foundation International (JDRF), "Artificial Pancreas Project" Jun. 2010; http://www.artificialpancreasproject.com/; 3 pp.
Kamada K., "Electrophoretic deposition assisted by soluble anode" Materials Letters 57 (2003) 2348-2351.
Kendle, Earl R. and Morris, Larry A., "Preliminary Studies in the Development of a Gastric Battery for Fish" (1964). Nebraska Game and Parks Commission White Papers, Conference Presentations, & Manuscripts. Paper 22. p. 1-6.
Kim et al., "A Semi-Interpenetrating Network System for a Polymer Membrane"; Eur. Polym. J. vol. 33 No. 7; pp. 1009-1014 (1997).
Lee, K. B.; "Two-step activation of paper batteries for high power generation: design and fabrication of biofluid- and wateractivated paper batteries"; J. Micromech. Microeng. 16 (2006) 2312-2317.
Lee, K. B.; "Urine-activated paper batteries for Biosystems"; J. Micromech. Microeng. 15 (2005) S21 O-S214.
Li, P-Y, et al. "An electrochemical intraocular drug delivery device", Sensors and Actuators A 143 (2008) p. 41-48.
Lifescan, "OneTouch UltraLink™" http://www.lifescan.com/products/meters/ultralink; Jul. 2010 2 pp.
Lin et al., "Do Physiological Data Relate to Traditional Usability Indexes?" Proceedings of OZCHI 2005, Canberra, Australia (2005) 10 pp.
Mackay et al., "Radio Telemetering from within the Body" Inside Information is Revealed by Tiny Transmitters that can be Swallowed or Implanted in Man or Animal Science (1991) 1196-1202; 134; American Association for the Advancement of Science, Washington D.C.

(56) References Cited

OTHER PUBLICATIONS

Mackay et al., "Endoradiosonde" Nature, (1957) 1239-1240, 179 Nature Publishing Group.
Mandryk et al., "A physiological approach for continuously modeling user emotion in interactive play environments" Proceedings of Measuring Behavior (2008) (Maastrichtm The Netherlandsm Aug. 26-29) 2 pp.
Mandryk et al., "Objectively Evaluating Entertainment Technology" Simon Fraser University; CHI (2004) ACM 1-58113-703-6-04/0004; 2 pp.
McDermott-Wells, P., "What is Bluetooth?", IEEE Potentials, IEEE, New York, NY, vol. 23, No. 5, Dec. 1, 2004, pp. 33-35.
McKenzie et al., "Validation of a new telemetric core temperature monitor" J. Therm. Biol. (2004) 29(7-8):605-11 (4 pages).
Medtronic, "CareLink Therapy Management Software for Diabetes" Jul. 2010; https://carelink.minimed.com/patient/entry.jsp?bhcp=1; 1 pp.
Medtronic, "Carelink™ USB" (2008) http://www.medtronicdiabetes.com/pdf/carelink_usb_factsheet.pdf 2pp.
Medtronic "The New MiniMed Paradigm® REAL-Time Revel™ System" Aug. 2010 http://www.medtronicdiabetes.com/products/index.html; 2 pp.
Medtronic, "MINI MED Paradigm® Revel™ Insulin Pump" Jul. 2010 http://www.medtronicdiabetes.com/products/insulinpumps/index.html; 2 pp.
Medtronic, Mini Med Paradigm™ Veo™ System: Factsheet (2010). http://www.medtronic-diabetes.com.au/downloads/Paradigm%20Veo%20Factsheet.pdf ; 4 pp.
Melanson, "Walkers swallow RFID pills for science" Engadget; Jul. 2008; http://www.engadget.com/2008/07/29/walkers-swallow-rfid-pills-for-science/ (1 page).
Minimitter Co. Inc. "Actiheart" Traditional 510(k) Summary. Sep. 27, 2005 (8 pages).
Minimitter Co. Inc. Noninvasive technology to help your studies succeed. Mini Mitter.com Mar. 31, 2009 (4 pages).
Mini Mitter Co, Inc. 510(k) Premarket Notification Mini-Logger for Diagnostic Spirometer. 9-21 (1999) (9 pages).
Mini Mitter Co, Inc. 510(k) Premarket Notification for VitalSense. Apr. 22 (2004) (11 pages).
Minimitter Co. Inc. VitalSense Integrated Physiological Monitoring System. Product Description. Jul. 2005 (4 pages).
Minimitter Co. Inc. VitalSense Wireless Vital Signs Monitoring. Temperatures.com Mar. 31, 2009 (3 pages).
Mojaverian et al., "Estimation of gastric residence time of the Heidelberg capsule in humans: effect of varying food composition" Gastroenterology (1985) 89:(2): 392-7.
O'Brien et al., "The Production and Characterization of Chemically Reactive Porous Coatings of Zirconium via Unbalanced Magnetron Sputtering" Surface and Coatings Technology (1996) 86-87; 200-206.
Owano, N., "Study proposes smart sutures with sensors for wounds" phys.org. Aug. 2012. http://phys.org/news/2012-08-smart-sutures-sensors-wounds.html; 2pp.
"PALO Bluetooth Baseband" PALO Bluetooth Resource Center; Retrieved from internet Dec. 12, 2012 at URL:http://palowireless.com/bluearticles/baseband.asp; first cited in Office Action dated Jan. 17, 2013 for EP08853901.0 (2013); 6pp.
Park, "Medtronic to Buy MiniMed for $3.7 Billion" (2001) HomeCare; http://homecaremag.com/mag/medical_medtronic_buy_minimed/; 2 pp.
Platt, D., "Modulation and Deviation" AE6EO, Foothills Amateur Radio Society; Oct. 26, 2007; 61 pp.
Radio Antennae, http://www.erikdeman.de/html/sail018h.htm; (2008) 5 pages.
"RFID "pill" monitors marchers" RFID News; Jul. 2008 http://www.rfidnews.org/2008/07/23/rfid-pill-monitors-marchers/ (4 pages).
Rolison et al., "Electrically conductive oxide aerogels: new materials in electrochemistry" J. Mater. Chem. (2001) 1, 963-980.
Roulstone, et al., "Studies on Polymer Latex Films: I. A study of latex film morphology" Polymer International 24 (1991) pp. 87-94.

Sammoura, F. et al., "Water-activated disposable and long shelf life microbatteries", Sensors and Actuators A 111 (2004) 79-86.
Sanduleanu et al., "Octave tunable, highly linear, RC-ring oscillator with differential fine-coarse tuning, quadrature outputs and amplitude control for fiber optic transceivers" (2002) IEEE MTT-S International Microwave Symposium Digest 545-8.
Santini, J.T. et al, "Microchips as controlled drug delivery-devices", Agnew. Chem. Int. Ed. (2000), vol. 39, p. 2396-2407.
"SensiVida minimally invasive clinical systems" Investor Presentation Oct. 2009 28pp; http://www.sensividamedtech.com/SensiVidaGeneralOctober09.pdf, pp. 1-28.
Sharma, et al., "The Future is Wireless: Advances in Wireless Diagnostic and Therapeutic Technologies in Gastroenterology," Gastroenterology, Elsevier, Philadelphia, PA, vol. 137, No. 2, Aug. 1, 2009, pp. 434-439.
Shawgo, R.S. et al. "BioMEMS from drug delivery", Current Opinion in Solid State and Material Science 6; May 2002, p. 329-334.
Shin et al., "A Simple Route to Metal Nanodots and Nanoporous Metal Films"; Nano Letters, vol. 2, No. 9 (2002) pp. 933-936.
Shrivas et al., "A New Platform for Bioelectronics—Electronic Pill", Cummins College, (2010).; http://www.cumminscollege.org/downloads/electronics_and_telecommunication/Newsletters/Current%20Newsletters.pdf; First cited in third party client search conducted by Patent Eagle Search May 18, 2010 (2010), pp. 11-12.
"Smartlife awarded patent for knitted transducer" Innovation in Textiles News: http://www.innovationintextiles.com/articles/208.php; 2pp. Aug. 2009.
"The SmartPill Wireless Motility Capsule" Smartpill, The Measure of GI Health; May 2010 http://www.smartpillcorp.com/index.cfm?pagepath=Products/The_SmartPill_Capsule&id=17814, (1 page).
Solanas et al., "RFID Technology for the Health Care Sector" Recent Patents on Electrical Engineering (2008) 1, 22-31.
Soper, S.A. et al. "Bio-Mems Technologies and Applications", Chapter 12, "MEMS for Drug Delivery", p. 325-346 (2007).
Swedberg, "University Team Sees Ingestible RFID Tag as a Boon to Clinical Trials" RFID Journal Apr. 27, 2010; http://www.rfidjournal.com/article/view/7560/1, 3pp.
Tajalli et al., "Improving the power-delay performance in subthreshold source-coupled logic circuits" Integrated Circuit and System Design. Power and Timing Modeling, Optimization and Simulation, Springer Berlin Heidelberg (2008) 21-30.
Tatbul et al., "Confidence-based data management for personal area sensor networks" ACM International Conference Proceeding Series (2004) 72, (3 pages).
Tierney, M.J. et al "Electroreleasing Composite Membranes for Delivery of Insulin and other Biomacromolecules", J. Electrochem. Soc., vol. 137, No. 6, Jun. 1990, p. 2005-2006.
Trutag, Technologies, Inc., Spectral Microtags for Authentication and Anti-Counterfeiting; "Product Authentication and Brand Protection Solutions"; http://www.trutags.com/; downloaded Feb. 12, 2013 (2013); 1 pp.
VonStetten, F. et al., "Biofuel cells as power generation for implantable devices", Pore. Eurosensors XX, (2006), pp. 22-225.
Walkey, "MOSFET Structure and Processing"; 97.398* Physical Electronics Lecture 20 (24 pages), Office Action dated Jun. 13, 2011 for U.S. Appl. No. 12/238,345.
Watson, et al., "Determination of the relationship between the pH and conductivity of gastric juice" Physiol Meas. 17 (1996) pp. 21-27.
Winter, J. et al. "The material properties of gelatin gels"; USA Ballistic Research Laboratories, Mar. (1975), p. 1-157.
Wongmanerod et al., "Determination of pore size distribution and surface area of thin porous silicon layers by spectroscopic ellipsometry" Applied Surface Science 172 (2001) 117-125.
Xiaoming et al., "A telemedicine system for wireless home healthcare based on bluetooth and the internet" Telemedicine Journal and e-health (2004) 10(S2): S110-6.
Yang et al., "Fast-switching frequency synthesizer with a discriminator-aided phase detector" IEEE Journal of Solid-State Circuits (2000) 35(10): 1445-52.

(56) References Cited

OTHER PUBLICATIONS

Yao et al., "Low Power Digital Communication in Implantable Devices Using Volume Conduction of Biological Tissues" Proceedings of the 28th IEEE, EMBS Annual International Conference, Aug. 30-Sep. 3, 2006.
Zhang, Y-T. et al., "Wireless Biomedical Sensing," Wiley Encyclopedia of Biomedical Engineering, 2006, pp. 1-9.
Zimmerman, "Personal Area Networks: Near-field intrabody communication" IBM Systems Journal (1996) 35 (3-4):609-17.
Zworykin, "A Radio Pill" Nature, (1957) 898, 179 Nature Publishing Group (1 page).
Van der Biest, O., et al., "Electrophoretic deposition of materials," Annu. Rev. Mater. Sci. 1999, 29: pp. 327-352.

\* cited by examiner

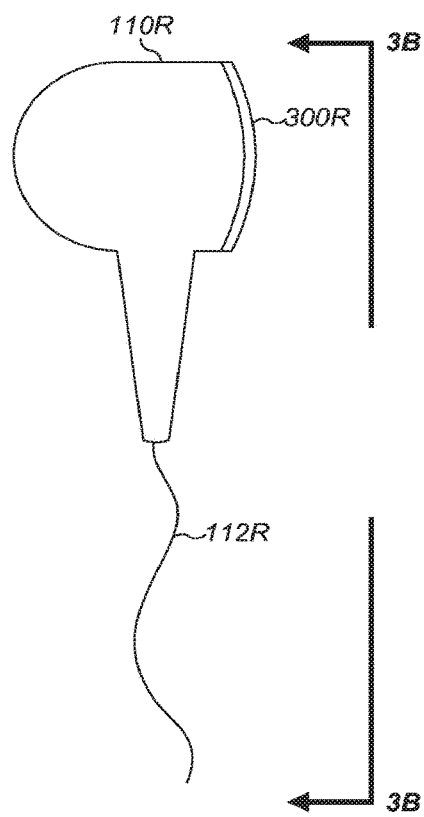
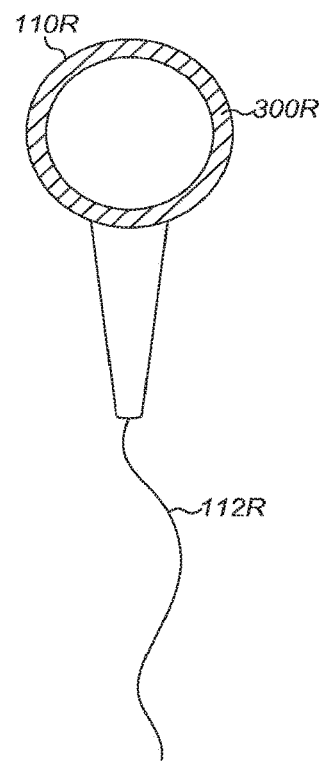
FIG. 3A
FIG. 3B

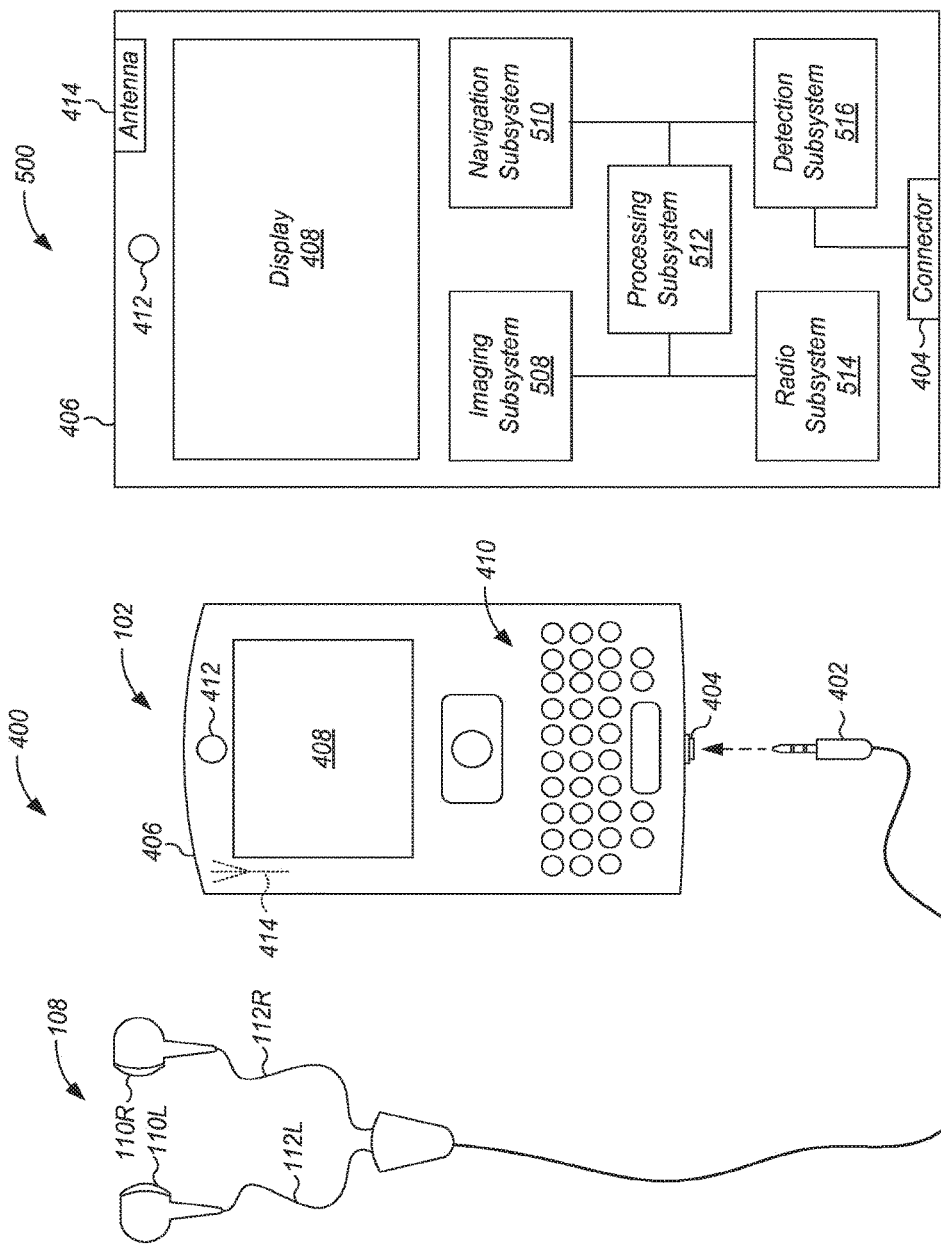

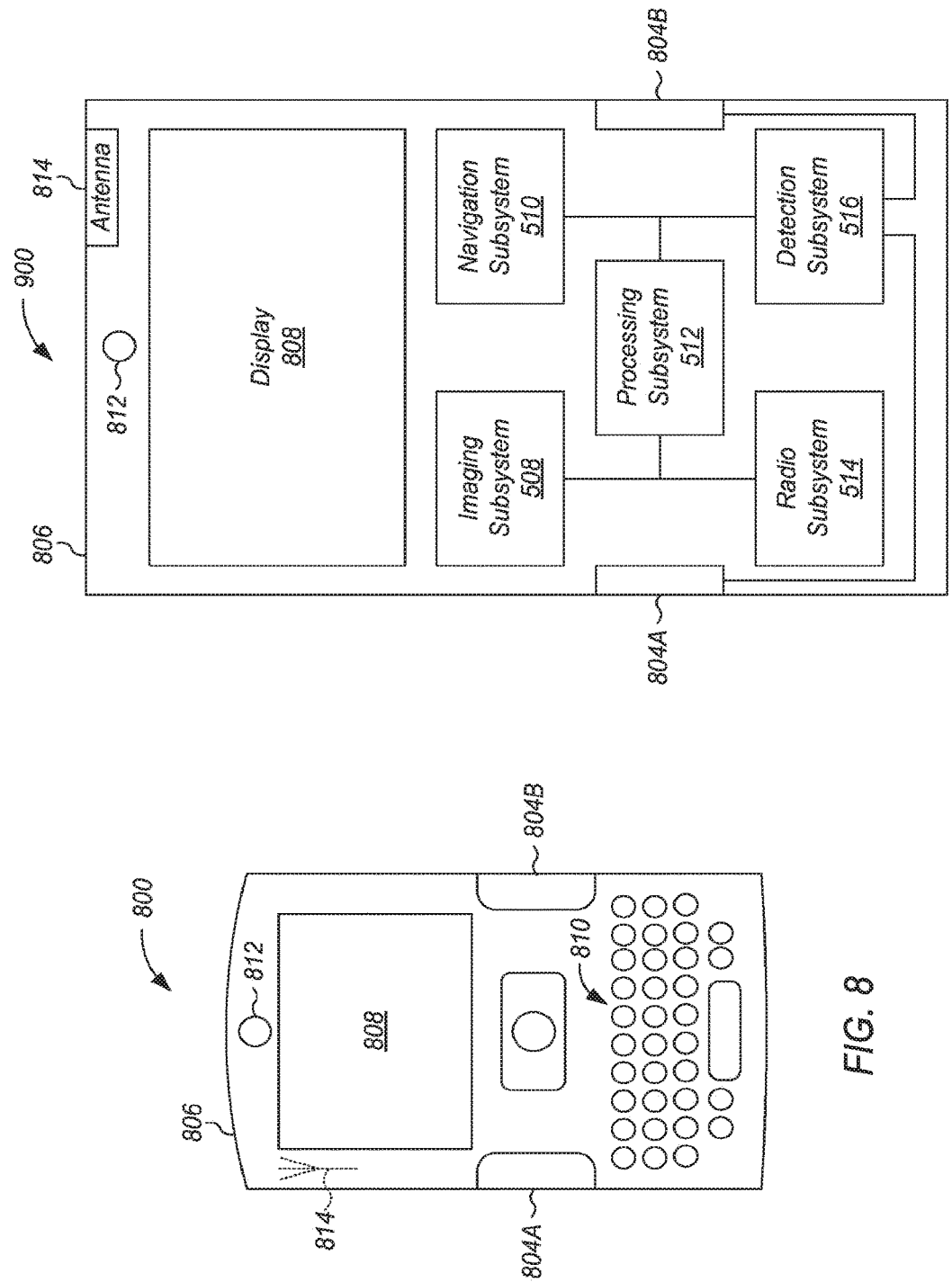

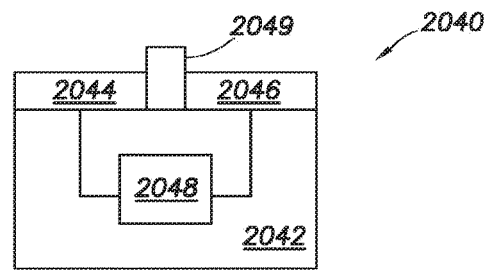
FIG.22
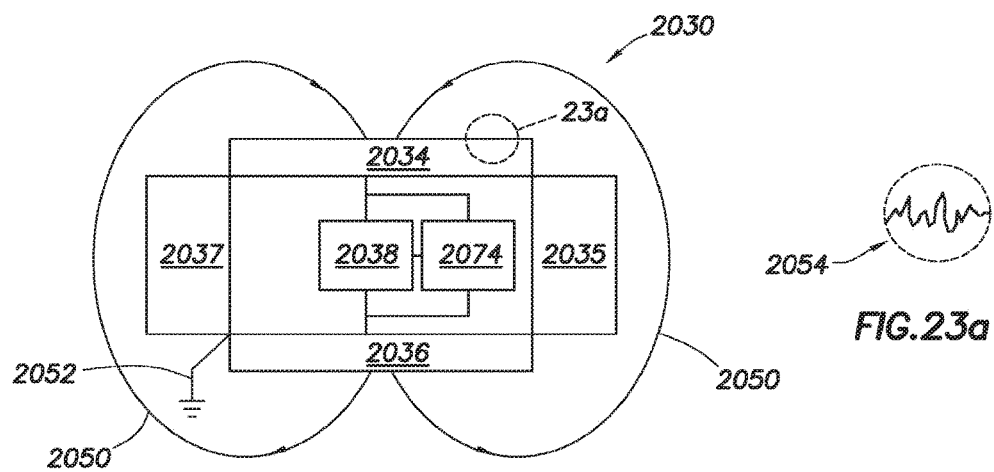
FIG.23a
FIG.23

MOBILE DEVICE AND SYSTEM FOR DETECTION AND COMMUNICATION OF INFORMATION RECEIVED FROM AN INGESTIBLE DEVICE

CROSS REFERENCE TO RELATED APPLICATIONS

This application is a continuation application claiming priority under 35 U.S.C. § 120 to U.S. patent application Ser. No. 14/234,069, titled MOBILE COMMUNICATION DEVICE, SYSTEM, AND METHOD, filed on Mar. 19, 2014, which was filed under 35 U.S.C. § 371 as a national stage application of International Application No. PCT/US2012/047076, titled MOBILE COMMUNICATION DEVICE, SYSTEM, AND METHOD, filed on Jul. 17, 2012, which claims the benefit under 35 U.S.C. § 119(e) of U.S. Provisional Patent Application No. 61/510,434, titled MOBILE COMMUNICATION DEVICE, SYSTEM AND METHOD, filed on Jul. 21, 2011, the entire disclosures of which are hereby incorporated by reference herein.

INTRODUCTION

The present disclosure is related generally to a mobile device apparatus, system, and method for detecting a communication from another device, e.g., an ingestible device, an implantable device, an ingestible event marker (IEM), an implantable pulse generator such as a pacemaker, for example, a stent, an ingestible or implantable transceiver, among other devices. In the case of an ingestible event marker (IEM), for example, currently, a wearable patch device is worn by the patient to detect the ingestion of a medicinal dose comprising an IEM embedded therein. The present disclosure is related to a mobile device such as a handheld portable device, computer, mobile telephone, sometimes referred to as a smartphone, tablet personal computer (PC), kiosk, desktop computer, or laptop computer, or any combination thereof, configured to detect the ingestion of an IEM by a patient.

Generally, detecting the ingestion of an IEM device by a patient is done by detection electronics provided in the form factor of a wearable patch applied to an outer surface of the skin. The patch may include wet or dry electrodes which are made to contact the skin. An adhesive layer affixes the entire patch arrangement to the patient. When the IEM device is ingested by the patient and comes into contact with stomach fluids, the IEM device initiates a communication with the detection circuitry of the patch to indicate that the particular IEM device was ingested by the patient.

To address various issues associated with wearing a patch to detect the ingestion of an IEM device, there is a need to eliminate the patch and communicate directly to a mobile device. The mobile device provides IEM communication in a discreet private manner without the need for the patient to wear a patch.

SUMMARY

In one aspect, a mobile device for detecting an electrical signal generated by an ingestible event marker is provided. The mobile device comprises a detection subsystem to receive an electrical signal generated by an ingestible event marker from a detection arrangement. A processing subsystem is coupled to the detection subsystem to decode the electrical signal. A radio subsystem is configured to transmit the decoded electrical signal to a wireless node.

FIGURES

FIG. 3A illustrates a side view of one aspect of a detection arrangement in the form of an earphone.

FIG. 3B illustrates a front view of one aspect of the detection arrangement shown in FIG. 3A.

FIG. 4 illustrates one aspect of a system comprising a detection arrangement in the form of earphones wiredly coupled to a mobile device for detecting an electrical signal generated by an ingestible event marker device.

FIG. 5 is a system diagram of one aspect of a mobile device for detecting an electrical signal generated by an ingestible event marker configured to couple to an external detection arrangement.

FIG. 8 illustrates one aspect of a mobile device comprising integrated electrodes for detecting an electrical signal generated by an ingestible event marker.

FIG. 9 is system diagram of one aspect of a mobile device for detecting an electrical signal generated by an ingestible event marker configured to couple to integrated electrodes.

FIG. 22 is a block diagram representation of another aspect of the event indicator system with dissimilar metals positioned on the same end and separated by a non-conducting material.

FIG. 23 shows ionic transfer or the current path through a conducting fluid when the event indicator system of FIG. 21 is in contact with conducting liquid and in an active state.

FIG. 23A shows an exploded view of the surface of dissimilar materials of FIG. 23.

Figure 29:
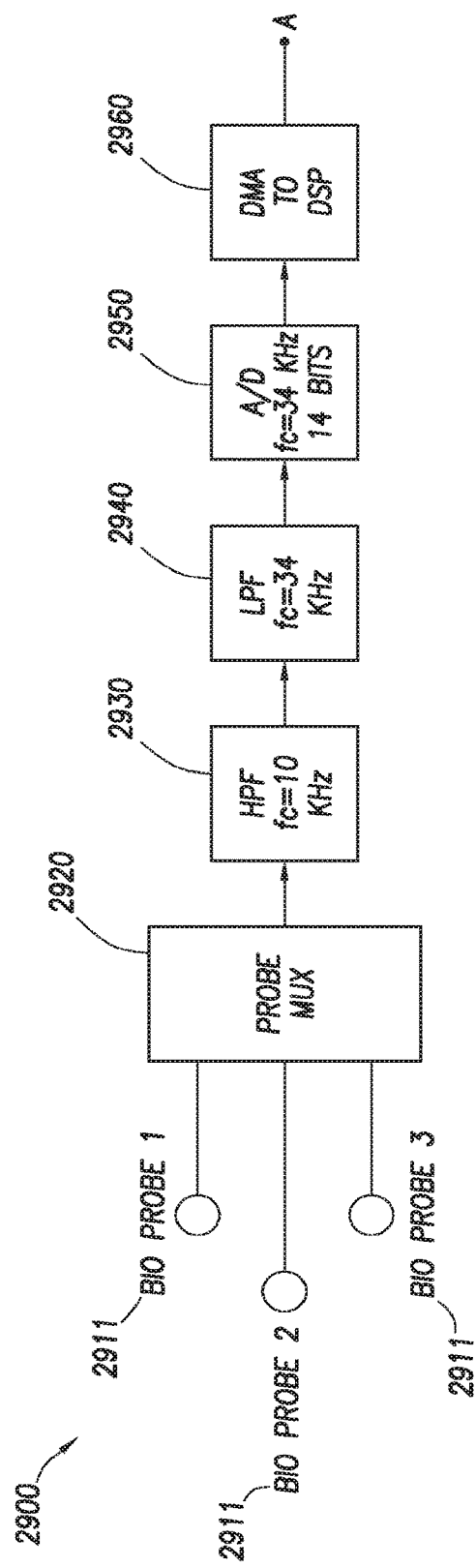

FIG. 29 provides a block diagram of a high frequency signal chain in a receiver, according to one aspect.

Figure 30:
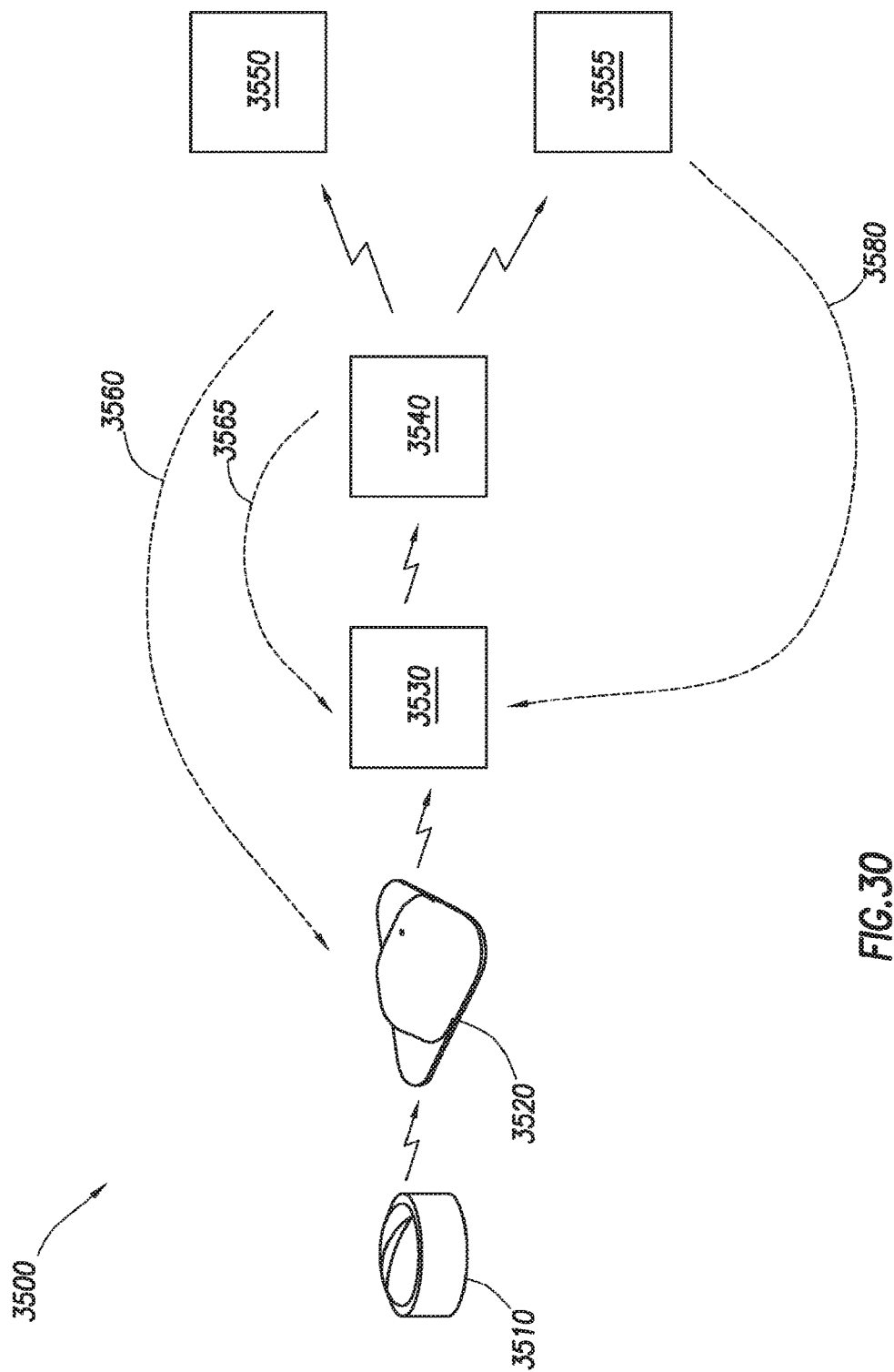

FIG. 30 provides a diagram of how a system that includes a signal receiver and an ingestible event marker may be employed, according to one aspect.

DESCRIPTION

In various aspects, the present disclosure is directed generally to an apparatus, system, and method employing a mobile device for detecting a communication from another device, e.g., an ingestible device, an implantable device, an ingestible event marker (IEM), an implantable pulse generator such as a pacemaker, for example, a stent, an ingestible or implantable transceiver, among other devices. In one aspect, the present disclosure provides a detection arrangement that may be wiredly and/or wirelessly coupled to a mobile device for detecting a communication from another device directly without employing a conventional detection patch (as described, for example, in Body-Associated Receiver and Method, filed Dec. 15, 2009, published as 2010-0312188 A1, the disclosure of which is herein incorporated by reference in its entirety. Examples of such receivers are shown in FIGS. 25-30, as discussed hereinafter.) In one aspect, a detection circuit module may be integrated with the mobile device. In one aspect, the detection circuit module may be integrated within a housing and/or cradle removably attachable to the mobile device. In one aspect, the detection circuit module may be integrated within a conventional device, which may be wiredly and/or wirelessly coupled to the mobile device. In one particular example, the detection circuit module is configured to detect and receive information encoded in an electrical current signature generated by an IEM device when it contacts a conducting fluid, and more particularly, when the IEM device is ingested by a patient and comes into contact with the digestive fluids in the stomach. Examples of such IEM devices are shown in FIGS. 21-24, as discussed hereinafter.

It will be appreciated that the term "mobile device" may refer generally to any device which can be configured as a communication node for receiving a first communication from a first device and transmitting a second communication to a second device. In one aspect, the mobile device may comprise various physical or logical elements implemented as hardware, software, or any combination thereof, as desired for a given set of design parameters or performance constraints. In various aspects, the physical or logical elements may be connected by one or more communications media. For example, communication media may comprise wired communication media, wireless communication media, or a combination of both, as desired for a given implementation.

In various aspects, the mobile device or elements of the mobile device such as the physical or logical elements of the device may be incorporated in any suitable device including, without limitation, a personal digital assistant (PDA), laptop computer, ultra-laptop computer, combination cellular telephone/PDA, mobile unit, subscriber station, user terminal, portable computer, handheld computer, palmtop computer, wearable computer, media player, messaging device, data communication device, tablet computer, e-book reader, cellular telephone, pager, one-way pager, two-way pager, messaging device, data communication device, computers that are arranged to be worn by a person, such as a wrist computer, finger computer, ring computer, eyeglass computer, belt-clip computer, arm-band computer, shoe computers, clothing computers, and other wearable computers, media or multimedia controllers (e.g., audio and/or visual remote control devices), intelligent devices/appliances such as consumer and home devices and appliances that are capable of receipt of data such as physiologic data and perform other data-related functions, e.g., transmit, display, store, and/or process data, refrigerators, weight scales, toilets, televisions, door frame activity monitors, bedside monitors, bed scales, mobile telephones, portable telephones, eyeglasses, hearing aids, headwear (e.g., hats, caps, visors, helmets, goggles, earmuffs, headbands), wristbands, jewelry, furniture, and/or any suitable object that may be configured to incorporate the appropriate physical and/or logical elements for implementing the mobile device and to receive a first communication from a first device and transmit a second communication to a second device.

It will be appreciated that the term "medication" or "medicinal dose" as used throughout this disclosure may include, without limitation, various forms of ingestible, inhalable, injectable, absorbable, or otherwise consumable medicaments and/or carriers therefor such as, for example, pills, capsules, gel caps, placebos, over capsulation carriers or vehicles, herbal, over-the-counter (OTC) substances, supplements, prescription-only medication, and the like, to be taken in conjunction with an IEM.

For clarity of disclosure, these and other aspects of the present disclosure will now be described in conjunction with the associated figures. Accordingly, turning now to FIG. 1, where one aspect of a system 100 comprising a mobile device 102 (e.g., a first node) for detecting an electrical signal generated by an ingestible event marker 104 (IEM device) is illustrated. As shown, a living body such as a patient 106 is wearing a detection arrangement 108 in the form of earphones 110 wiredly connected to the mobile device 102. In one aspect, the detection arrangement 108 comprises a right ear bud 110R and a left ear bud 110L wiredly coupled to the mobile device by respective electrical conducting cables 112R, 112L. As discussed in more detail below, the electrical conducting cables 112R, 112L are electrically coupled to a plug, which is configured to be received by a corresponding socket or jack connector of the mobile device 102.

When the patient 106 ingests an IEM device 104, the digestive fluids 114 in the stomach 116 activate the IEM device 104 to begin conducting a unique electrical current signature of various data, e.g., data identifying the IEM device 104, data identifying the medication, etc. Various aspects of an IEM device are disclosed in commonly assigned applications Pharma-Informatics System, PCT Application No. PCT/US2006/16370 published as WO/2006/116718; Controlled Activation Ingestible Identifier, PCT Application No. PCT/US2007/82563 published as WO/2008/052136; Active Signal Processing Personal Health Signal Receivers, PCT Application No. PCT/US2007/24225 published as WO/2008/63626; Low Voltage Oscillator for Medical Devices, PCT Application No. PCT/US2007/22257 published as WO/2008/066617; Ingestible Event Marker Systems, PCT Application No. PCT/US2008/52845 published as WO/2008/095183; In-Body Power Source Having High Surface Area Electrode, PCT Application No. PCT/US2008/53999 published as WO/2008/101107; In-Body Device Having a Multi-Directional Transmitter, PCT Application No. PCT/US2008/56296 published as WO/2008/112577; In-Body Device Having Deployable Antenna, PCT Application No. PCT/US2008/56299 published as WO/2008/112578; and In-Body Device with Virtual Dipole Signal Amplification, PCT Application No. PCT/US2008/77753 published as WO 2009/042812; the disclosures of which applications are herein incorporated by reference. Smart parenteral delivery systems are described in PCT application serial no. PCT/US2007/015547 published as WO 2008/008281; each of the foregoing disclosures is herein incorporated by reference in its entirety. The IEM device 104 conducts when in the process of being consumed by the digestive fluids 114 in the stomach 116. In various aspects, IEM devices 104 may be configured to communicate continuously or intermittently while being consumed. Additionally, the IEM device 104 may be wholly or partially consumed. In various aspects, for example, an IEM device 104 or components thereof may pass through a patient's system. In other aspects, an IEM device 104 may be configured to be selectively activated, deactivated, and/or reactivated. The architecture and operation of a typical IEM device 104 is explained in more detail below in connection with FIG. 21. The electrical current signature generated by the IEM device 104 while disintegrating in the digestive fluids 114 is detectable by the detection arrangement 108 coupled to the patient 106. Each of the ear buds 110R, 110L comprises a conducting electrode portion 300R as shown in FIGS. 3A, 3B for the right ear bud 110R.

Figure 1:
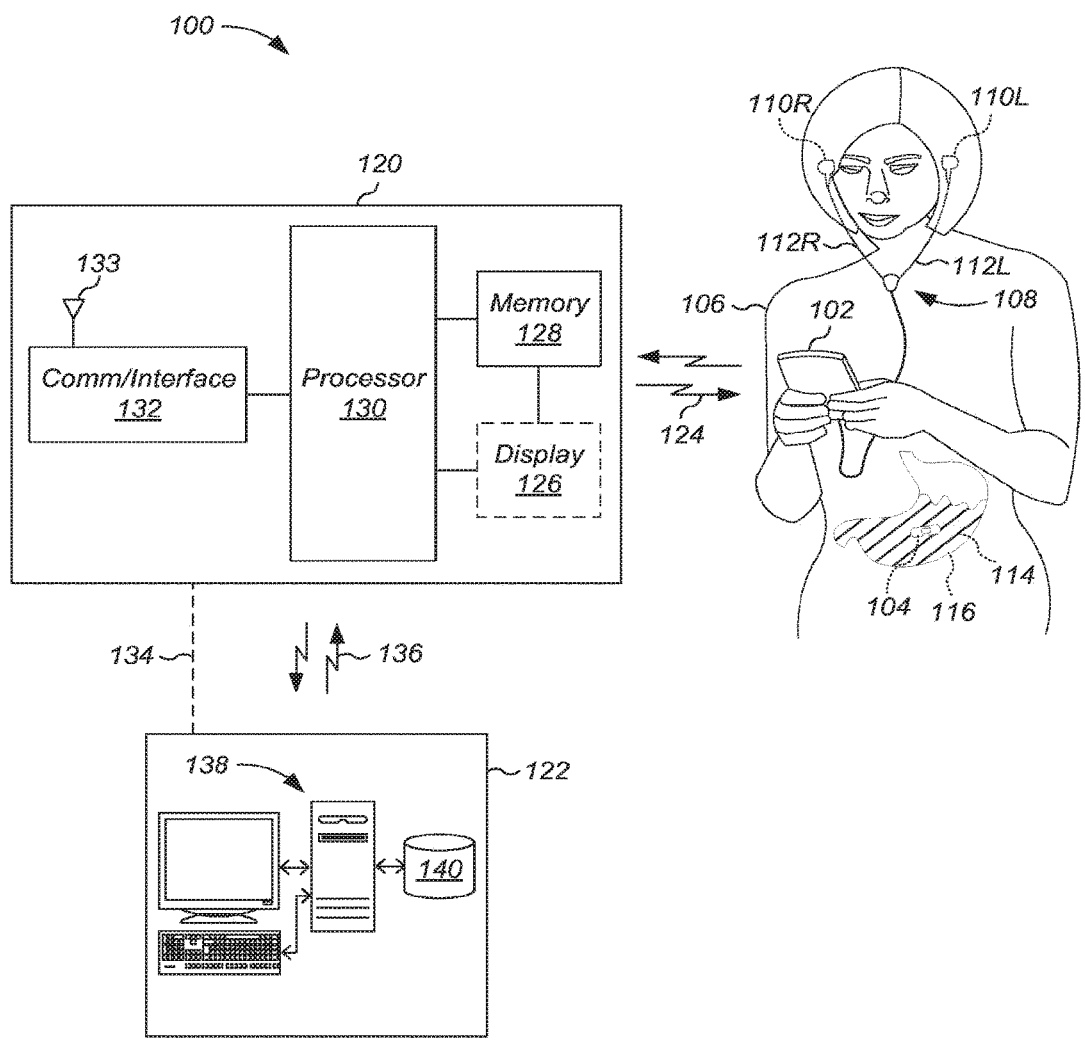
FIG. 1 illustrates one aspect of a system comprising a mobile device for detecting an electrical signal generated by an ingestible event marker device.

With reference now to FIGS. 1, 3A, and 3B, the conducting electrode portion 300R of the right ear bud 110R and 300L of the left ear bud 110L (not shown) are coupled to the skin of the patient 106 and detect the minute electrical current signature generated by the dissolving IEM device 104. The electrodes 300R, 300L electrically couple the IEM device 104 (FIGS. 1 and 2) signal to the detection circuitry in the mobile device 102. The detection arrangement 108 in the form of ear buds 110R, 110L may be used to support periodic detection of ingestion of an IEM device 104.

In use, the patient 106 inserts the ear buds 110R, 110L in corresponding ears and connects the plug into a corresponding connector located on the mobile device 102. The electrodes 300 contact the skin of the patient 106 to pick up the current signal generated by the IEM device 104. Once the detection arrangement is in place, an application is launched on the mobile device 102 and the patient 106 takes their medication, which includes the IEM device 104. The application may be launched automatically upon detection of the ear buds 110R, 110L, electrodes 300, and the like, or may be launched by the user selection using conventional techniques such as mouse over and click, pushbutton switch activation, virtual pushbutton switch activation, voice recognition, vibration, tapping user interface screen, orientation of the device, for example. When the IEM device 104 reaches the stomach 116, it begins to dissolve in the digestive fluids 114 and initiates communication of a unique electrical current signature, which is detected by the electrodes 300 located on the ear buds 110R, 110L. The signal is coupled to detection circuitry in the mobile device 102 and the ingestion of the IEM device 104 is confirmed or the application simply times out due to no detection. The patient 106 is then free to remove the ear buds 110R, 110L. In one aspect, the ear buds 110R, 110L may be used to pipe sound so that the patient 106 may be engaged by music, news feed, or other sounds while waiting for the IEM device 104 to be detected by the mobile device 102. In another aspect, an audible signal may alert the patient 106 to remove the ear buds 110R, 110L at the end of the process.

It will be appreciated that the form factor of the detection arrangement 108 is configured to look like a familiar object such that the patient 106 can readily interact with it and will not feel a stigma associated with wearing the detection arrangement 108. For example, the ear buds 110R, 110L will not lead to a stigma about requiring observed therapy because they blend into standard everyday electronics with which people are quite familiar and often use.

In one aspect, the patient 106 may be instructed to place the ear buds 110R, 110L on prior to taking the medicinal dose comprising the IEM device 104 to assure that the detection electrodes 300 are in place prior to the occurrence of the detectable event. It also minimizes opportunities for the patient 106 getting distracted after taking the medicinal dose and forgetting to attach the detection electrodes 300 associated with the ear buds 110R, 110L. It also minimizes anxiety that detection may be missed and rushing to locate the detector. The techniques described herein also free the patient's 106 hands for subsequent handling of the medicinal doses and for subsequent activity after taking the medicinal doses while waiting for the detection to take place.

With reference back to FIG. 1, the mobile device 102 acts as a first node for the detection of the unique current signature generated by the IEM 104. In response to detection of the unique current signature generated by the IEM device 104, the mobile device 102 may perform a number of functions. In one aspect, the mobile device 102 may store the time and date when the unique current signature was detected, which corresponds approximately to the time and date when the IEM device 104 was ingested by the patient 106. In addition, the mobile device 102 may store information encoded in the unique electrical current signature. For example, the identity of the IEM device 104, the type of medication associated with the IEM device 104, the manufacturer of the medication and/or IEM device 104, among other information, may be encoded by the unique electrical current signature, without limitation.

The mobile device 102 may transmit the detected information associated with the IEM device 104 to a wireless node 120 (e.g., a second node). The wireless node 120 may comprise, for example, a mobile station or fixed station having wireless capabilities. Examples for the wireless node 120 may include any of the examples given for the mobile device 102, and further may include a wireless access point, base station or node, base station radio/transceiver, router, switch, hub, gateway, and so forth. In one aspect, for example, the wireless node 120 may comprise a base station for a cellular radiotelephone communications system. Although some aspects may be described with the wireless node 120 implemented as a base station by way of example, it may be appreciated that other aspects may be implemented using other wireless devices as well. The wireless node 120 may be a communication hub, access point, another mobile device, and so on. Accordingly, the wireless node 120 may act as a local access point to wide area networks such as the Internet to communicate the information received from the IEM device 104 to a node 122, which is remotely located from the first and second nodes, e.g., the mobile device 102 and the wireless node 120, respectively. The remote node 122 may be a healthcare facility (physician's office, hospital, pharmacy), drug manufacturer, nutrition center, back end patient healthcare data processing facility, and the like.

In one aspect, the mobile device 102 communicates with the wireless node 120 over a wireless medium 124. In various aspects, the mobile device 102 and the wireless node 120 may comprise or be implemented by a wireless device. The wireless device generally may comprise various physical or logical elements implemented as hardware, software, or any combination thereof, as desired for a given set of design parameters or performance constraints. In various aspects, the physical or logical elements may be connected by one or more communications media. For example, communication media may comprise wired communication media, wireless communication media, or a combination of both, as desired for a given implementation.

In various implementations, the described aspects of the mobile device 102 and/or the wireless node 120 may comprise part of a cellular communication system. In one aspect, the mobile device 102 and the wireless node 120 may provide voice and/or data communications functionality in accordance with different types of cellular radiotelephone systems. Examples of cellular communication systems may include Code Division Multiple Access (CDMA) cellular radiotelephone communication systems, Global System for Mobile Communications (GSM) cellular radiotelephone systems, North American Digital Cellular (NADC) cellular radiotelephone systems, Time Division Multiple Access (TDMA) cellular radiotelephone systems, Extended-TDMA (E-TDMA) cellular radiotelephone systems, Narrowband Advanced Mobile Phone Service (NAMPS) cellular radiotelephone systems, third generation (3G) systems such as Wide-band CDMA (WCDMA), CDMA-2000, Universal Mobile Telephone System (UMTS) cellular radiotelephone systems compliant with the Third-Generation Partnership Project (3GPP), fourth generation systems (4G), and so forth.

In addition to voice communication services, the mobile device 102 and the wireless node 120 may be arranged to communicate using a number of different wireless wide area network (WWAN) data communication services. Examples of cellular data communication systems offering WWAN data communication services may include GSM with General Packet Radio Service (GPRS) systems (GSM/GPRS), CDMA/1×RTT systems, Enhanced Data Rates for Global Evolution (EDGE) systems, Evolution Data Only or Evolution Data Optimized (EV-DO) systems, Evolution For Data and Voice (EV-DV) systems, High Speed Downlink Packet Access (HSDPA) systems, and so forth.

In one aspect, the wireless node 120 may be connected by wired communications medium to additional nodes and connections to other networks, including a voice/data network such as the Public Switched Telephone Network (PSTN), a packet network such as the Internet, a local area network (LAN), a metropolitan area network (MAN), a wide area network (WAN), an enterprise network, a private network, and so forth. In one aspect, for example, network 130 may be arranged to communicate information in accordance with one or more Internet protocols as defined by the Internet Engineering Task Force (IETF), such as the Transmission Control Protocol/Internet Protocol (TCP/IP), for example. The network also may include other cellular radio telephone system infrastructure and equipment, such as base stations, mobile subscriber centers, central offices, and so forth.

In various aspects, the mobile device 102 and the wireless node 120 also may be capable of voice and/or data communications. Communications between the mobile device 102 and the wireless node 120 may be performed over wireless shared media 124 in accordance with a number of wireless protocols. Examples of wireless protocols may include various wireless local area network (WLAN) protocols, including the Institute of Electrical and Electronics Engineers (IEEE) 802.xx series of protocols, such as IEEE 802.11a/b/g/n, IEEE 802.16, IEEE 802.20, and so forth. Other examples of wireless protocols may include various WWAN protocols, such as GSM cellular radiotelephone system protocols with GPRS, CDMA cellular radiotelephone communication systems with 1×RTT, EDGE systems, EV-DO systems, EV-DV systems, HSDPA systems, and so forth. Further examples of wireless protocols may include wireless personal area network (PAN) protocols, such as an Infrared protocol, a protocol from the Bluetooth Special Interest Group (SIG) series of protocols, including Bluetooth Specification versions v1.0, v1.1, v1.2, v2.0, v2.0 with Enhanced Data Rate (EDR), as well as one or more Bluetooth Profiles, and so forth. In one aspect, the Bluetooth wireless technology uses short wavelength radio transmissions in the industrial, scientific, and medical (ISM) radio band from 2400-2480 MHz) from fixed and mobile devices, creating personal area networks (PANs) with high levels of security. Yet another example of wireless protocols may include near-field communication techniques and protocols, such as electro-magnetic induction (EMI) techniques. An example of EMI techniques may include passive or active radio-frequency identification (RFID) protocols and devices. Other suitable protocols may include Ultra Wide Band (UWB), Digital Office (DO), Digital Home, Trusted Platform Module (TPM), ZigBee, and other protocols.

In various aspects, the mobile device 102 may have one or more application client modules. In one aspect, an application client module receives information from the detection arrangement 108 and process the information to confirm that the patient 106 has ingested the IEM device 104. The application client module records a time and date that the IEM device 104 was detected, which corresponds approximately to the time and date when the IEM device 104 was ingested by the patient 106. In addition, client application module may store information encoded in the unique electrical current signature such as the identity of the IEM device 104, the type of medication associated with the IEM device 104, the manufacturer of the medication and/or IEM device 104, among other information. In some aspects, the client application module may implement a data logging function tracking the ingestible events associated with the patient 106. The client application module can initiate communication with other devices and/or networks.

Other client application modules may be arranged to retrieve and process information from a network (e.g., servers) and display the information on a display or audibly announce the information by way of speaker. The mobile device 102 may be implemented as an open platform adaptable to execute one or more application client programs and integrate with third party software application client programs. The application client modules may provide the necessary interface to existing data sources or backend services, such as web related and wireless services, support GPS navigation modules, process browser based content, and operate with one or more wireless mobile computing devices and web applications, for example. In one aspect, the application client modules may integrate with third party application client programs via APIs to retrieve location information, such as, for example, geographic coordinates, map interfaces, queries for search engines, interfaces to third party location based services (LBS), and any other services provided via servers, and the like. The application client modules may include a user interface layer to process search queries, search results, display maps (e.g., zoom/pan), provide turn-by-turn directions, provide voice activated turn-by-turn directions, and provide permission based interface for LBS type location information, among others. The application client modules also may include an interface layer to process local information, point of interface (POI) data, and a data abstraction layer to process map data, for example. The application client modules also may process data from various data sources or backend services distributed throughout a network (e.g., servers) such as, for example, GPS integrated circuits located either on or off the mobile device 500, carrier AGPS, various prolific search engines (e.g., GOOGLE, YAHOO, and the like), vector data, tile data, among others, for example. It will be appreciated by those skilled in the art that tile data may be defined as a spatial unit representing a sub-region of an image, usually of rectangular nature, by which geographic data is organized, subdivided, and stored in a map library.

In one aspect, for example, the mobile device 102 may employ a software architecture for retrieving and processing information from a communications network. The software architecture may enable the mobile device 102 to communicate and process information from the network and servers, for example. The software architecture includes component implementations and specifies standard programmatic interfaces such as APIs to assist in the common requirements of retrieving information wirelessly between an application client and multiple data source servers. As a result, the software architecture may provide a method to enable application clients to interact with disparate data providers.

In one aspect, for example, the software architecture may be implemented using object-oriented programming (OOP) techniques. OOP is a computer programming paradigm. OOP assumes that a computer program is composed of a collection of individual units, or objects, as opposed to a traditional assumption that a program is a list of instructions to the computer. Each object is capable of receiving messages, processing data, and sending messages to other objects. Almost any concept may be represented as an object. Examples of an object may include menu objects, image objects, frame objects, title objects, border objects, tab objects, list objects, color blue objects, button objects, scroll bar objects, input field objects, text and image objects, and so forth. Although the software architecture may be described in the context of OOP by way of example, it may be appreciated that other software paradigms may be used as desired for a given implementation. For example, the software architecture may be implemented using a model-view-controller (MVC) architecture as well. The aspects are not limited in this context.

As shown, the wireless node 120 may comprise an optional display 126. The display 126 may be implemented using any type of visual interface such as a liquid crystal display (LCD), capacitive touch screen panel, and the like.

As shown, the wireless node 120 may comprise a memory 128. In various aspects, the memory 128 may comprise any machine-readable or computer-readable media capable of storing data, including both volatile and non-volatile memory. For example, memory may include read-only memory (ROM), random-access memory (RAM), dynamic RAM (DRAM), Double-Data-Rate DRAM (DDR-RAM), synchronous DRAM (SDRAM), static RAM (SRAM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory (e.g., ovonic memory), ferroelectric memory, silicon-oxide-nitride-oxide-silicon (SONOS) memory, disk memory (e.g., floppy disk, hard drive, optical disk, magnetic disk), or card (e.g., magnetic card, optical card), or any other type of media suitable for storing information.

The wireless node 120 may comprise a processor 130 such as a central processing unit (CPU). In various aspects, the processor 130 may be implemented as a general purpose processor, a chip multiprocessor (CMP), a dedicated processor, an embedded processor, a digital signal processor (DSP), a network processor, a media processor, an input/output (I/O) processor, a media access control (MAC) processor, a radio baseband processor, a co-processor, a microprocessor such as a complex instruction set computer (CISC) microprocessor, a reduced instruction set computing (RISC) microprocessor, and/or a very long instruction word (VLIW) microprocessor, or other processing device. The processor 510 also may be implemented by a controller, a microcontroller, an application specific integrated circuit (ASIC), a field programmable gate array (FPGA), a programmable logic device (PLD), and so forth.

In various aspects, the processor 130 may be arranged to run an operating system (OS) and various mobile applications. Examples of an OS include, for example, operating systems generally known under the trade name of Microsoft Windows OS, and any other proprietary or open source OS. Examples of mobile applications include, for example, a telephone application, a camera (e.g., digital camera, video camera) application, a browser application, a multimedia player application, a gaming application, a messaging application (e.g., e-mail, short message, multimedia), a viewer application, and so forth.

In various aspects, the processor 130 may be arranged to receive information through a communications interface 132. The communications interface 132 may comprise any suitable hardware, software, or combination of hardware and software that is capable of coupling the wireless node 120 to one or more networks and/or devices. In one aspect, the wireless node 120 is in wireless communication with the mobile device 102 via the wireless medium 124. The wireless node 120 also may communicate with the remote node 122 via a wired communication medium 134 or a wireless communication medium 136. The communications interface 132 may be arranged to operate using any suitable technique for controlling information signals using a desired set of communications protocols, services or operating procedures. The communications interface 138 may include the appropriate physical connectors to connect with a corresponding communications medium, whether wired or wireless.

Vehicles of communication include a network. In various aspects, the network may comprise LANs as well as WANs including without limitation Internet, wired channels, wireless channels, communication devices including telephones, computers, wire, radio, optical or other electromagnetic channels, and combinations thereof, including other devices and/or components capable of/associated with communicating data. For example, the communication environments include in-body communications, various devices, various modes of communications such as wireless communications, wired communications, and combinations of the same.

Wireless communication modes include any mode of communication between points that utilizes, at least in part, wireless technology including various protocols and combinations of protocols associated with wireless transmission, data, and devices. The points include, for example, wireless devices such as wireless headsets, audio and multimedia devices and equipment, such as audio players and multimedia players, telephones, including mobile telephones and cordless telephones, and computers and computer-related devices and components, such as tablet computers, printers.

Wired communication modes include any mode of communication between points that utilizes wired technology including various protocols and combinations of protocols associated with wired transmission, data, and devices. The points include, for example, devices such as audio and multimedia devices and equipment, such as audio players and multimedia players, telephones, including mobile telephones and cordless telephones, and computers and computer-related devices and components, such as tablet computers, printers.

Accordingly, in various aspects, the communications interface 138 may comprise one or more interfaces such as, for example, a wireless communications interface, a wired communications interface, a network interface, a transmit interface, a receive interface, a media interface, a system interface, a component interface, a switching interface, a chip interface, a controller, and so forth. When implemented by a wireless device or within wireless system, for example, the local node 120 may include a wireless communication interface 132 comprising one or more antennas 133, transmitters, receivers, transceivers, amplifiers, filters, control logic, and so forth.

In various aspects, the wireless node 120 may comprise the functionality to wirelessly receive and/or wirelessly transmit data received from the mobile device 102 and transmit that data to other nodes, such as the external node 122 or other nearby nodes, for example. Further, in various aspects, the wireless node 120 may incorporate and/or be associated with, e.g., communicate with, various devices. Such devices may generate, receive, and/or communicate data, e.g., physiologic data. The devices include, for example, "intelligent" devices such as gaming devices, e.g., electronic slot machines, handheld electronic games, electronic components associated with games and recreational activities.

In addition to the standard voice function of a telephone, various aspects of mobile telephones may support many additional services and accessories such as short message service (SMS) for text messaging, email, packet switching for access to the Internet, java gaming, wireless, e.g., short range data/voice communications, infrared, camera with video recorder, and multimedia messaging system (MMS) for sending and receiving photos and video. Some aspects of mobile telephones connect to a cellular network of base stations (cell sites), which is, in turn, interconnected to the public switched telephone network (PSTN) or satellite communications in the case of satellite phones. Various aspects of mobile telephones can connect to the Internet, at least a portion of which can be navigated using the mobile telephones.

Some aspects may be implemented, for example, using a machine-readable medium or article which may store an instruction or a set of instructions that, if executed by a machine, may cause the machine to perform a method and/or operations in accordance with the aspects. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, and the like. The instructions may be implemented using any suitable high-level, low-level, object-oriented, visual, compiled and/or interpreted programming language, such as C, C++, Java, BASIC, Perl, Matlab, Pascal, Visual BASIC, arrangement language, machine code, and so forth.

In one aspect, the wireless node 120 may be configured as a communication hub and may include any hardware device, software, and/or communications component(s), as well as systems, subsystems, and combinations of the same which generally function to communicate information received from the mobile device 102 to the remote node 122. Communication of the information includes receiving, storing, manipulating, displaying, processing, and/or transmitting the data to the remote node 122 via wired or wireless media 134, 136.

In various aspects, the wireless node 120 also functions to communicate, e.g., receive and transmit, non-physiologic data. Example of non-physiologic data include gaming rules and data generated by a separate cardiac-related device such as an implanted pacemaker and communicated to the hub (local node 120) directly or indirectly, e.g., via the mobile device 102.

Broad categories of each of the mobile device 102 and/or the wireless node 120 include, for example, base stations, personal communication devices, handheld devices, mobile telephones, and mobile computing devices having wireless capabilities generally known as smartphones capable of executing computer applications, as well as voice communications and/or data communications. Examples of mobile computing devices include any type of wireless device, mobile station, or portable computing device with a self-contained power source, e.g., battery. Examples of smartphones include, for example, products generally known under the trade designations Palm, Blackberry, iPhone, Android, Windows Phone, among others. In various aspects, the mobile device 102 and/or the wireless node 120 may comprise, or be implemented as, a PDA, laptop computer, ultra-laptop computer, combination cellular telephone/PDA, mobile unit, subscriber station, user terminal, portable computer, handheld computer, palmtop computer, wearable computer, media player, messaging device, data communication device, tablet computer, e-book reader, cellular telephone, pager, one-way pager, two-way pager, messaging device, data communication device, and so forth. Examples of a mobile device 102 and/or wireless node 120 also may include computers that are arranged to be worn by a person, such as a wrist computer, finger computer, ring computer, eyeglass computer, belt-clip computer, arm-band computer, shoe computers, clothing computers, and other wearable computers. A fixed computing device, for example, may be implemented as a desk top computer, workstation, client/server computer, and so forth.

The mobile device 102 and/or wireless node 120 may comprise personal communication devices including, for example, devices having communication and computer functionality and typically intended for individual use, e.g., mobile computers, sometimes referred to as "handheld devices." Base stations comprise any device or appliance capable of receiving data such as physiologic data. Examples include computers, such as desktop computers and laptop computers, and intelligent devices/appliances. Intelligent devices/appliances include consumer and home devices and appliances that are capable of receipt of data such as physiologic data. Intelligent devices/appliances may also perform other data-related functions, e.g., transmit, display, store, and/or process data. Examples of intelligent devices/appliances include refrigerators, weight scales, toilets, televisions, door frame activity monitors, bedside monitors, bed scales. Such devices and appliances may include additional functionality such as sensing or monitoring various physiologic data, e.g., weight, heart rate. Mobile telephones include telephonic communication devices associated with various mobile technologies, e.g., cellular networks.

As shown in FIG. 1, the wireless node 120 is in communication with a remote node 122. The remote node 122 comprises a processing system 138 communicatively coupled to a database 140. Information associated with patients, including identity and medication types and doses, may be stored in the database 140. In one aspect, the processing system 138 receives information from the mobile device 102 via the wireless node 120 and accesses the information in the database 140 to provide information to the care provider through the wireless node 120 and/or the mobile device 102. The remote node 122 can communicate various information; for example, identification information such as a photo of the patient for identification, a photo of the IEM device 104 before it is ingested, the type of medication combined with the IEM device 104, as well as confirmation of the type and dose of medication that the patient ingested. The wireless node 120 can communicate with the remote node 122 using any mode and frequency of communication that is available at the site, such as wireless, G2, G3, G4, real-time, periodically based on predetermined time delays, as well as store and forward at later time.

Vehicles of communication between the wireless node 120 and the remote node 122 include a network. In various aspects, the network may comprise a LAN as well as a WAN including without limitation Internet, wired channels, wireless channels, communication devices including telephones, computers, wire, radio, optical or other electromagnetic channels, and combinations thereof, including other devices and/or components capable of/associated with communicating data. For example, the communication environments include in-body communications, various devices, various modes of communications such as wireless communications, wired communications, and combinations of the same.

The processing system 138 at the remote node 122 may comprise servers configured as desired, e.g., to provide for subject directed permissions. For example, the servers may be configured to allow a family caregiver to participate in the subject's therapeutic regimen, e.g., via an interface (such as a web interface) that allows the family caregiver to monitor alerts and trends generated by the server, and provide support back to the patient. The servers also may be configured to provide responses directly to the subject, e.g., in the form of subject alerts, subject incentives, which are relayed to the subject via the communication device. The servers also may interact with a health care professional, e.g., RN, physician, which can use data processing algorithms to obtain measures of health and compliance of the subject, e.g., wellness index summaries, alerts, cross-patient benchmarks, and provide informed clinical communication and support back to the patient. The servers also may interact with pharmacies, nutrition centers, and drug manufactures.

In one aspect, the remote node 122 may store information received from the mobile device 102 in the database 140. Such information may comprise the approximate time and date stamp when the IEM device 104 was ingested by the patient 106. In addition, an identification number such as a serial number, for example, associated with the IEM device 104, the individual patient identification, the source of the medication, and the expiration date or shelf life of the medication combined with the IEM device 104 may be stored in the database 140.

Figure 2:
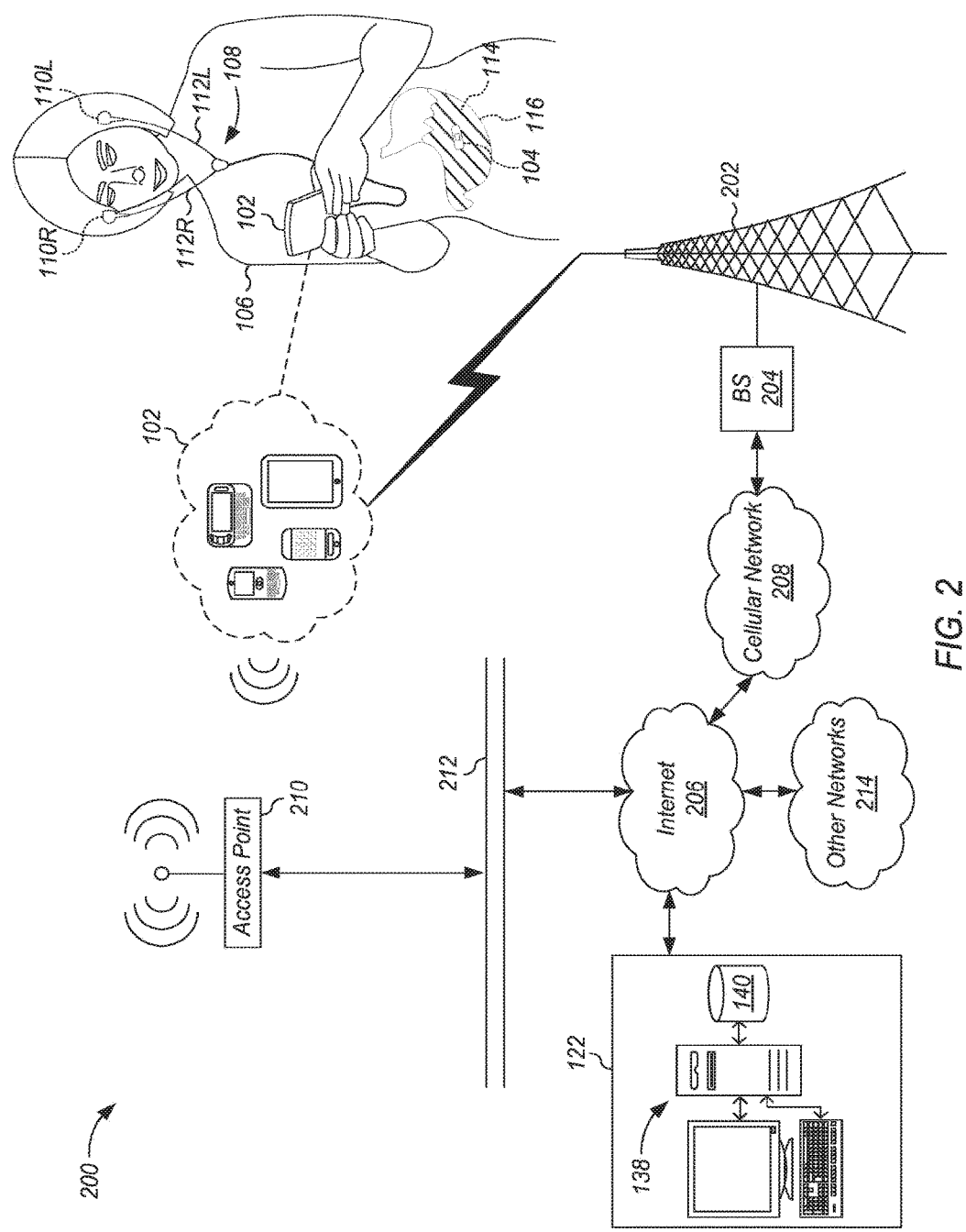
FIG. 2 illustrates one aspect of the system shown in FIG. 1 comprising a mobile device for detecting an electrical signal generated by an ingestible event marker device.

FIG. 2 illustrates one aspect of the system 200 comprising a mobile device 102 for detecting an electrical signal generated by an ingestible event marker, such as the IEM device 104 (FIG. 1), for example. In one aspect, shortly after the IEM device 104 is ingested by the patient 106, the IEM device 104 communicates information to the mobile device 102 via the detection arrangement 108 wiredly connected to the mobile device 102. The mobile device 102 communicates with a cellular tower 202 and base station 204 and can access the Internet 206 via a cellular network 208. Accordingly, information received by the mobile device 102 from the IEM device 104 can be communicated to the remote node 122 via the Internet 206 through the cellular network 208. The processing system 138 at the remote node 122 receives the information from the mobile device 102 and may store it in the database 140.

In another aspect, the mobile device 102 communicates with a local wireless access point 210 (e.g., Wi-Fi), which is coupled to a LAN 212. The LAN 212 is coupled to a WAN such as the Internet 206, which is coupled to the remotely located remote node 122. Upon detecting the unique electrical current signature generated by the IEM device 104, the mobile device 102 can communicate the information to the processing system 138 at the remote node 122 via the access point 210, LAN 212, and Internet 206. The processing system 134 stores the information in the database 140. The remote node 122 can access other networks 214 for additional processing of the information associated with the IEM device 104 stored in the database 140.

In another aspect, the mobile device 102 may transmit information associated with the IEM device 104 to another mobile device. The other mobile device then communicates with the cellular tower 202, base station 204, cellular network 208, and the Internet 206 to the remote node 122. In another aspect, the other mobile device communicates with the access point 210, LAN 212, and the Internet 206 to the remote node 122. Once communication is established with the remote node 122, the information associated with the IEM device 104 can be processed by the processing system and/or stored in the database 140.

FIG. 4 illustrates one aspect of a system 400 comprising a detection arrangement 108 in the form of earphones 110 wiredly coupled to a mobile device 102 for detecting an electrical signal generated by an ingestible event marker device. As shown in FIG. 4 the detection arrangement 108 comprises ear buds 110R, 110L coupled by electrical conductors 112R, 112L to a plug 402. The plug 402 is received in a corresponding data port socket or jack connector 404 portion of the mobile device 102. The mobile device 102 comprises a housing 406, a display 408, an input/output (I/O) system 410, an aperture 412 for capturing digital images, and an antenna 414. The functional modules of the mobile device 102 are described below in connection with FIG. 5.

The display 408 may comprise any suitable display unit for displaying information appropriate for a mobile device 102. The I/O system 410 may comprise any suitable I/O device for entering information into the mobile device 102. Examples for the I/O system 410 may include an alphanumeric keyboard, a numeric keypad, a touch pad, a capacitive touch screen panel, input keys, buttons, switches, rocker switches, voice recognition device and software, and so forth. The I/O system 410 may comprise a microphone and speaker, for example. Information also may be entered into the mobile device 102 by way of the microphone. Such information may be digitized by a voice recognition device.

FIG. 5 illustrates a system diagram of one aspect of a mobile device 500 for detecting an electrical signal generated by an ingestible event marker, such as the IEM device 104 (FIGS. 1 and 2), for example, configured to couple to an external detection arrangement. FIG. 5 illustrates a more detailed block diagram of the mobile computing device 102 described with reference to FIGS. 1, 2, 4. As shown in FIG. 5, for example, the mobile device 500 may comprise multiple elements. Although FIG. 5 shows a limited number of elements in a certain topology by way of example, it can be appreciated that additional or fewer elements in any suitable topology may be used in the mobile device 500 as desired for a given implementation. Furthermore, any element as described herein may be implemented using hardware, software, or a combination of both, as previously described with reference to node implementations. Aspects of the mobile device 500, however, are not limited in this context.

In various aspects, the mobile device 500 comprises a housing 406, an antenna 414, a radio subsystem 514, and a processing subsystem 512 connected to the radio subsystem 514 via a bus. The radio subsystem 514 may perform voice and data communications operations using wireless shared media for the mobile device 500. The processing subsystem 512 may execute software for the mobile device 500. A bus may comprise a universal serial bus (USB), micro-USB bus, dataport, and appropriate interfaces, as well as others. In one aspect the radio subsystem 514 may be arranged to communicate voice information and control information over one or more assigned frequency bands of the wireless shared media.

In one aspect, the mobile device 500 may comprise an imaging subsystem 508 for processing images captured through the aperture 412. A camera may be coupled (e.g., wired or wirelessly) to the processing subsystem 512 and is configured to output image data (photographic data of a person or thing, e.g., video data, digital still image data) to the processing subsystem 512 and to the display 408. In one aspect, the imaging subsystem 508 may comprise a digital camera implemented as an electronic device used to capture and store images electronically in a digital format. Additionally, in some aspects the digital camera may be capable of recording sound and/or video in addition to still images.

In one aspect, the imaging subsystem 508 may comprise a controller to provide control signals to components of a digital camera, including lens position component, microphone position component, and a flash control module, to provide functionality for the digital camera. In some aspects, the controller may be implemented as, for example, a host processor element of the processing subsystem 512 of the mobile device 500. Alternatively, the imaging controller may be implemented as a separate processor from the host processor.

In various aspects, the imaging subsystem 508 may comprise memory either as an element of the processing subsystem 512 of the mobile device 500 or as a separate element. It is worthy to note that in various aspects some portion or the entire memory may be included on the same integrated circuit as the controller. Alternatively, some portion or the entire memory may be disposed on an integrated circuit or other medium (e.g., hard disk drive) external to the integrated circuit of the controller.

In various aspects, the imaging subsystem 508 may comprise an aperture 412 with a lens component and a lens position component. The lens component may consist of a photographic or optical lens or arrangement of lenses made of a transparent material such as glass, plastic, acrylic or Plexiglass, for example. In one aspect, the one or more lens elements of the lens component may reproduce an image of an object and allow for zooming in or out on the object by mechanically changing the focal length of the lens elements. In various aspects, a digital zoom may be employed in the imaging subsystem 508 to zoom in or out on an image. In some aspects, the one or more lens elements may be used to focus on different portions of an image by varying the focal length of the lens elements. The desired focus can be obtained with an autofocus feature of the digital imaging subsystem 508 or by manually focusing on the desired portion of the image, for example.

A navigation subsystem 510 supports navigation using the mobile device 500. In various aspects the mobile device 500 may comprise location or position determination capabilities and may employ one or more location determination techniques including, for example, Global Positioning System (GPS) techniques, Cell Global Identity (CGI) techniques, CGI including timing advance (TA) techniques, Enhanced Forward Link Trilateration (EFLT) techniques, Time Difference of Arrival (TDOA) techniques, Angle of Arrival (AOA) techniques, Advanced Forward Link Trilateration (AFTL) techniques, Observed Time Difference of Arrival (OTDOA), Enhanced Observed Time Difference (EOTD) techniques, Assisted GPS (AGPS) techniques, hybrid techniques (e.g., GPS/CGI, AGPS/CGI, GPS/AFTL or AGPS/AFTL for CDMA networks, GPS/EOTD or AGPS/EOTD for GSM/GPRS networks, GPS/OTDOA or AGPS/OTDOA for UMTS networks), among others.

In one aspect, the mobile device 500 may be configured to operate in one or more location determination modes including, for example, a standalone mode, a mobile station (MS) assisted mode, and/or a MS-based mode. In a standalone mode, such as a standalone GPS mode, the mobile device 500 may be configured to determine its position without receiving wireless navigation data from the network, though it may receive certain types of position assist data, such as almanac, ephemeris, and coarse data. In a standalone mode, the mobile device 500 may comprise a local location determination circuit such as a GPS receiver which may be integrated within the housing 406 configured to receive satellite data via the antenna 414 and to calculate a position fix. Local location determination circuit may alternatively comprise a GPS receiver in a second housing separate from the housing 406 but in the vicinity of the mobile device 500 and configured to communicate with the mobile device 500 wirelessly (e.g., via a PAN, such as Bluetooth). When operating in an MS-assisted mode or an MS-based mode, however, the mobile device 500 may be configured to communicate over a radio access network (e.g., UMTS radio access network) with a remote computer (e.g., a location determination entity (LDE), a location proxy server (LPS) and/or a mobile positioning center (MPC), among others).

A detection subsystem 516 is coupled to a connector 404, which is configured to receive the plug 402 (FIG. 4) portion of the detection arrangement 108. The detection subsystem 516 detects the unique current signature generated by the IEM device 104 (FIGS. 1, 2), which encodes the information associated with the IEM device, the medication, and/or the patient, among other information. The detection subsystem 516 is coupled to the processing subsystem 512 and provides the decoded information to the processing subsystem 512. The processing subsystem 512 activates the radio subsystem 514 to communicate the decoded IEM information to the wireless node 120 (FIGS. 1, 2) and/or the cellular network 208 (FIG. 2). The detection subsystem 516 is described in more detail below in connection with FIGS. 6 and 7.

In various aspects, the mobile device 500 also may comprise a power management subsystem (not shown) to manage power for the mobile device 500, including the radio subsystem 514, the processing subsystem 512, and other elements of the mobile device 500. For example, the power management subsystem may include one or more batteries to provide direct current (DC) power, and one or more alternating current (AC) interfaces to draw power from a standard AC main power supply.

In various aspects, the radio subsystem 514 may include an antenna 414. The antenna 414 may broadcast and receive RF energy over the wireless shared media 124 (FIG. 1). Examples for the antenna 414 may include an internal antenna, an omni-directional antenna, a monopole antenna, a dipole antenna, an end fed antenna, a circularly polarized antenna, a micro-strip antenna, a diversity antenna, a dual antenna, an antenna array, a helical antenna, and so forth. The aspects are not limited in this context.

In various aspects, the antenna 414 may be connected to a multiplexer. The multiplexer multiplexes signals from a power amplifier for delivery to the antenna 414. The multiplexer demultiplexes signals received from the antenna for delivery to an RF chipset.

In various aspects, the multiplexer may be connected to a power amplifier, where the power amplifier may be used to amplify any signals to be transmitted over the wireless shared media 124 (FIG. 1). The power amplifier may work in all assigned frequency bands, such as four (4) frequency bands in a quad-band system. The power amplifier also may operate in various modulation modes, such as Gaussian Minimum Shift Keying (GMSK) modulation suitable for GSM systems and 8-ary Phase Shift Keying (8-PSK) modulation suitable for EDGE systems.

In various aspects, the power amplifier may be connected to an RF chipset. The RF chipset also may be connected to the multiplexer. In one aspect, the RF chipset may comprise an RF driver and an RF transceiver. The RF chipset performs all of the modulation and direct conversion operations required for GMSK and 8-PSK signal types for quad-band E-GPRS radio. The RF chipset receives analog in-phase (I) and quadrature (Q) signals from a baseband processor, and converts the I/O signals to an RF signal suitable for amplification by the power amplifier. Similarly, the RF chipset converts the signals received from the wireless shared media 124 (FIG. 1) via the antenna 414 and the multiplexer to analog I/O signals to be sent to the baseband processor. Although the RF chipset may use two chips by way of example, it may be appreciated that the RF chipset may be implemented using more or less chips and still fall within the intended scope of the aspects.

In various aspects, the RF chipset may be connected to the baseband processor, where the baseband processor may perform baseband operations for the radio subsystem 514. The baseband processor may comprise both analog and digital baseband sections. The analog baseband section includes I/O filters, analog-to-digital converters, digital-to-analog converters, audio circuits, and other circuits. The digital baseband section may include one or more encoders, decoders, equalizers/demodulators, GMSK modulators, GPRS ciphers, transceiver controls, automatic frequency control (AFC), automatic gain control (AGC), power amplifier (PA) ramp control, and other circuits.

In various aspects, the baseband processor also may be connected to one or more memory units via a memory bus. In one aspect, for example, the baseband processor may be connected to a flash memory unit and a secure digital (SD) memory unit. The memory units may be removable or non-removable memory. In one aspect, for example, the baseband processor may use approximately 1.6 megabytes of static read-only memory (SRAM) for E-GPRS and other protocol stack needs.

In various aspects, the baseband processor also may be connected to a subscriber identity module (SIM). The baseband processor may have a SIM interface for the SIM, where the SIM may comprise a smart card that encrypts voice and data transmissions and stores data about the specific user so that the user can be identified and authenticated to the network supplying voice or data communications. The SIM also may store data such as personal phone settings specific to the user and phone numbers. The SIM can be removable or non-removable.

In various aspects, the baseband processor may further include various interfaces for communicating with a host processor of the processing subsystem 512. For example, the baseband processor may have one or more universal asynchronous receiver-transmitter (UART) interfaces, one or more control/status lines to the host processor, one or more control/data lines to the host processor, and one or more audio lines to communicate audio signals to an audio subsystem of processing subsystem 514. The aspects are not limited in this context.

In various aspects, the processing subsystem 514 may provide computing or processing operations for the mobile device 500 and/or for the detection subsystem 516. For example, the processing subsystem 514 may be arranged to execute various software programs for the mobile device 500 as well as several software programs for the detection subsystem 516. Although the processing subsystem 514 may be used to implement operations for the various aspects as software executed by a processor, it may be appreciated that the operations performed by the processing subsystem 514 also may be implemented using hardware circuits or structures, or a combination of hardware and software, as desired for a particular implementation.

In various aspects, the processing subsystem 512 may include a processor implemented using any processor or logic device, such as a complex instruction set computer (CISC) microprocessor, a reduced instruction set computing (RISC) microprocessor, a very long instruction word (VLIW) microprocessor, a processor implementing a combination of instruction sets, or other processor device. In one aspect, for example, a processor may be implemented as a general purpose processor, such as a processor made by Intel Corporation, Santa Clara, Calif. The processor also may be implemented as a dedicated processor, such as a controller, microcontroller, embedded processor, a digital signal processor (DSP), a network processor, a media processor, an input/output (I/O) processor, a media access control (MAC) processor, a radio baseband processor, a field programmable gate array (FPGA), a programmable logic device (PLD), and so forth.

In one aspect, the processing subsystem 514 may include a memory to connect to the processor. The memory may be implemented using any machine-readable or computer-readable media capable of storing data, including both volatile and non-volatile memory. For example, the memory may include ROM, RAM, DRAM, DDRAM, SDRAM, SRAM, PROM, EPROM, EEPROM, flash memory, polymer memory such as ferroelectric polymer memory, ovonic memory, phase change or ferroelectric memory, silicon-oxide-nitride-oxide-silicon (SONOS) memory, magnetic or optical cards, or any other type of media suitable for storing information. It is worthy to note that some portion or all of the memory may be included on the same integrated circuit as the processor thereby obviating the need for a memory bus. Alternatively some portion or all of the memory may be disposed on an integrated circuit or other medium, for example a hard disk drive, that is external to the integrated circuit of the processor, and the processor may access the memory via a memory bus, for example.

In various aspects, the memory may store one or more software components (e.g., application client modules). A software component may refer to one or more programs, or a portion of a program, used to implement a discrete set of operations. A collection of software components for a given device may be collectively referred to as a software architecture or application framework. A software architecture for the mobile device 500 is described in more detail below.

A software architecture suitable for use with the mobile device 500 may include a user interface (UI) module, an interface module, a data source or backend services module (data source), and a third party API module. An optional LBS module may comprise a user based permission module, a parser module (e.g., National Maritime Electronic Association or NMEA), a location information source module, and a position information source module. In some aspects, some software components may be omitted and others added. Further, operations for some programs may be separated into additional software components, or consolidated into fewer software components, as desired for a given implementation. The mobile device 500 software architecture may comprise several elements, components or modules, collectively referred to herein as a "module." A module may be implemented as a circuit, an integrated circuit, an application specific integrated circuit (ASIC), an integrated circuit array, a chipset comprising an integrated circuit or an integrated circuit array, a logic circuit, a memory, an element of an integrated circuit array or a chipset, a stacked integrated circuit array, a processor, a digital signal processor, a programmable logic device, code, firmware, software, and any combination thereof.

Figure 6A:
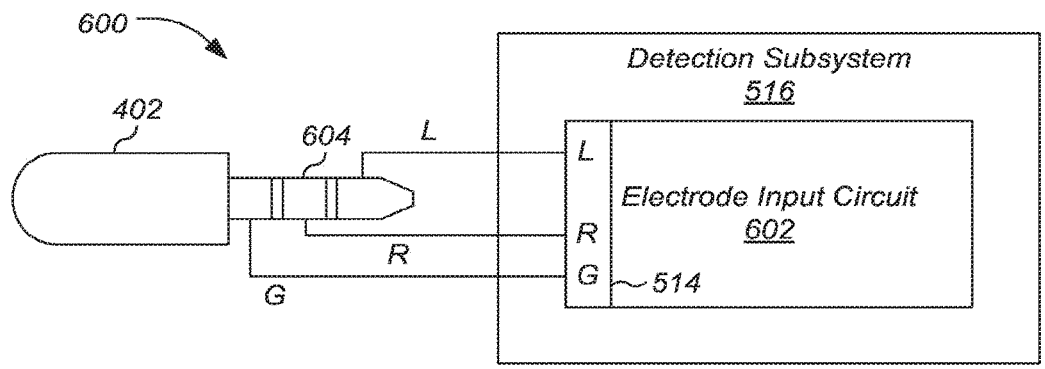
FIG. 6A is a diagram of one aspect of an earphone plug coupled to an electrode input circuit section of a detection subsystem of a mobile device for detecting an electrical signal generated by an ingestible event marker.

FIG. 6A is a diagram 600 of one aspect of an earphone plug 402 coupled to an electrode input circuit 602 portion of a detection subsystem 516 of the mobile device 500 for detecting an electrical signal generated by an ingestible event marker, such as the IEM device 104 (FIGS. 1 and 2), for example. The plug 402 comprises a conductive prong 604 having a plurality of conductive segments (L, R, G) separated by electrically insulative elements. Segment L is electrically connected to the left ear bud 110L (FIGS. 1, 2, 4) electrode element 300L (not shown), segment R is electrically connected to the right ear bud 110R (FIGS. 1, 2, 4) electrode element 300R (FIGS. 3A, 3B), and segment G is connected to ground. It will be appreciated that other configurations or additional segments may be included in a plug. For example, additional segments may be employed to pipe audio signals to the ear buds 110R, 110L in addition to the providing electrical connections to the electrode elements 300R, 300L. The plug 402 may be any type of electrical connector suitable for carrying electrical signals in either analog or digital form. The electrically conductive segments (L, R, G) are coupled to a corresponding connector 514 portion of the electrode input circuit 602.

Figure 6B:
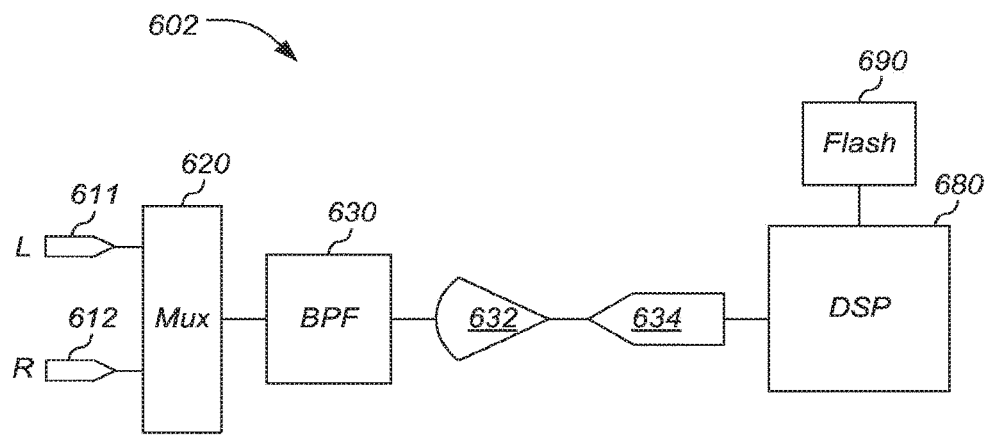
FIG. 6B is a diagram of one aspect of an electrode input circuit of the detection subsystem shown in FIG. 6A.

FIG. 6B is a diagram of one aspect of an electrode input circuit 602 of the detection subsystem 516 shown in FIG. 6A. FIG. 6B provides a more detailed block diagram of a circuit configured to implement the block functional diagram of the electrode input circuit 602 depicted in FIG. 6A, according to one aspect. In FIG. 6B, electrode input circuit 602 includes electrodes e1, e2 (611, 612) which, for example, receive the conductively transmitted signals by an IEM device via connections L and R from the plug 402. The signals received by the electrodes 611, 612 are multiplexed by a multiplexer 620 which is electrically coupled to the electrodes 611, 612.

The multiplexer 620 is electrically coupled to a high band pass filter 630. The signal chain provides for a programmable gain to cover the desired level or range. In this specific aspect, the high band pass filter 630 passes frequencies in the 10 KHz to 34 KHz band while filtering out noise from out-of-band frequencies. In other aspects, the high band pass filter 630 may be replaced with any suitable band pass filter for any suitable frequency. In the aspect illustrated in FIG. 6B, the high frequency band may vary, and may include, for example, a range of about 3 KHz to about 300 KHz. In other aspects, the frequency band may vary, and may include, for example, a range of about 0.3 KHz to about 30 KHz, for example. The passing frequencies are then amplified by an amplifier 632 before being converted into a digital signal by a converter 634 for input into a high power processor 680 (shown as a DSP), which is electrically coupled to the frequency signal chain. Also shown in FIG. 6B is a flash memory 690 electrically coupled to the high power processor 680 to enable memory storage and enhance efficiency of operations.

The high power processor 680 may be, for example, a VC5509 digital signal processor from Texas Instruments. The high power processor 680 performs the signal processing actions during the active state. These actions, may require larger amounts of current than the idle state—e.g., currents of 30 µA or more, such as 50 µA or more—and may include, for example, actions such as scanning for conductively transmitted signals, or processing conductively transmitted signals when received.

The detection subsystem 516 (FIG. 6A) may include a hardware accelerator module (not shown) to process data signals. The hardware accelerator module (not shown) may be implemented instead of, for example, a DSP. Being a more specialized computation unit, the hardware accelerator module performs aspects of the signal processing algorithm with fewer transistors (less cost and power) compared to the more general purpose DSP. The blocks of hardware may be used to "accelerate" the performance of important specific function(s). Some architectures for hardware accelerators may be "programmable" via microcode or VLIW assembly. In the course of use, their functions may be accessed by calls to function libraries.

Figure 7:
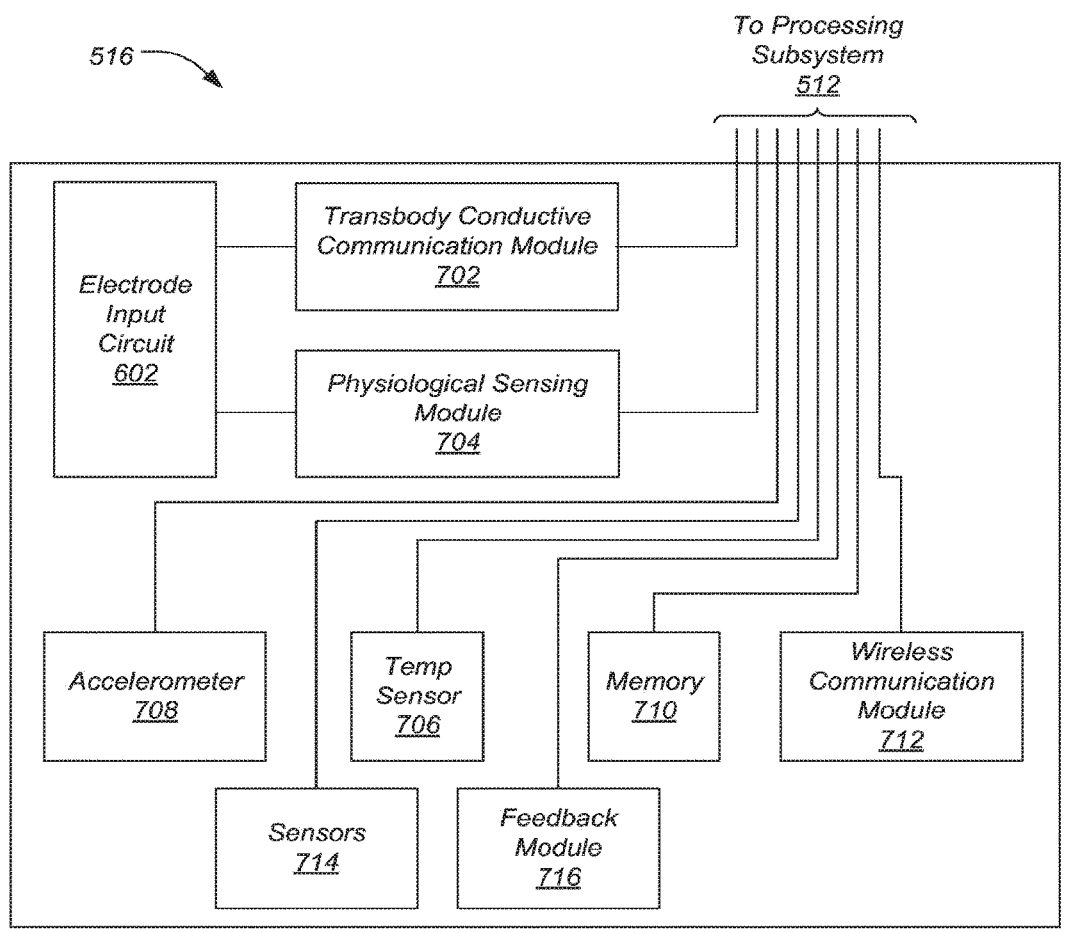
FIG. 7 is a system diagram of one aspect of a detection subsystem of a mobile device for detecting an electrical signal generated by an ingestible event marker.

FIG. 7 is a system diagram of one aspect of a detection subsystem 516 of a mobile device for detecting an electrical signal generated by an ingestible event marker, such as the IEM device 104 (FIGS. 1 and 2), for example. FIG. 7 is a block functional diagram of one aspect of an integrated circuit component. As shown in FIG. 7, the detection subsystem 516 comprises an electrode input circuit 602, which receives the electrical current signature generated by the IEM device 104 from the detection arrangement 108 (both shown in FIGS. 1 and 2). In one aspect, electrically coupled to the electrode input circuit 602 is a transbody conductive communication module 702 and, in another aspect, a physiological sensing module 704 optionally may be coupled to the electrode input circuit 602. In one aspect, the transbody conductive communication module 702 may be implemented as a first, e.g., high, frequency (HF) signal chain and the physiological sensing module 704 may be implemented as a second, e.g., low, frequency (LF) signal chain. In one aspect, the detection subsystem 516 also may include a temperature sensing module 706 for detecting ambient temperature and a 3-axis accelerometer 708. In one aspect, the temperature sensing module 706 may be implemented using complementary oxide semiconductor (CMOS) circuit elements. In various aspects, additional modules may be provided for sensing of the environment around the IEM device 104, for example, including, without limitation, Ph sensing, impedance sensing. The detection subsystem 516 also may comprise a memory 710 for data storage (similar to any of the previously discussed memory elements), and a wireless communication module 712 to receive data from and/or transmit data to another device, for example in a data download/upload action, respectively. In various aspects, the sensors 714 and the feedback modules 716 also may be included in the detection subsystem 516. In one aspect, as shown in FIG. 7, the various functional modules are coupled to the processing subsystem 512 of the mobile device 500 (FIG. 5). In other aspects, a detection subsystem may comprise its own dedicated processing engine. For example, as shown for example in FIG. 14, the detection subsystem 516 may comprise a dedicated processing engine 1402, for example, a microcontroller or a digital signal processor, that is separate from the processing subsystem 512 of the mobile device 500.

With reference back to FIG. 7, in various aspects, the transbody conductive communication module 702 and the wireless communication module 712 each may comprise one or more transmitters/receivers ("transceiver") modules. As used herein, the term "transceiver" may be used in a very general sense to include a transmitter, a receiver, or a combination of both, without limitation. In one aspect, the transbody conductive communication module 702 is configured to communicate with the IEM device 104 (FIGS. 1 and 2). In one aspect, the wireless communication module 712 may be configured to communicate with the wireless access point 210 (FIG. 2). In another aspect, the wireless communication module 712 may be configured to communicate with other mobile devices.

In various aspects, the sensors 714 typically contact the patient 106 (FIGS. 1 and 2), e.g., can be removably attached to the torso. In various other aspects, the sensors 714 may be removably or permanently attached to the detection subsystem 516. For example, the sensors 714 may be removably connected to the detection subsystem 516 by snapping metal studs. The sensors 714 may comprise, for example, various devices capable of sensing or receiving the physiologic data. The types of sensors 714 include, for example, electrodes such as biocompatible electrodes. The sensors 714 may be configured, for example, as a pressure sensor, a motion sensor, an accelerometer 708, an electromyography (EMG) sensor, an IEM device 104 (FIGS. 1 and 2), a biopotential sensor, an electrocardiogram sensor, a temperature sensor, a tactile event marker sensor, an impedance sensor, among other sensors.

In various aspects, the feedback module 716 may be implemented with software, hardware, circuitry, various devices, and combinations thereof. The function of the feedback module 716 is to provide communication with the patient 106 (FIGS. 1 and 2) in a discreet, tactful, circumspect manner as described above. In various aspects the feedback module 716 may be implemented to communicate with the patient 106 (FIGS. 1 and 2) using techniques that employ visual, audio, vibratory/tactile, olfactory, and taste.

Figure 10:
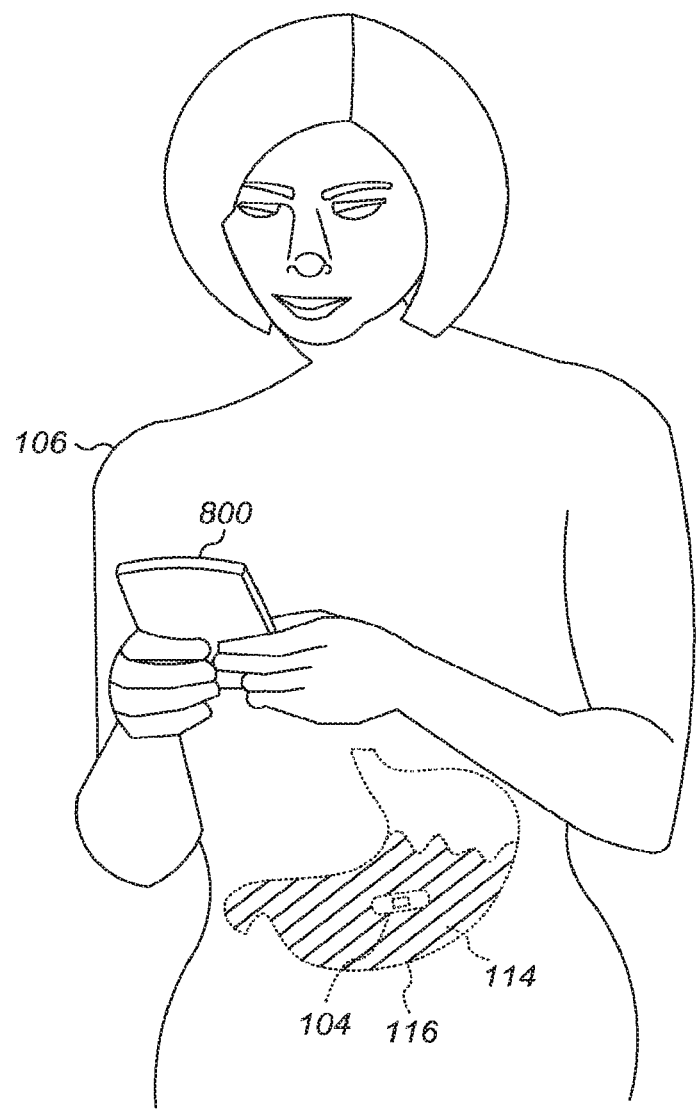
FIG. 10 illustrates a patient in the process of using one aspect of the mobile device comprising integrated electrodes, shown in FIGS. 8-9, for detecting an electrical signal generated by an ingestible event marker.

FIG. 8 illustrates one aspect of a mobile device 800 comprising integrated electrodes 804A, 804B for detecting electrical signals generated by an ingestible event marker, such as the IEM device 104 (FIGS. 1 and 2), for example. With reference now to FIGS. 8-10, the integrated electrodes 804A, 804B are coupled to a detection subsystem 516 (FIG. 9) similar to the detection subsystem 516 (FIGS. 5-7). In this particular aspect, the electrodes are replaced by the integrated electrodes 804A, 804B. Accordingly, in use, the patient 106 (FIG. 10) ingests the medication comprising the IEM device 104 (FIG. 10) and holds the mobile device 800 while contacting the electrodes 804A, 804B with both hands in order to couple the unique electrical current signature generated by the IEM device 104 to the detection subsystem 516. In another aspect, the mobile device with the contacting electrodes may be placed over a wrist-band or an arm-band which enables physical connectivity with the user.

The mobile device 800 also comprises a housing 806, a display 808, an input/output (I/O) system 810, an aperture 812 for capturing digital images, and an antenna 814. A high level description of similar functional modules was provided in connection with the mobile device 102 shown in FIG. 5 and for the sake of conciseness and clarity will not be repeated here.

FIG. 9 is system diagram of one aspect of a mobile device 900 for detecting an electrical signal generated by an ingestible event marker, such as the IEM device 104 (FIGS. 1, 2, 10), for example, configured to couple to the integrated electrodes 805A, 804B. As shown in FIG. 9, the mobile device 900 may comprise multiple elements. Although FIG. 9 shows a limited number of elements in a certain topology by way of example, it can be appreciated that additional or fewer elements in any suitable topology may be used in the mobile device 900 as desired for a given implementation. Furthermore, any element as described herein may be implemented using hardware, software, or a combination of both, as previously described with reference to node implementations. Aspects of the mobile device 900, however, are not limited in this context.

In various aspects, the mobile device 900 comprises a housing 806 and an antenna 814. The mobile device 900 also comprises a radio subsystem 514 connected via a bus to a processing subsystem 512. The radio subsystem 514 may perform voice and data communications operations using wireless shared media for the mobile device 900. The processing subsystem 512 may execute software for the mobile device 900. A bus may comprise a USB or micro-USB bus and appropriate interfaces, as well as others.

The detection subsystem 516, as previously described in connection with FIGS. 5-7, is coupled to the integrated electrodes 804A, 804B, which are configured to be touched by the patient 106 (FIG. 10) to conduct the unique electrical signature generated by the IEM device 104 (FIG. 10). Accordingly, once the patient 106 has ingested the IEM device 104 and contacts the integrated electrodes 804A, 804B, the detection subsystem 516 detects the unique current signature generated by the IEM device 104 and coupled through the integrated electrodes 804A, 804B. As previously discussed, the unique current signature generated by the IEM device 104 encodes the information associated with the IEM device 104, the medication, and/or the patient 106, among other information. The detection subsystem 516 is coupled to the processing subsystem 512 and provides the decoded sequence to the processing subsystem 512. The processing subsystem 512 activates the radio subsystem 514 to communicate the decoded information received from the IEM device 104 to the wireless node 120 (FIGS. 1, 2) or the cellular network 208 (FIG. 2). The imaging subsystem 508, navigation subsystem 510, processing subsystem, 512, and radio subsystem 514 were previously described in connection with FIG. 5 and will not be repeated here for the sake of conciseness and clarity of disclosure.

FIG. 10 illustrates a patient 106 in the process of using one aspect of the mobile device 800 comprising integrated electrodes 804A, 804B (FIG. 8) for detecting an electrical signal generated by an ingestible event marker, such as the IEM device 104, for example. As previously discussed, once the patient ingests the IEM device 104, the patient 106 holds the mobile device 800 by contacting the integrated electrodes 804A, 804B. The unique electrical current signature that is generated by the IEM device 104 when it dissolves in the digestive fluids 114 of the stomach 116 is coupled from the patient 106 to the integrated electrodes 804A, 804B and to the detection subsystem 516 (FIG. 9), as previously discussed.

Figure 12:
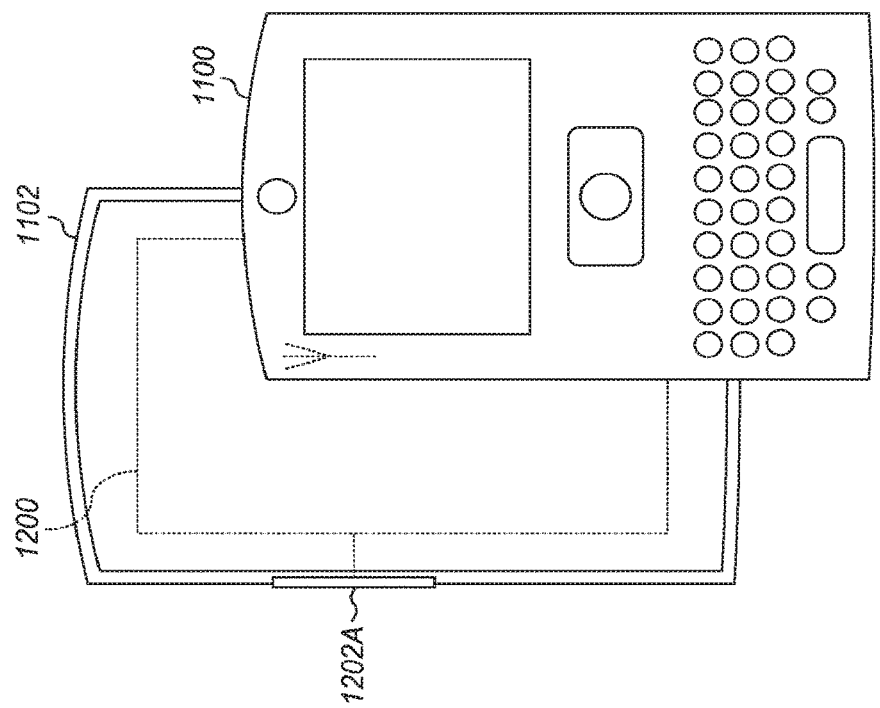
FIG. 12 illustrates the mobile device and the housing for receiving the mobile device shown in FIG. 11 in an unmated configuration.
Figure 11:
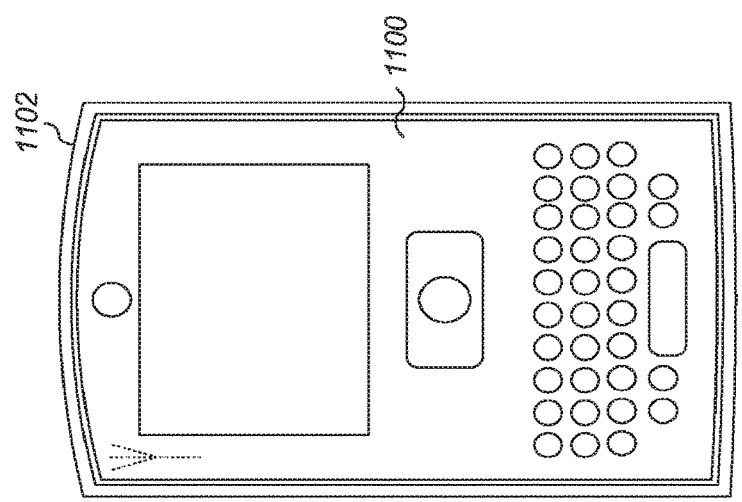
FIG. 11 illustrates one aspect of mobile device received in a mating configuration with a mobile device enclosing arrangement comprising a detection circuit integrated therewith for detecting an electrical signal generated by an ingestible event marker.

FIG. 11 illustrates one aspect of a mobile device 1100 received in a mating configuration with a mobile device enclosing arrangement 1102 comprising a detection circuit integrated therewith for detecting an electrical signal generated by an ingestible event marker, such as the IEM device 104 (FIGS. 1, 2, 10), for example. The enclosing arrangement 1102 may be referred to as a housing, enclosure, attachment, among others, and may substantially or partially cover or enclose the mobile device 1100. FIG. 12 illustrates the mobile device 1100 and the enclosing arrangement 1102 (cradle, protective cover, skin, and the like) for receiving the mobile device 1100 in an unmated configuration. The mobile device 1100 shown in FIGS. 11 and 12 is substantially similar to the mobile devices 102, 800 described hereinbefore and, therefore, a high level description of similar functional modules will not be repeated here for the sake of conciseness and clarity of disclosure.

As shown in FIGS. 11 and 12, the mobile device 1100 is configured to mate with the enclosing arrangement 1102. The enclosing arrangement 1102 contains a detection module 1200 integrated therewith. The detection module 1200 comprises a detection subsystem comprising an electrode input circuit similar to the detection subsystem 516 and electrode input circuit 602 described in connection with FIGS. 6 and 7. Due to the similarity of the detection subsystem and electrode input circuit components, the particular details will not be repeated here for the sake of conciseness and clarity of disclosure. The enclosing arrangement 1102 also includes electrodes 1202A and 1202B (not shown in FIG. 12 and shown in FIG. 13) to couple the patient to the detection module 1200. The detection module 1200 may be electrically coupled to functional modules of the mobile device 1100 to detect and process the unique electrical signature generated by the IEM device 104 (FIGS. 1, 2, 10). The detection module 1200 may be electrically coupled to the functional modules of the mobile device 1100 using any suitable techniques such as, for example, inductive coupling, wireless transmission, electrical connector, and the like. One example of a housing comprising a suitable connector to electrically couple the detection module 1200 to the functional modules of the mobile device 1100 is described in connection with FIG. 13.

Figures 13, 14:
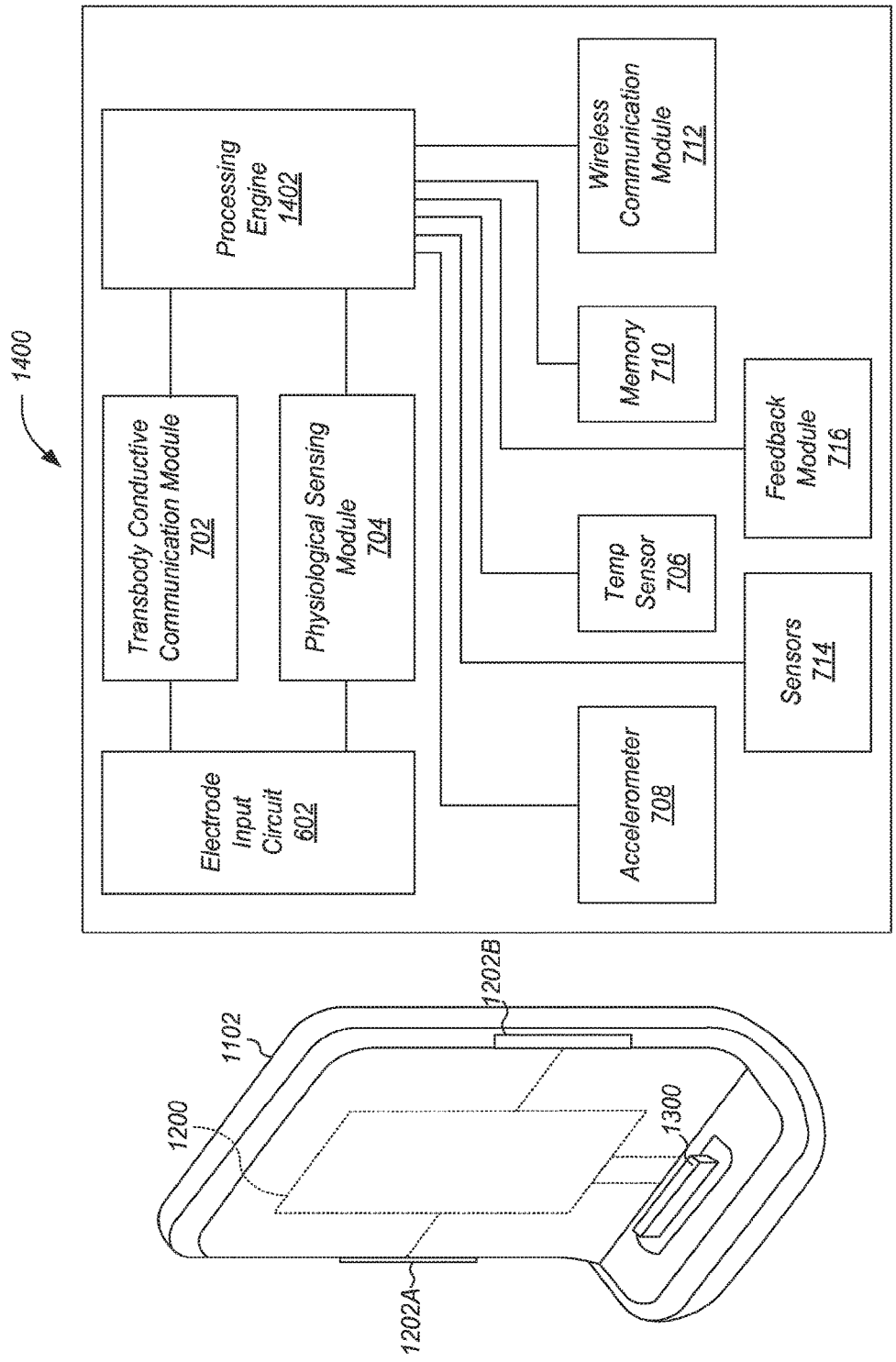
FIG. 13 illustrates one aspect of a housing for receiving a mobile device where the housing comprises a detection circuit for detecting an electrical signal generated by an ingestible event marker integrated therewith and a connector for electrically coupling the detection circuit to the functional modules of the mobile device.
FIG. 14 is a system diagram of one aspect of a detection circuit for detecting an electrical signal generated by an ingestible event marker.

FIG. 13 illustrates one aspect of a enclosing arrangement 1102 for receiving a mobile device where the enclosing arrangement 1102 comprises a detection circuit 1200 for detecting an electrical signal generated by an ingestible event marker integrated therewith and a connector 1300 for electrically coupling the detection circuit 1200 to the functional modules of the mobile device. In use, the mobile device (not shown) is slidably inserted over the enclosing arrangement 1102 and plugged into the connector 1300. The electrodes 1202A, 1202B are used tot couple the patient to the detection module 1200. The connector 1300 couples the detection module 1200 to the functional modules of the mobile device 1100 (FIG. 12) for communication purposes, among other purposes. In one aspect, the detection module 1200 integrated with the enclosing arrangement 1102 is a standalone module and includes all the necessary electronic modules to detect the unique electrical current signature generated by the IEM device.

FIG. 14 is a system diagram of one aspect of a detection circuit 1400 for detecting an electrical signal generated by an ingestible event marker, such as the IEM device 104 (FIGS. 1, 2, 10), for example. In one aspect, the detection circuit 1400 is a standalone module that includes a processing engine 1402. The processing engine 1402 is similar in functionality to the processing subsystem 512 previously discussed in connection with FIG. 5, for example. The electrode input circuit 602 receives electrical inputs from the electrodes 1202A, 1202B integrated with the enclosing arrangement 1102 (FIG. 13). The processing engine 1402 receives inputs from the transbody conductive communication module 702 and the physiological sensing module 704 and decodes the unique electrical signature generated by the IEM device 104 (FIGS. 1, 2, 10). The other modules including the temperature sensor 706, accelerometer 708, memory 710, wireless communication module 712, sensors 714, and feedback module 716 are optional and are also coupled to the processing engine 1402.

Figure 15:
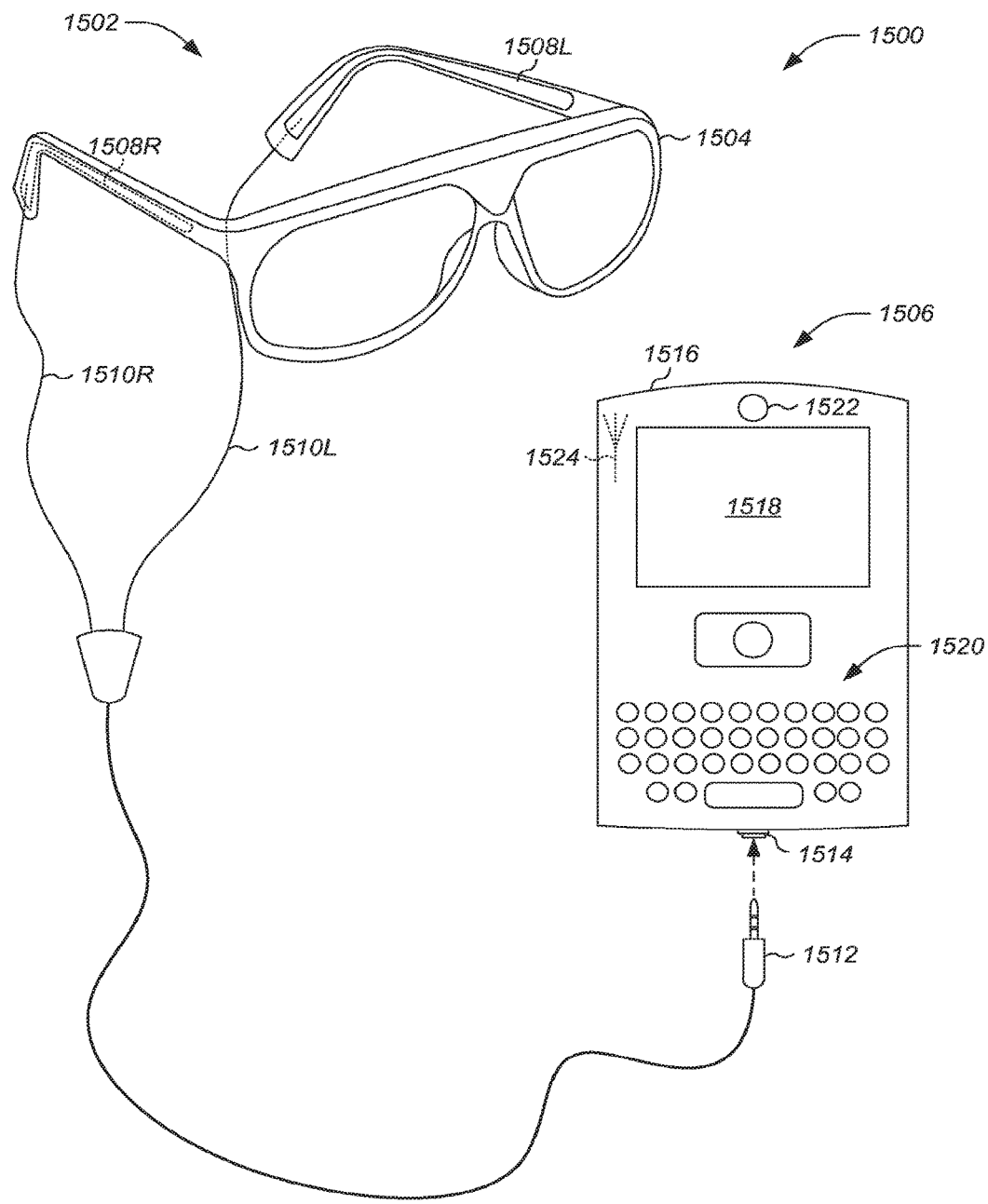
FIG. 15 illustrates one aspect of a system comprising a detection arrangement in the form of eyeglasses wiredly coupled to a mobile device for detecting an electrical signal generated by an ingestible event marker.

FIG. 15 illustrates one aspect of a system 1500 comprising an detection arrangement 1502 in the form of eyeglasses 1504 wiredly coupled to a mobile device 1506 for detecting an electrical signal generated by an ingestible event marker, such as the IEM device (FIGS. 1, 2, 10), for example. The detection arrangement 102 comprises a pair of eyeglasses 1504, or any form eyewear such as reading glasses, prescription glasses, sunglasses, and the like. The eyeglasses 1504 comprise electrodes 1508L, 1508R coupled by electrical conductors 1510R, 1510L to a plug 1512. The plug 1512 is received in a corresponding data port socket or jack connector 1514 portion of the mobile device 1506. The mobile device 1506 comprises a housing 1516, a display 1518, an input/output (I/O) system 1520, an aperture 1522 for capturing digital images, and an antenna 1524. A high level description of the functional modules of the mobile device 1506 has been provided herein in connection with FIGS. 4-7, with the eyeglasses 1504 replacing the ear buds 110R, 110L, and will not be repeated for the sake of conciseness and clarity of disclosure. The mobile device 1506 comprises a detection subsystem and an electrode input circuit similar to the detection subsystem 516 and the electrode input circuit 602 described in connection with FIGS. 4-7, for example.

Accordingly, with reference now to FIGS. 15, 1, 2, 4-7, and 10 in use, the patient 106 puts on the eyeglasses 1504 ensuring that there is sufficient contact of the electrodes 1508R, 1508L with the patient's skin and electrically couples the electrodes 1508R, 1508L into the mobile device 1506 by connecting the plug 1512 into the corresponding jack 1514 in the mobile device 1506. It will be appreciated that any suitable connection arrangements is contemplated to be within the scope of the present disclosure other than the plug/jack connection arrangement shown in FIG. 15. Such other connection arrangements include, without limitation, data ports, USB, socket, audio/video type connectors, among other suitable connection mechanisms. Once the detection arrangement 1502 is located in place, the patient 106 ingests the IEM device 104 and upon dissolving in the digestive fluids 114 of the stomach 116, the IEM device 104 powers up and initiates conduction of a unique electrical current signature signal, which encodes information associated with the IEM device 104, the medication, the patient 106, among other information. The unique electrical current signature signal is detected by the electrodes 1508R, 1508L and is coupled via the electrical conductors 1510R, 1510L to the mobile device 1506 where the electrode input circuit 602 portion of the detection subsystem 516 to decode the signal and communicate the information to the processing subsystem 512 of the mobile device 1506. In other aspects, the detection subsystem 512 may include a dedicated processing engine 1402 as described in connection with FIG. 14, without limitation.

Figure 16:
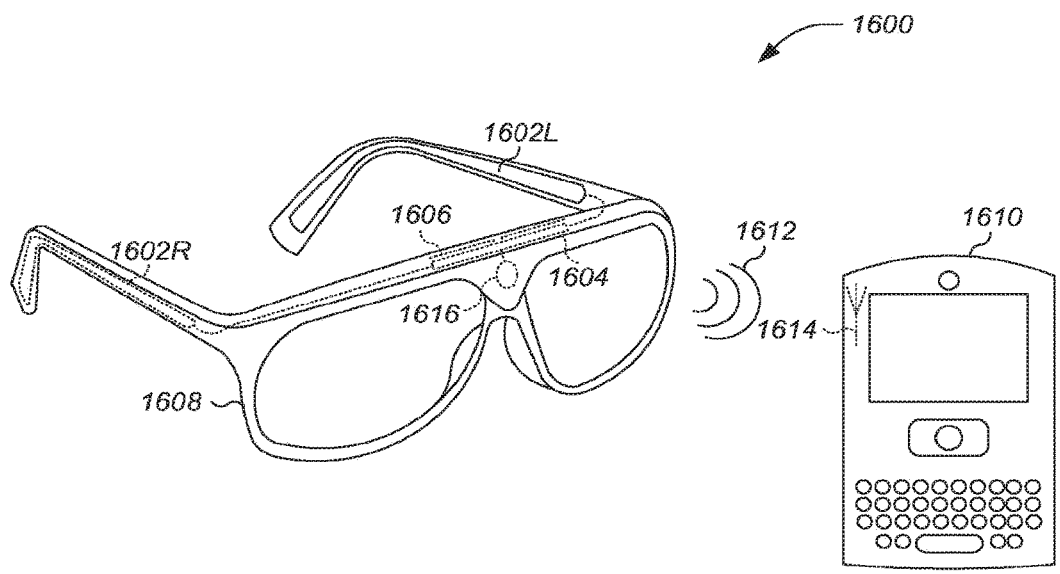
FIG. 16 illustrates one aspect of a system comprising electrodes, detection circuit module, and antenna integrated in a pair of eyeglasses wirelessly coupled to a mobile device for detecting an electrical signal generated by an ingestible event marker.

FIG. 16 illustrates one aspect of a system 1600 comprising electrodes 1602R, 1602L, detection circuit module 1604, and antenna 1606 integrated in a pair of eyeglasses 1608 wirelessly coupled to a mobile device 1610 for detecting an electrical signal generated by an ingestible event marker. As shown in FIG. 16, the detection circuit module 1604 including the electrode input circuit and detection subsystem are embedded in the eyeglasses 1608 to essentially eliminate the need for the electrical conductors 1510R, 1510L as shown in FIG. 15, for example. The wireless signal 1612 transmitted by the detection circuit module 1604 may be received by the onboard antenna 1614 of the wireless device 1610. In one aspect, the detection circuit module 1604 may communicate with the mobile device 1610 using Bluetooth or other suitable proprietary open wireless technology standard for exchanging data over short distances. In other aspects, other wireless communications such as the Wi-Fi (IEEE 802.11) wireless standard for connecting electronic devices.

In one aspect, the eyeglasses 1608 may include a battery 1616 embedded therein to supply electrical power to the detection circuit module 1604. In other aspects, a wireless power transfer technique commonly employed in RFID tags or by inductive coupling may be employed instead of the battery 1616. In one aspect, the mobile device 1610 may be configured to transmit an interrogation signal to the detection circuit module 1604 which serves to power up the detection circuit module 1604 and initiate taking readings and wirelessly transmitting information back to the mobile device 1610.

Once the detection circuit module 1604 transmits the information associated with the IEM device to the mobile device 1610, the mobile device 1610 can act as a hub to transfer the information to a local wireless node or remote node via the cellular network, Wi-Fi, Bluetooth, or other suitable wireless communication technique.

Figure 17:
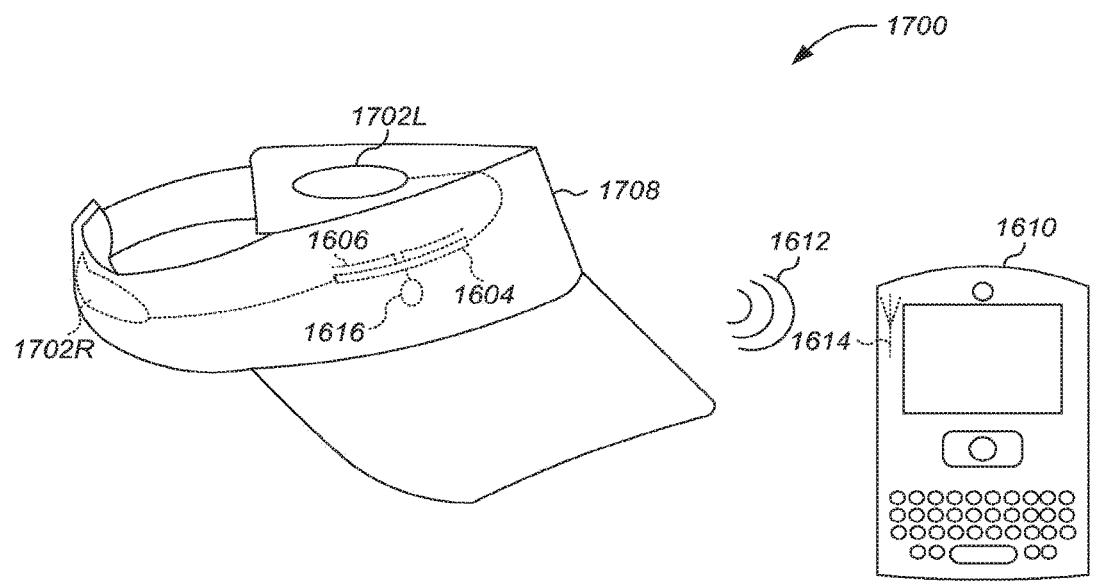
FIG. 17 illustrates one aspect of a system comprising electrodes, detection circuit module, and antenna integrated in a visor wirelessly coupled to a mobile device for detecting an electrical signal generated by an ingestible event marker.

FIG. 17 illustrates one aspect of a system 1700 comprising electrodes 1702R, 1702L, detection circuit module 1604, and antenna 1606 integrated in a in a visor 1708 wirelessly coupled to a mobile device 1610 for detecting an electrical signal generated by an ingestible event marker. As shown in FIG. 17, the detection circuit module 1604 including the electrode input circuit and detection subsystem are embedded in the visor 1708 to essentially eliminate the need for the electrical conductors to couple the electrodes 1702R, 1702L to the mobile device 1610, for example. The wireless signal 1612 transmitted by the detection circuit module 1604 may be received by the onboard antenna 1614 of the wireless device 1610. In one aspect, the detection circuit module 1604 may communicate with the mobile device 1610 using Bluetooth or other suitable proprietary open wireless technology standard for exchanging data over short distances. In other aspects, other wireless communications such as the Wi-Fi (IEEE 802.11) wireless standard for connecting electronic devices.

In one aspect, the visor 1708 may include a battery 1616 embedded therein to supply electrical power to the detection circuit module 1604. In other aspects, a wireless power transfer technique commonly employed in RFID tags or by inductive coupling may be employed instead of the battery 1616. In one aspect, the mobile device 1610 may be configured to transmit an interrogation signal to the detection circuit module 1604 which serves to power up the detection circuit module 1604 and initiate taking readings from the IEM device and wirelessly transmitting the information back to the mobile device 1610.

Once the detection circuit module 1604 transmits the information associated with the IEM device to the mobile device 1610, the mobile device 1610 can act as a hub to transfer the information to a local wireless node or remote node via the cellular network, Wi-Fi, Bluetooth, or other suitable wireless communication technique.

Figure 18:
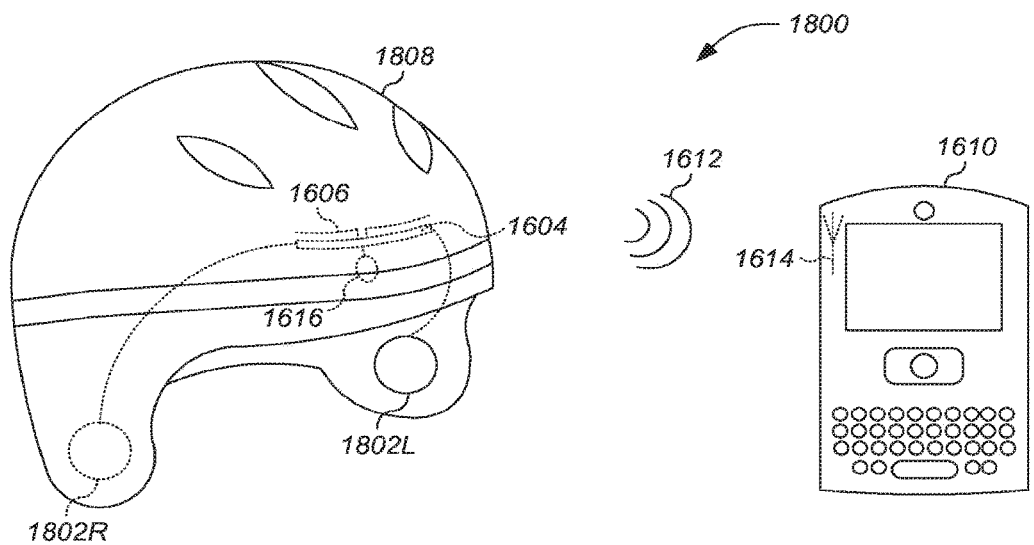
FIG. 18 illustrates one aspect of a system comprising electrodes, detection circuit module, and antenna integrated in a helmet wirelessly coupled to a mobile device for detecting an electrical signal generated by an ingestible event marker.

FIG. 18 illustrates one aspect of a system 1800 comprising electrodes 1802R, 1802L, detection circuit module 1604, and antenna 1606 integrated in a helmet 1808 wirelessly coupled to a mobile device 1610 for detecting an electrical signal generated by an ingestible event marker. As shown in FIG. 18, the detection circuit module 1604 including the electrode input circuit and detection subsystem are embedded in the helmet 1808 to essentially eliminate the need for the electrical conductors to couple the electrodes 1802R, 1802L to the mobile device 1610, for example. The wireless signal 1612 transmitted by the detection circuit module 1604 may be received by the onboard antenna 1614 of the wireless device 1610. In one aspect, the detection circuit module 1604 may communicate with the mobile device 1610 using Bluetooth or other suitable proprietary open wireless technology standard for exchanging data over short distances. In other aspects, other wireless communications such as the Wi-Fi (IEEE 802.11) wireless standard for connecting electronic devices.

In one aspect, the helmet 1808 may include a battery 1616 embedded therein to supply electrical power to the detection circuit module 1604. In other aspects, a wireless power transfer technique commonly employed in RFID tags or by inductive coupling may be employed instead of the battery 1616. In one aspect, the mobile device 1610 may be configured to transmit an interrogation signal to the detection circuit module 1604 which serves to power up the detection circuit module 1604 and initiate taking readings from the IEM device and wirelessly transmitting the information back to the mobile device 1610.

Once the detection circuit module 1604 transmits the information associated with the IEM device to the mobile device 1610, the mobile device 1610 can act as a hub to transfer the information to a local wireless node or remote node via the cellular network, Wi-Fi, Bluetooth, or other suitable wireless communication technique.

Figure 19:
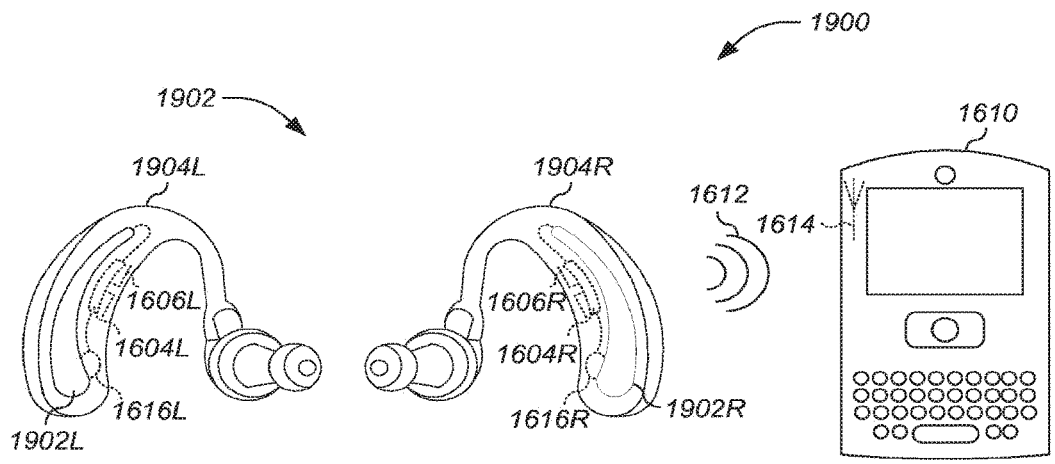
FIG. 19 illustrates one aspect of a system comprising electrodes, detection circuit module, and antenna integrated in a set of hearing aids wirelessly coupled to a mobile device for detecting an electrical signal generated by an ingestible event marker.

FIG. 19 illustrates one aspect of a system 1900 comprising electrodes 1902R, 1902L, detection circuit modules 1604R, 1604L, and antennas 1606R integrated in a pair of hearing aids 1904R, 1904L wirelessly coupled to a mobile device 1610 for detecting an electrical signal generated by an ingestible event marker. As shown in FIG. 19, the detection circuit module(s) 1604R, 1604L including the electrode input circuit and detection subsystem are embedded in the hearing aid(s) 1904R, 1904L to essentially eliminate the need for the electrical conductors to couple the electrodes 1902R, 1902L to the mobile device 1610, for example. The wireless signal 1612 transmitted by the either one of the detection circuit modules 1604R, 1604L may be received by the onboard antenna 1614 of the wireless device 1610. In one aspect, either one of the detection circuit modules 1604R, 1604L may communicate with the mobile device 1610 using Bluetooth or other suitable proprietary open wireless technology standard for exchanging data over short distances. In other aspects, other wireless communications such as the Wi-Fi (IEEE 802.11) wireless standard for connecting electronic devices.

In one aspect, the hearing aid(s) 1904R, 1904L may include a battery 1616 embedded therein to supply electrical power to either one of the detection circuit modules 1604R, 1604L. In other aspects, a wireless power transfer technique commonly employed in RFID tags or by inductive coupling may be employed instead of the battery 1616. In one aspect, the mobile device 1610 may be configured to transmit an interrogation signal to either one of the detection circuit modules 1604R, 1604L which serves to power up either one of the detection circuit modules 1604R, 1604L and initiate taking readings from the IEM device and wirelessly transmitting the information back to the mobile device 1610.

Once either one of the detection circuit modules 1604R, 1604L transmit the information associated with the IEM device to the mobile device 1610, the mobile device 1610 can act as a hub to transfer the information to a local wireless node or remote node via the cellular network, Wi-Fi, Bluetooth, or other suitable wireless communication technique.

Figure 20:
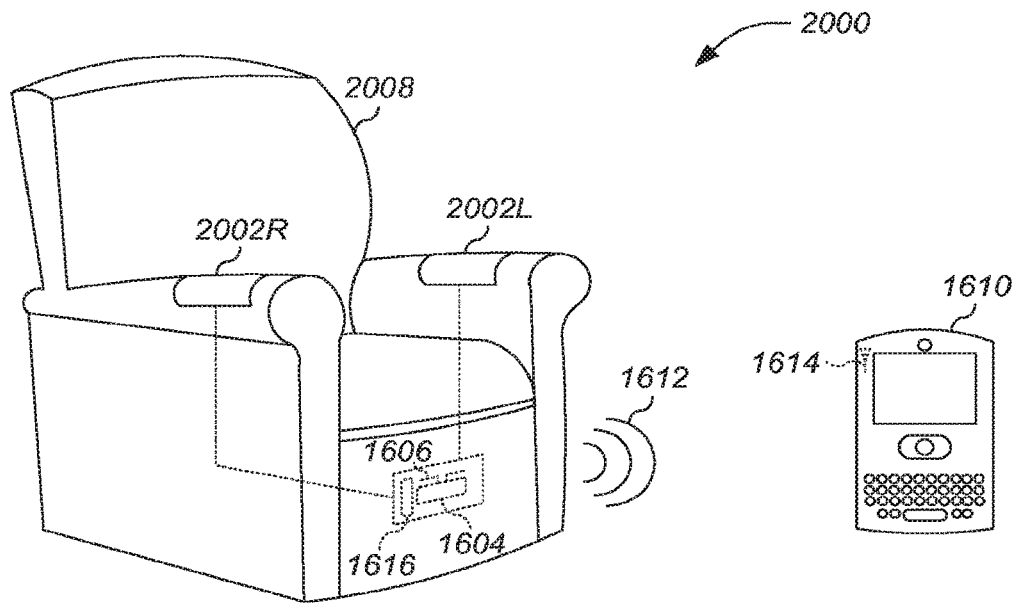
FIG. 20 illustrates one aspect of a system comprising electrodes, detection circuit module, and antenna integrated in a chair wirelessly coupled to a mobile device for detecting an electrical signal generated by an ingestible event marker.

FIG. 20 illustrates one aspect of a system 2000 comprising electrodes 2004R, 2004L, detection circuit module 1604, and antenna 1606 integrated in a chair 2008 wirelessly coupled to a mobile device 1610 for detecting an electrical signal generated by an ingestible event marker. As shown in FIG. 20, the detection circuit module 1604 including the electrode input circuit and detection subsystem are embedded in the chair 2008 to essentially eliminate the need for the electrical conductors to couple the electrodes 2002R, 2002L to the mobile device 1610, for example. The wireless signal 1612 transmitted by the detection circuit module 1604 may be received by the onboard antenna 1614 of the wireless device 1610. In one aspect, the detection circuit module 1604 may communicate with the mobile device 1610 using Bluetooth or other suitable proprietary open wireless technology standard for exchanging data over short distances. In other aspects, other wireless communications such as the Wi-Fi (IEEE 802.11) wireless standard for connecting electronic devices.

In one aspect, the chair 2008 may include a battery 1616 embedded therein to supply electrical power to the detection circuit module 1604 or may be plugged into a household altering current (AC) mains socket. In other aspects, a wireless power transfer technique commonly employed in RFID tags or by inductive coupling may be employed instead of the battery 1616. In one aspect, the mobile device 1610 may be configured to transmit an interrogation signal to the detection circuit module 1604 which serves to power up the detection circuit module 1604 and initiate taking readings from the IEM device and wirelessly transmitting the information back to the mobile device 1610.

Once the detection circuit module 1604 transmits the information associated with the IEM device to the mobile device 1610, the mobile device 1610 can act as a hub to transfer the information to a local wireless node or remote node via the cellular network, Wi-Fi, Bluetooth, or other suitable wireless communication technique.

Figure 21:
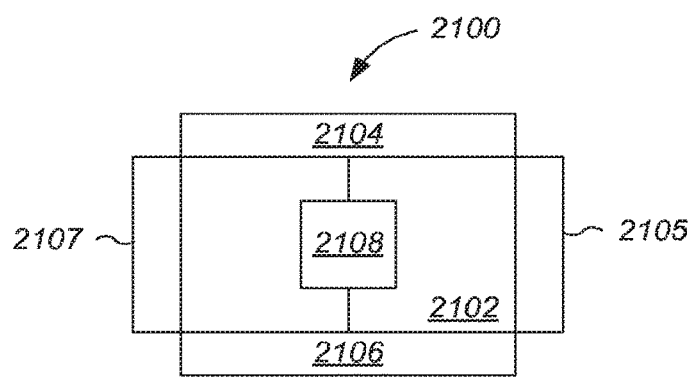
FIG. 21 illustrates a system corresponding to one aspect of an ingestible event marker device.

FIG. 21 illustrates a system 2100 corresponding to one aspect of an ingestible event marker device. In various aspects the IEM devices 104 shown in FIGS. 1 and 2, for example, may be implemented in accordance with the system 2100 shown in FIG. 21. The system 2100 can be used in association with any medication product, as mentioned above, to determine the origin of the medication and to confirm that at least one of the right type and the right dosage of medication was delivered to the patient and in some aspects to determine when a patient takes the medication product. The scope of the present disclosure, however, is not limited by the environment and the medication product that may be used with the system 2100. For example, the system 2100 may be activated either in wireless mode, in galvanic mode by placing the system 2100 within a capsule and then placing the capsule within a conducting fluid, or a combination thereof, or exposing the system 2100 to air. Once placed in a conducting fluid, for example, the capsule would dissolve over a period of time and release the system 2100 into the conducting fluid. Thus, in one aspect, the capsule would contain the system 2100 and no product. Such a capsule may then be used in any environment where a conducting fluid is present and with any product. For example, the capsule may be dropped into a container filled with jet fuel, salt water, tomato sauce, motor oil, or any similar product. Additionally, the capsule containing the system 2100 may be ingested at the same time that any pharmaceutical product is ingested in order to record the occurrence of the event, such as when the product was taken.

In the specific example of the system 2100 shown in FIG. 21, when the system 2100 is combined with a medication or pharmaceutical product, as the product or pill is ingested, or exposed to air, the system 2100 is activated in galvanic mode. The system 2100 controls conductance to produce a unique electrical current signature that is detected by the electrode assemblies (e.g., 108 . . . etc., described herein), for example, thereby signifying that the pharmaceutical product has been taken. When activated in wireless mode, the system controls modulation of capacitive plates to produce a unique voltage signature associated with the system 2100 that is detected. Various aspects of the system 2100 are described in commonly assigned U.S. Patent Application Applications Pharma Informatics System, filed Apr. 28, 2006, published as 2008-0284599 A1; Highly Reliable Ingestible Event Markers and Methods for Using Same, filed Apr. 27, 2009, published as 2011-0054265 A1; Miniature Ingestible Device, filed Apr. 6, 2011 as International Application No. PCT/US11/31536; Ingestible Device with Pharmaceutical Product, filed Nov. 22, 2010, and the following U.S. Application No. 61/416,150; Wireless Energy Sources for Integrated Circuits, filed Dec. 29, 2010, Application No. 61/428,055; Communication System with Remote Activation, filed Jul. 11, 2011, application Ser. No. 13/180,516; Communication System with Multiple Sources of Power, filed Jul. 11, 2011, application Ser. No. 13/180,498; Communication System Using an Implantable Device, filed Jul. 11, 2011, application Ser. No. 13/180,539; Communication System with Enhanced Partial Power and Method of Manufacturing Same, filed Jul. 11, 2011, application Ser. No. 13/180,525; Communication System Using Polypharmacy Co-Packaged Medication Dosing Unit, filed Jul. 11, 2011, application Ser. No. 13/180,538; Communication System Incorporated in an Ingestible Product, filed Jul. 11, 2011, application Ser. No. 13/180,507; each of the disclosures of which is entirely herein incorporated by reference.

In one aspect, the system 2100 includes a framework 2102. The framework 2102 is a chassis for the system 2100 and multiple components are attached to, deposited upon, or secured to the framework 2102. In this aspect of the system 2100, a digestible material 2104 is physically associated with the framework 2102. The material 2104 may be chemically deposited on, evaporated onto, secured to, or built-up on the framework all of which may be referred to herein as "deposit" with respect to the framework 2102. The material 2104 is deposited on one side of the framework 2102. The materials of interest that can be used as material 2104 include, but are not limited to: Cu, CuCl, or CuI. The material 2104 is deposited by physical vapor deposition, electrodeposition, or plasma deposition, among other protocols. The material 2104 may be from about 0.05 to about 500 µm thick, such as from about 5 to about 100 µm thick. The shape is controlled by shadow mask deposition, or photolithography and etching. Additionally, even though only one region is shown for depositing the material, each system 2100 may contain two or more electrically unique regions where the material 2104 may be deposited, as desired.

At a different side, which is the opposite side as shown in FIG. 21, another digestible material 2106 is deposited, such that the materials 2104, 2106 are dissimilar and insulated from each other. Although not shown, the different side selected may be the side next to the side selected for the material 2104. The scope of the present disclosure is not limited by the side selected and the term "different side" can mean any of the multiple sides that are different from the first selected side. In various aspects, the dissimilar material may be located at different positions on a same side. Furthermore, although the shape of the system is shown as a square, the shape may be any geometrically suitable shape. The materials 2104, 2106 are selected such that they produce a voltage potential difference when the system 2100 is in contact with conducting liquid, such as body fluids. The materials of interest for material 2106 include, but are not limited to: Mg, Zn, or other electronegative metals. As indicated above with respect to the material 2104, the material 2106 may be chemically deposited on, evaporated onto, secured to, or built-up on the framework. Also, an adhesion layer may be necessary to help the material 2106 (as well as material 2104 when needed) to adhere to the framework 2102. Typical adhesion layers for the material 2106 are Ti, TiW, Cr or similar material. Anode material and the adhesion layer may be deposited by physical vapor deposition, electrodeposition or plasma deposition. The material 2106 may be from about 0.05 to about 500 µm thick, such as from about 5 to about 100 µm thick. However, the scope of the present disclosure is not limited by the thickness of any of the materials nor by the type of process used to deposit or secure the materials to the framework 2102.

According to the disclosure set forth, the materials 2104, 2106 can be any pair of materials with different electrochemical potentials. Additionally, in the aspects wherein the system 2100 is used in-vivo, the materials 2104, 2106 may be vitamins that can be absorbed. More specifically, the materials 2104, 2106 can be made of any two materials appropriate for the environment in which the system 2100 will be operating. For example, when used with an ingestible product, the materials 2104, 2106 are any pair of materials with different electrochemical potentials that are ingestible. An illustrative example includes the instance when the system 2100 is in contact with an ionic solution, such as stomach acids. Suitable materials are not restricted to metals, and in certain aspects the paired materials are chosen from metals and non-metals, e.g., a pair made up of a metal (such as Mg) and a salt (such as CuCl or CuI). With respect to the active electrode materials, any pairing of substances—metals, salts, or intercalation compounds—with suitably different electrochemical potentials (voltage) and low interfacial resistance are suitable.

Materials and pairings of interest include, but are not limited to, those reported in TABLE 1 below. In one aspect, one or both of the metals may be doped with a non-metal, e.g., to enhance the voltage potential created between the materials as they come into contact with a conducting liquid. Non-metals that may be used as doping agents in certain aspects include, but are not limited to: sulfur, iodine, and the like. In another aspect, the materials are copper iodine (CuI) as the anode and magnesium (Mg) as the cathode. Aspects of the present disclosure use electrode materials that are not harmful to the human body.

TABLE 1

| | Anode | Cathode |
|---|---|---|
| Metals | Magnesium, Zinc Sodium, Lithium Iron | |
| Salts | | Copper salts: iodide, chloride, bromide, sulfate, formate, (other anions possible) $Fe^{3+}$ salts: e.g. orthophosphate, pyrophosphate, (other anions possible) Oxygen or H+ on platinum, gold or other catalytic surfaces |
| Intercalation compounds | Graphite with Li, K, Ca, Na, Mg | Vanadium oxide Manganese oxide |

Thus, when the system 2100 is in contact with the conducting fluid, a current path is formed through the conducting fluid between the dissimilar materials 2104, 2106. A control device 2108 is secured to the framework 2102 and electrically coupled to the materials 2104, 2106. The control device 2108 includes electronic circuitry, for example control logic that is capable of controlling and altering the conductance between the materials 2104, 2106.

The voltage potential created between the dissimilar materials 2104, 2106 provides the power for operating the system as well as produces the current flow through the conducting fluid and the system 2100. In one aspect, the system 2100 operates in direct current mode. In an alternative aspect, the system 720 controls the direction of the current so that the direction of current is reversed in a cyclic manner, similar to alternating current. As the system reaches the conducting fluid or the electrolyte, where the fluid or electrolyte component is provided by a physiological fluid, e.g., stomach acid, the path for current flow between the dissimilar materials 2104, 2106 is completed external to the system 2100; the current path through the system 2100 is controlled by the control device 2108. Completion of the current path allows for the current to flow and in turn a receiver, not shown, can detect the presence of the current and recognize that the system 2100 has been activate and the desired event is occurring or has occurred.

In one aspect, the two dissimilar materials 2104, 2106 are similar in function to the two electrodes needed for a direct current power source, such as a battery. The conducting liquid acts as the electrolyte needed to complete the power source. The completed power source described is defined by the electrochemical reaction between the materials 2104, 2106 of the system 2100 and enabled by the fluids of the body. The completed power source may be viewed as a power source that exploits electrochemical conduction in an ionic or a conducting solution such as gastric fluid, blood, or other bodily fluids and some tissues. Additionally, the environment may be something other than a body and the liquid may be any conducting liquid. For example, the conducting fluid may be salt water or a metallic based paint.

In certain aspects, the two dissimilar materials 2104, 2106 are shielded from the surrounding environment by an additional layer of material. Accordingly, when the shield is dissolved and the two dissimilar materials 2104, 2106 are exposed to the target site, a voltage potential is generated.

In certain aspects, the complete power source or supply is one that is made up of active electrode materials, electrolytes, and inactive materials, such as current collectors, packaging. The active materials are any pair of materials with different electrochemical potentials. Suitable materials are not restricted to metals, and in certain aspects the paired materials are chosen from metals and non-metals, e.g., a pair made up of a metal (such as Mg) and a salt (such as CuI). With respect to the active electrode materials, any pairing of substances—metals, salts, or intercalation compounds—with suitably different electrochemical potentials (voltage) and low interfacial resistance are suitable.

A variety of different materials may be employed as the materials that form the electrodes. In certain aspects, electrode materials are chosen to provide for a voltage upon contact with the target physiological site, e.g., the stomach, sufficient to drive the system of the identifier. In certain aspects, the voltage provided by the electrode materials upon contact of the metals of the power source with the target physiological site is 0.001 V or higher, including 0.01 V or higher, such as 0.1 V or higher, e.g., 0.3 V or higher, including 0.5 volts or higher, and including 1.0 volts or higher, where in certain aspects, the voltage ranges from about 0.001 to about 10 volts, such as from about 0.01 to about 10 V.

Still referring to FIG. 21, the dissimilar materials 2104, 2106 provide the voltage potential to activate the control device 2108. Once the control device 2108 is activated or powered up, the control device 2108 can alter conductance between the first and second materials 2104, 2106 in a unique manner. By altering the conductance between the first and second materials 2104, 2106, the control device 2108 is capable of controlling the magnitude of the current through the conducting liquid that surrounds the system 2100. This produces a unique current signature that can be detected and measured by a receiver (not shown), which can be positioned internal or external to the body. The receiver is disclosed in greater detail in U.S. patent application Ser. No. 12/673,326 entitled "BODY-ASSOCIATED RECEIVER AND METHOD" filed on Dec. 15, 2009, and published as 2010-0312188 A1 dated Dec. 9, 2010 which is incorporated herein by reference in its entirety. In addition to controlling the magnitude of the current path between the materials, non-conducting materials, membrane, or "skirt" are used to increase the "length" of the current path and, hence, act to boost the conductance path, as disclosed in the U.S. patent application Ser. No. 12/238,345 entitled, "IN-BODY DEVICE WITH VIRTUAL DIPOLE SIGNAL AMPLIFICATION" filed Sep. 25, 2008, the entire content of which is incorporated herein by reference. Alternatively, throughout the disclosure herein, the terms "non-conducting material," "membrane," and "skirt" are interchangeably used with the term "current path extender" without impacting the scope or the present aspects and the claims herein. The skirt, shown in portion at 2105, 2107, respectively, may be associated with, e.g., secured to, the framework 2102. Various shapes and configurations for the skirt are contemplated as within the scope of the various aspects of the present invention. For example, the system 2100 may be surrounded entirely or partially by the skirt and the skirt maybe positioned along a central axis of the system 2100 or off-center relative to a central axis. Thus, the scope of the present disclosure as claimed herein is not limited by the shape or size of the skirt. Furthermore, in other aspects, the dissimilar materials 2104, 2106 may be separated by one skirt that is positioned in any defined region between the dissimilar materials 2104, 2106.

The system 2100 may be grounded through a ground contact. The system 720 also may include a sensor module. In operation, ion or current paths are established between the first material 2104 to the second material 2106 and through a conducting fluid in contact with the system 2100. The voltage potential created between the first and second materials 2104, 2106 is created through chemical reactions between the first and second materials 2104, 2106 and the conducting fluid. In one aspect, the surface of the first material 2104 is not planar, but rather an irregular surface. The irregular surface increases the surface area of the material and, hence, the area that comes in contact with the conducting fluid.

In one aspect, at the surface of the first material 2104, there is an electrochemical reaction between the material 2104 and the surrounding conducting fluid such that mass is released into the conducting fluid. The term "mass" as used herein includes any ionic or non-ionic species that may be added or removed from the conductive fluid as part of the electrochemical reactions occurring on material 2104. One example includes the instant where the material is CuCl and when in contact with the conducting fluid, CuCl is converted to Cu metal (solid) and Cl— is released into solution. The flow of positive ions into the conduction fluid is via current path(s). Negative ions flow in the opposite direction. In a similar manner, there is an electrochemical reaction involving the second material 2106 that results in ions released or removed from the conducting fluid. In this example, the release of negative ions at the material 2104 and the release of positive ions by the material 36 are related to each other through the current flow that is controlled by control device 38. The rate of reaction and hence the ionic emission rate or current, is controlled by the control device 2108. The control device 2108 can increase or decrease the rate of ion flow by altering its internal conductance, which alters the impedance, and therefore the current flow and reaction rates at the materials 2104, 2106. Through controlling the reaction rates, the system 2100 can encode information in the ionic flow. Thus, the system 2100 encodes information using ionic emission or flow.

The control device 2108 can vary the duration of a fixed ionic exchange rate or current flow magnitude while keeping the rate or magnitude near constant, similar to when the frequency is modulated and the amplitude is constant. Also, the control device 2108 can vary the level of the ionic exchange rate or the magnitude of the current flow while keeping the duration near constant. Thus, using various combinations of changes in duration and altering the rate or magnitude, the control device 2108 encodes information in the current flow or the ionic exchange. For example, the control device 2108 may use, but is not limited to any of the following techniques namely, Binary Phase-Shift Keying (PSK), Frequency Modulation (FM), Amplitude Modulation (AM), On-Off Keying, and PSK with On-Off Keying.

Various aspects of the system 2100 may comprise electronic components as part of the control device 2108. Components that may be present include but are not limited to: logic and/or memory elements, an integrated circuit, an inductor, a resistor, and sensors for measuring various parameters. Each component may be secured to the framework and/or to another component. The components on the surface of the support may be laid out in any convenient configuration. Where two or more components are present on the surface of the solid support, interconnects may be provided.

The system 2100 controls the conductance between the dissimilar materials and, hence, the rate of ionic exchange or the current flow. Through altering the conductance in a specific manner the system is capable of encoding information in the ionic exchange and the current signature. The ionic exchange or the current signature is used to uniquely identify the specific system. Additionally, the system 2100 is capable of producing various different unique exchanges or signatures and, thus, provides additional information. For example, a second current signature based on a second conductance alteration pattern may be used to provide additional information, which information may be related to the physical environment. To further illustrate, a first current signature may be a very low current state that maintains an oscillator on the chip and a second current signature may be a current state at least a factor of ten higher than the current state associated with the first current signature.

Referring now to FIG. 22, in another aspect of an ingestible device is shown in more detail as system 2040. The system 2040 includes a framework 2042. In this aspect of the system 2040, a digestible or dissolvable material 2044 is deposited on a portion of one side of the framework 2042. At a different portion of the same side of the framework 2042, another digestible material 2046 is deposited, such that materials 2044 and 2046 are dissimilar. More specifically, material 2044 and 2046 are selected such that they form a voltage potential difference when in contact with a conducting liquid, such as body fluids. Thus, when the system 2040 is in contact with and/or partially in contact with the conducting liquid, then a current path, an example is shown in FIG. 23, is formed through the conducting liquid between material 2044 and 2046. A control device 2048 is secured to the framework 2042 and electrically coupled to the materials 2044 and 2046. The control device 2048 includes electronic circuitry that is capable of controlling part of the conductance path between the materials 2044 and 2046. The materials 2044 and 2046 are separated by a non-conducting skirt 2049. Various examples of the skirt 2049 are disclosed in U.S. Provisional Application No. 61/173,511 filed on Apr. 28, 2009 and entitled "HIGHLY RELIABLE INGESTIBLE EVENT MARKERS AND METHODS OF USING SAME" and U.S. Provisional Application No. 61/173,564 filed on Apr. 28, 2009 and entitled "INGESTIBLE EVENT MARKERS HAVING SIGNAL AMPLIFIERS THAT COMPRISE AN ACTIVE AGENT"; as well as U.S. application Ser. No. 12/238,345 filed Sep. 25, 2008 and published as 2009-0082645, entitled "IN-BODY DEVICE WITH VIRTUAL DIPOLE SIGNAL AMPLIFICATION"; the entire disclosure of each is incorporated herein by reference.

Once the control device 2048 is activated or powered up, the control device 2048 can alter conductance between the materials 2044 and 2046. Thus, the control device 2048 is capable of controlling the magnitude of the current through the conducting liquid that surrounds the system 2040. As indicated above with respect to system 2030, a unique current signature that is associated with the system 2040 can be detected by a receiver (not shown) to mark the activation of the system 2040. In order to increase the "length" of the current path the size of the skirt 2049 is altered. The longer the current path, the easier it may be for the receiver to detect the current.

Referring now to FIG. 23, the system 2030 of FIG. 21 is shown in an activated state and in contact with conducting liquid. The system 2030 is grounded through ground contact 2052. The system 2030 also includes a sensor module 2074, which is described in greater detail with respect to FIG. 24. Ion or current paths 2050 form between material 2034 to material 2036 through the conducting fluid in contact with the system 2030. The voltage potential created between the material 2034 and 2036 is created through chemical reactions between materials 2034/2036 and the conducting fluid.

FIG. 23A shows an exploded view of the surface of the material 2034. The surface of the material 2034 is not planar, but rather an irregular surface 2054 as shown. The irregular surface 2054 increases the surface area of the material and, hence, the area that comes in contact with the conducting fluid.

In one aspect, at the surface of the material 2034, there is chemical reaction between the material 2034 and the surrounding conducting fluid such that mass is released into the conducting fluid. The term "mass" as used herein refers to protons and neutrons that form a substance. One example includes the instant where the material is CuCl and when in contact with the conducting fluid, CuCl becomes Cu (solid) and Cl.sup.− in solution. The flow of ions into the conduction fluid is depicted by the ion paths 2050. In a similar manner, there is a chemical reaction between the material 2036 and the surrounding conducting fluid and ions are captured by the material 2036. The release of ions at the material 2034 and capture of ion by the material 2036 is collectively referred to as the ionic exchange. The rate of ionic exchange and, hence the ionic emission rate or flow, is controlled by the control device 2038. The control device 2038 can increase or decrease the rate of ion flow by altering the conductance, which alters the impedance, between the materials 2034 and 2036. Through controlling the ion exchange, the system 2030 can encode information in the ionic exchange process. Thus, the system 2030 uses ionic emission to encode information in the ionic exchange.

The control device 2038 can vary the duration of a fixed ionic exchange rate or current flow magnitude while keeping the rate or magnitude near constant, similar to when the frequency is modulated and the amplitude is constant. Also, the control device 2038 can vary the level of the ionic exchange rate or the magnitude of the current flow while keeping the duration near constant. Thus, using various combinations of changes in duration and altering the rate or magnitude, the control device 2038 encodes information in the current flow or the ionic exchange. For example, the control device 2038 may use, but is not limited to any of the following techniques namely, Binary Phase-Shift Keying (PSK), Frequency modulation, Amplitude modulation, on-off keying, and PSK with on-off keying.

As indicated above, the various aspects disclosed herein, such as systems 2100 and 2040 of FIGS. 21 and 22, respectively, include electronic components as part of the control device 2038 or the control device 2048. Components that may be present include but are not limited to: logic and/or memory elements, an integrated circuit, an inductor, a resistor, and sensors for measuring various parameters. Each component may be secured to the framework and/or to another component. The components on the surface of the support may be laid out in any convenient configuration. Where two or more components are present on the surface of the solid support, interconnects may be provided.

As indicated above, the system, such as system 2100 and 2040, control the conductance between the dissimilar materials and, hence, the rate of ionic exchange or the current flow. Through altering the conductance in a specific manner the system is capable of encoding information in the ionic exchange and the current signature. The ionic exchange or the current signature is used to uniquely identify the specific system. Additionally, the systems 2100 and 2040 are capable of producing various different unique exchanges or signatures and, thus, provide additional information. For example, a second current signature based on a second conductance alteration pattern may be used to provide additional information, which information may be related to the physical environment. To further illustrate, a first current signature may be a very low current state that maintains an oscillator on the chip and a second current signature may be a current state at least a factor of ten higher than the current state associated with the first current signature.

Figure 23B:
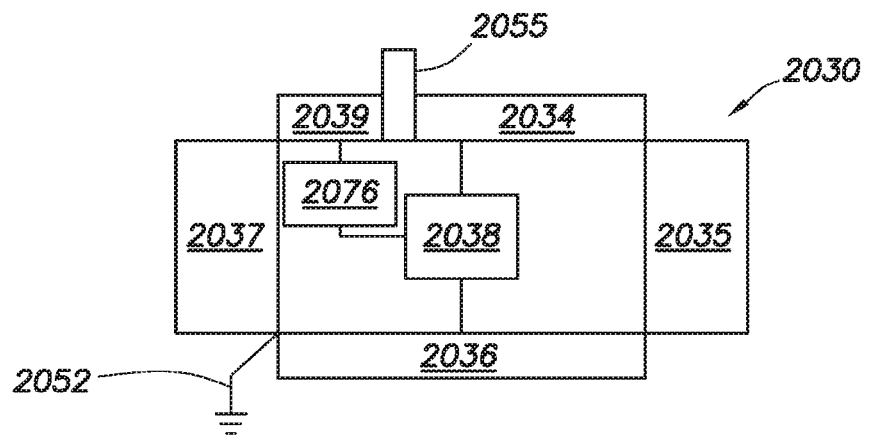
FIG. 23B shows the event indicator system of FIG. 23 with a pH sensor unit.
Figure 24:
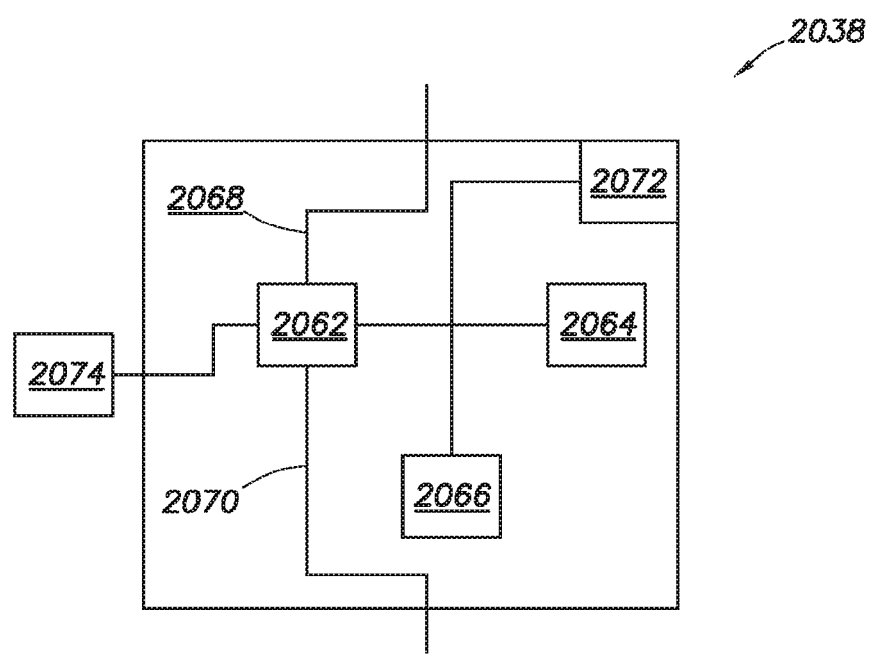
FIG. 24 is a block diagram illustration of one aspect of the control device used in the system of FIGS. 21 and 22.
Figure 25:
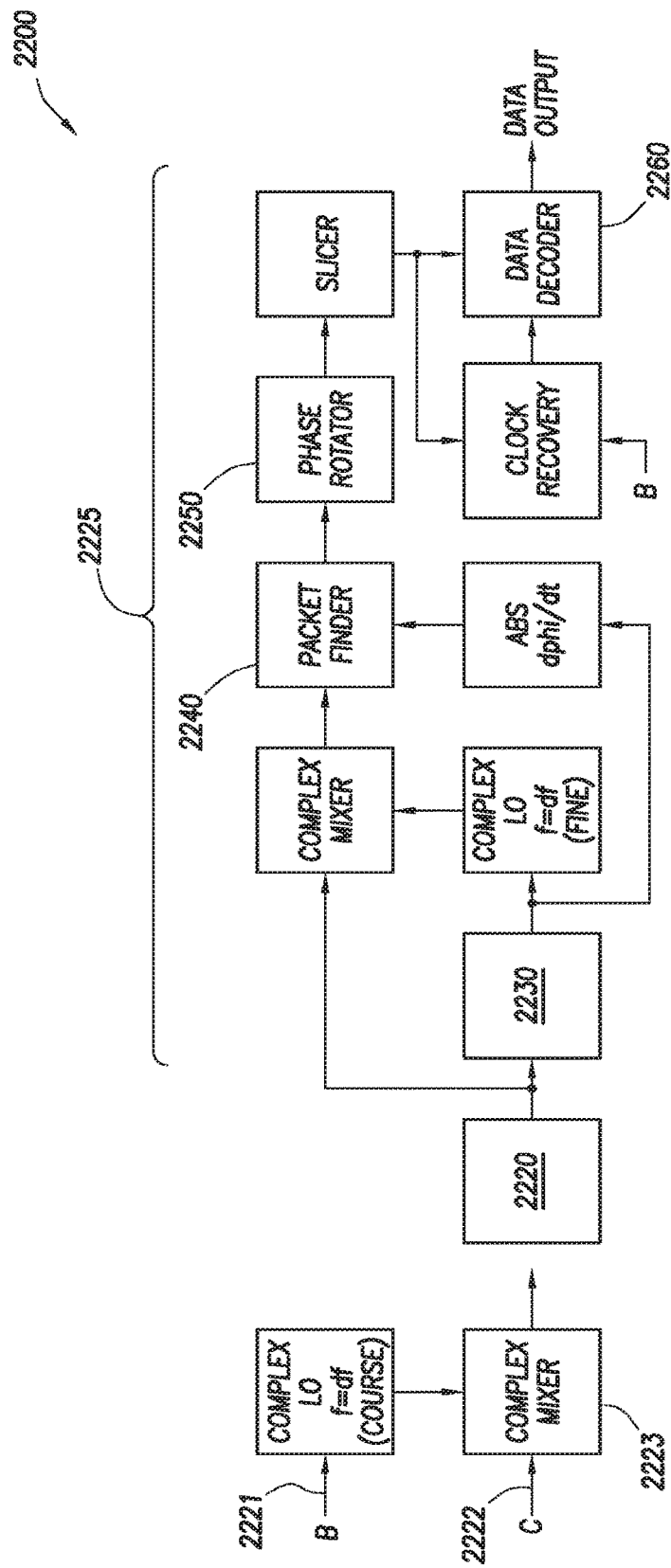
FIG. 25 is a functional block diagram of a demodulation circuit that performs coherent demodulation that may be present in a receiver, according to one aspect.
Figure 26:
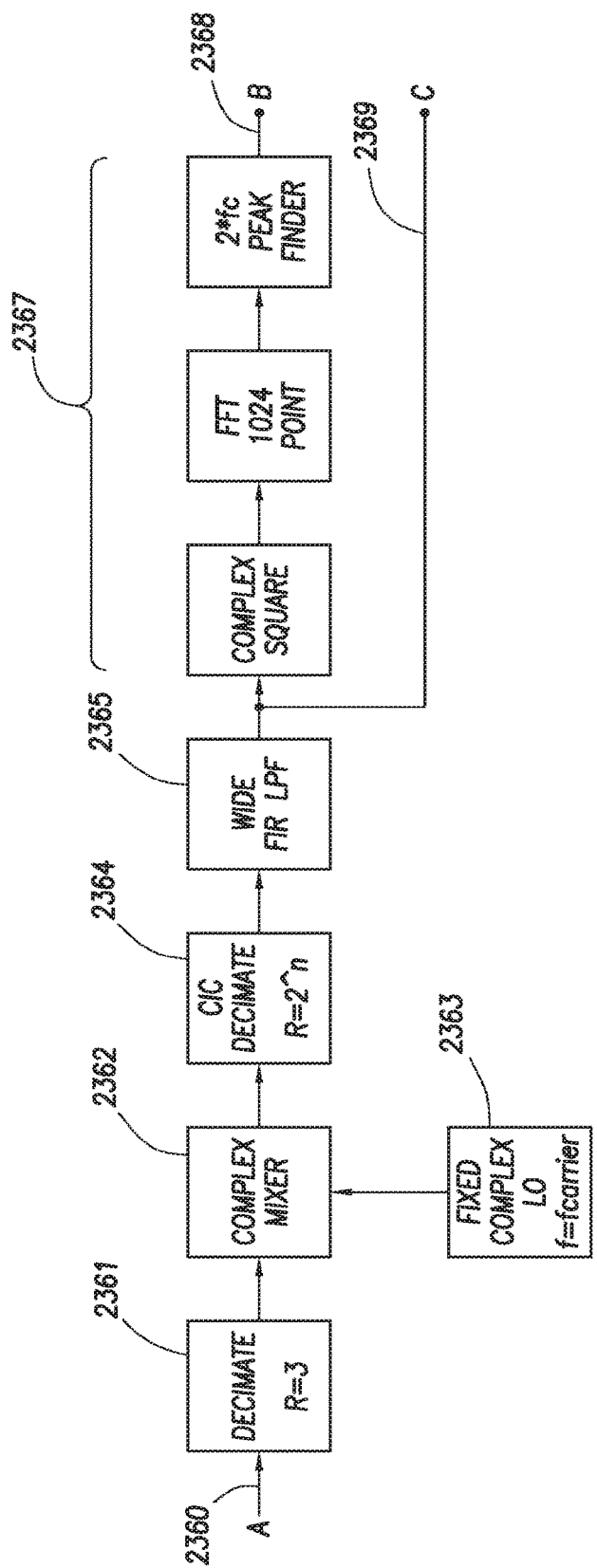
FIG. 26 illustrates a functional block diagram for a beacon module within a receiver, according to one aspect.
Figure 27:
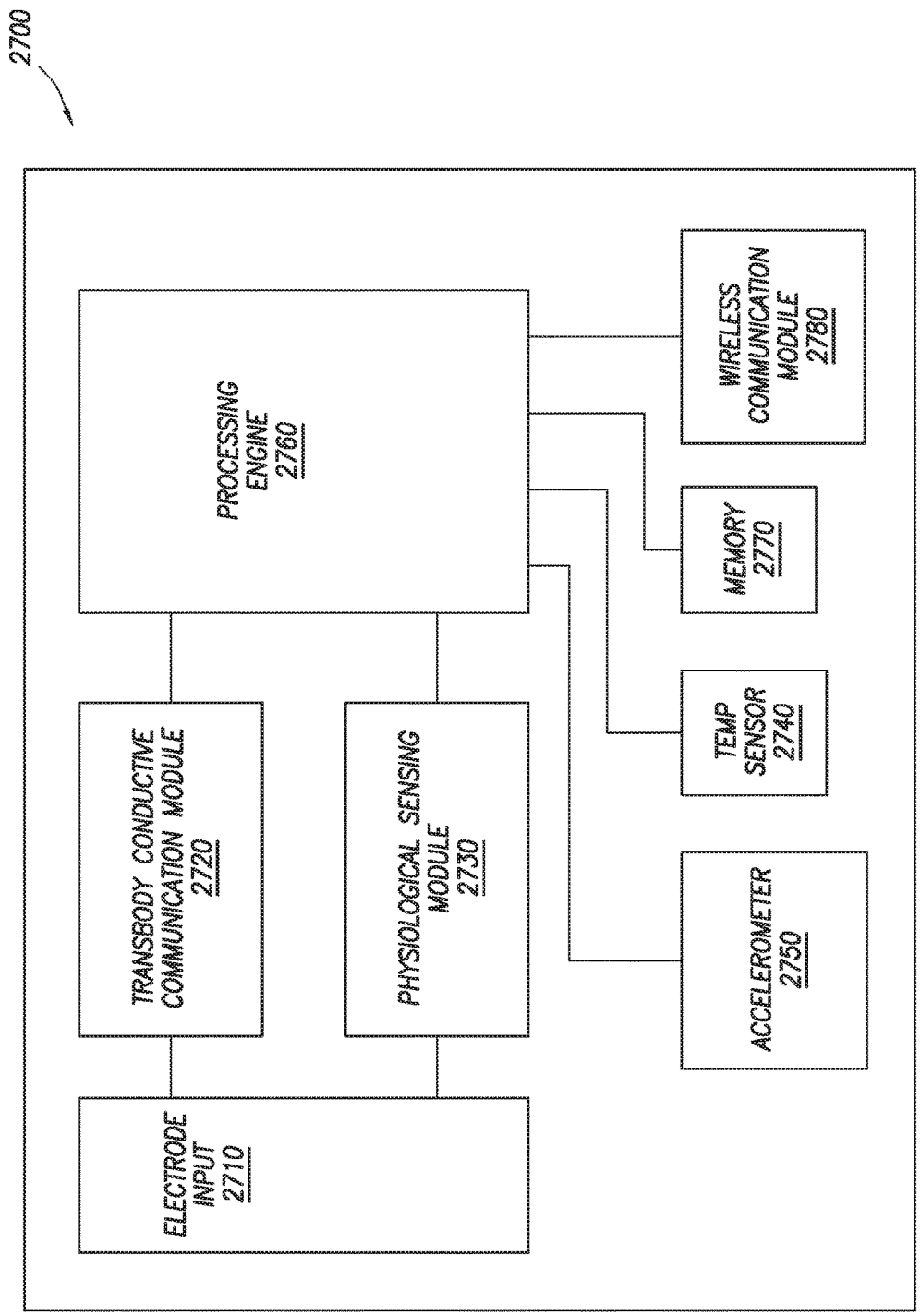
FIG. 27 is a block diagram of the different functional modules that may be present in a receiver, according to one aspect.
Figure 28:
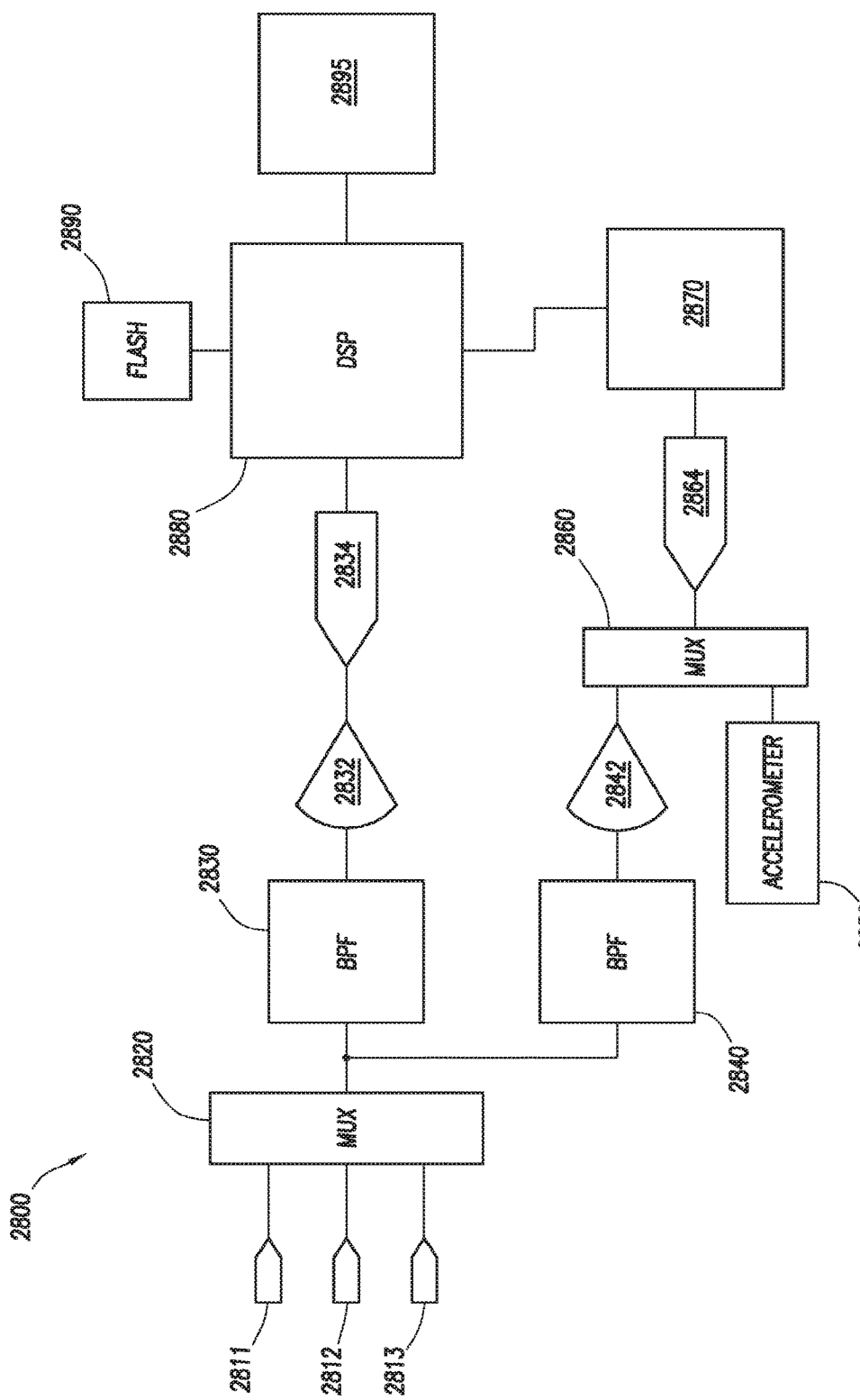
FIG. 28 is a block diagram of a receiver, according to one aspect.

Referring now to FIG. 24, a block diagram representation of the control device 2038 is shown. The device 2030 includes a control module 2062, a counter or clock 2064, and a memory 2066. Additionally, the device 2038 is shown to include a sensor module 2072 as well as the sensor module 2074, which was referenced in FIG. 23. The control module 2062 has an input 2068 electrically coupled to the material 2034 and an output 2070 electrically coupled to the material 2036. The control module 2062, the clock 2064, the memory 2066, and the sensor modules 2072/2074 also have power inputs (some not shown). The power for each of these components is supplied by the voltage potential produced by the chemical reaction between materials 2034 and 2036 and the conducting fluid, when the system 2030 is in contact with the conducting fluid. The control module 2062 controls the conductance through logic that alters the overall impedance of the system 2030. The control module 2062 is electrically coupled to the clock 2064. The clock 2064 provides a clock cycle to the control module 2062. Based upon the programmed characteristics of the control module 2062, when a set number of clock cycles have passed, the control module 2062 alters the conductance characteristics between materials 2034 and 2036. This cycle is repeated and thereby the control device 2038 produces a unique current signature characteristic. The control module 2062 is also electrically coupled to the memory 2066. Both the clock 2064 and the memory 2066 are powered by the voltage potential created between the materials 2034 and 2036. The control module 2062 is also electrically coupled to and in communication with the sensor modules 2072 and 2074. In the aspect shown, the sensor module 2072 is part of the control device 2038 and the sensor module 2074 is a separate component. In alternative aspects, either one of the sensor modules 2072 and 2074 can be used without the other and the scope of the present invention is not limited by the structural or functional location of the sensor modules 2072 or 2074. Additionally, any component of the system 2030 may be functionally or structurally moved, combined, or repositioned without limiting the scope of the present invention as claimed. Thus, it is possible to have one single structure, for example a processor, which is designed to perform the functions of all of the following modules: the control module 2062, the clock 2064, the memory 2066, and the sensor module 2072 or 2074. On the other hand, it is also within the scope of the present invention to have each of these functional components located in independent structures that are linked electrically and able to communicate. Referring again to FIG. 24, the sensor modules 2072 or 2074 can include any of the following sensors: temperature, pressure, pH level, and conductivity. In one aspect, the sensor modules 2072 or 2074 gather information from the environment and communicate the analog information to the control module 2062. The control module then converts the analog information to digital information and the digital information is encoded in the current flow or the rate of the transfer of mass that produces the ionic flow. In another aspect, the sensor modules 2072 or 2074 gather information from the environment and convert the analog information to digital information and then communicate the digital information to control module 2062. In the aspect shown in FIG. 23, the sensor modules 2074 is shown as being electrically coupled to the material 2034 and 2036 as well as the control device 2038. In another aspect, as shown in FIG. 24, the sensor module 2074 is electrically coupled to the control device and the connection acts as both a source for power supply to the sensor module 2074 and a communication channel between the sensor module 2074 and the control device 2038. Referring now to FIG. 23B, the system 2030 includes a pH sensor module 2076 connected to a material 2039, which is selected in accordance with the specific type of sensing function being performed. The pH sensor module 2076 is also connected to the control device 2038. The material 2039 is electrically isolated from the material 2034 by a non-conductive barrier 2055. In one aspect, the material 2039 is platinum. In operation, the pH sensor module 2076 uses the voltage potential difference between the materials 2034/2036. The pH sensor module 2076 measures the voltage potential difference between the material 2034 and the material 2039 and records that value for later comparison. The pH sensor module 2076 also measures the voltage potential difference between the material 2039 and the material 2036 and records that value for later comparison. The pH sensor module 2076 calculates the pH level of the surrounding environment using the voltage potential values. The pH sensor module 2076 provides that information to the control device 2038. The control device 2038 varies the rate of the transfer of mass that produces the ionic transfer and the current flow to encode the information relevant to the pH level in the ionic transfer, which can be detected by a receiver (not shown). Thus, the system 2030 can determine and provide the information related to the pH level to a source external to the environment. As indicated above, the control device 2038 can be programmed in advance to output a pre-defined current signature. In another aspect, the system can include a receiver system that can receive programming information when the system is activated. In another aspect, not shown, the switch 2064 and the memory 2066 can be combined into one device. In addition to the above components, the system 2030 may also include one or other electronic components. Electrical components of interest include, but are not limited to: additional logic and/or memory elements, e.g., in the form of an integrated circuit; a power regulation device, e.g., battery, fuel cell or capacitor; a sensor, a stimulator, etc.; a signal transmission element, e.g., in the form of an antenna, electrode, coil, etc.; a passive element, e.g., an inductor, resistor, etc. It will be appreciated that in the interest of conciseness and clarity, although the plug/jack connection arrangement has been disclosed herein, other suitable connection arrangements are contemplated to be within the scope of the present disclosure. Such other connection arrangements include, without limitation, any electrical connector that is an electro-mechanical device for joining electrical circuits as an interface using a mechanical arrangement. The connection may be temporary, as for portable equipment, require a tool for arrangement and removal, or serve as a permanent electrical joint between two wires or devices. Those skilled in the art will appreciate that there are hundreds of types of electrical connectors for joining two lengths of flexible wire or cable, or connect a wire or cable or optical interface to an electrical terminal. In the context of the present disclosure, an electrical connector also may be referred to as a physical interface. Such connectors include, without limitation, plug and socket, audio/video, posts, keyed and unkeyed, locked and unlocked, modular multi-conductor plug and jacks commonly used for Ethernet/Cat5 applications, D-subminiature, data ports, USB, RF, direct current (DC), hybrid, among other suitable connection mechanisms.

It also will be appreciated that as described in the present disclosure, various ordinary objects have been modified to include electrodes to pick up the unique electrical current signature generated by the IEM device. Such ordinary objects include headphones with ear buds 108 as shown in FIGS. 1-4, a mobile device 800 as shown in FIGS. 8-10, a mobile device enclosing arrangement 1102 as shown in FIGS. 11-13, eyeglasses 1504, 1608 as shown in FIGS. 15-16, a visor as shown in FIG. 17, a helmet 1808 as shown in FIG. 18, hearing aids 1904R, 1904L as shown in FIG. 19, and a chair 2008 as shown in FIG. 20. It will be appreciated, however, that the present disclosure is not limited in this context and it is contemplated that any suitable ordinary object can be modified to include a set of electrodes to carry the unique electrical current signal generated by the IEM device when the patient holds the object and makes physical contact with the electrodes after ingesting the IEM and associated medication. For example, other ordinary objects that can be modified to incorporate the electrodes include, without limitation, ear muffs, hats, drinking glasses, eating utensils (chopsticks, knife, spoon, fork), remote control devices entertainment systems (television, stereo, DVD player), portable media players (iPod by Apple, MP3 devices), computer keyboards, computer mouse, tabletop, medicine containers (pill bottles, vitamin bottles, inhalable dosing units), cardboard packaging of the medicine containers, head bands, hair bands, motorcycle helmets, ski helmets, goggles, ski goggles, coffee cups, toothbrushes, canes, walkers, bracelets, belts, suspenders, medic alert bracelets, steering wheel of a vehicle (car, truck), keys, house keys, vehicle (car, truck) keys, musical instruments (keyboards, saxophone), laptop computer, iPad by Apple or other tablet computer, e-book reader (Kindle by Amazon), purse, purse handles, gloves, mittens, business card holder, thimbles, pulse oximeters, salt and pepper shakers, beverage decanters (milk, wine), beverage bottles or cans (soda, juice, water) dentures, electronic scales, thermometers, stuffed animals (especially for children), exercise equipment (elliptical machine, dumbbells, weightlifting, exercise ball, stationary bike), digital camera (still or motion image camera), board games (Scrabble, Monopoly, chess), digital recording device, Dictaphone, among others.

It also will be appreciated that as described in the present disclosure, that the mobile devices that incorporate an image capture device (e.g., a digital camera) may be used to capture an image of the IEM device, medication, container in which the medication, among others. Once the image is captured it can be used to verify the patient taking the medication, the medication itself, expiration dates on the package, among other information. The digitally captured image can be stored, compressed, transmitted over local and wide area networks (such as the Internet), and so on.

It is worthy to note that any reference to "one aspect" or "an aspect" means that a particular feature, structure, or characteristic described in connection with the aspect is included in at least one aspect. Thus, appearances of the phrases "in one aspect" or "in an aspect" in various places throughout the specification are not necessarily all referring to the same aspect. Furthermore, the particular features, structures or characteristics may be combined in any suitable manner in one or more aspects.

Some aspects may be described using the expression "coupled" and "connected" along with their derivatives. It should be understood that these terms are not intended as synonyms for each other. For example, some aspects may be described using the term "connected" to indicate that two or more elements are in direct physical or electrical contact with each other. In another example, some aspects may be described using the term "coupled" to indicate that two or more elements are in direct physical or electrical contact. The term "coupled," however, also may mean that two or more elements are not in direct contact with each other, but yet still co-operate or interact with each other. Notwithstanding the claims, the invention is also defined by the following clauses:

1. A mobile device for detecting an electrical signal generated by an ingestible event marker, the mobile device comprising:
   a detection subsystem to receive an electrical signal generated by an ingestible event marker from a detection arrangement, preferably wherein the detection subsystem comprises an electrode input circuit to receive the electrical signal from the detection arrangement,
   a processing subsystem coupled to the detection subsystem to decode the electrical signal; and
   a radio subsystem configured to transmit the decoded electrical signal to a wireless node.

2. The mobile device of clause 1, comprising one or more of the following:
   a connector to receive a plug coupled to the detection arrangement,
   a housing, wherein the detection arrangement is integrated with the housing,
   an application software program comprising a series of computer executable instructions executable by the processing system, wherein when the computer executable instructions are executed by the processing subsystem causes the radio subsystem to initiate communication with the wireless node.

3. The mobile device according to clauses 1 or 2 wherein the detection subsystem comprises an electrode input circuit to receive the electrical signal from the detection arrangement.

4. The mobile device according to any of the preceding clauses further comprising a connector coupled to the electrode input circuit and the detection arrangement comprises a plug to be received in the connector.

5. A system for detecting an electrical signal generated by an ingestible event marker, the system comprising:
   a mobile device according to any of the preceding clauses and
   a detection arrangement to couple to the mobile device.

6. The system of clause 5, comprising a cover to receive the mobile device, wherein the detection subsystem is located in the enclosing arrangement.

7. The system of clause 5 or 6, wherein the processing subsystem is located in the cover.

8. The system of clause 6 or 7, wherein the cover comprises a connector to couple to the detection subsystem of the processing to receive the processing subsystem of the mobile device.

9. The system according to any of the clauses 5-8 wherein the detection arrangement comprises:
   at least one electrode to couple to a living body; and
   a plug having a first end wiredly coupled to the at least one electrode and a second end wiredly coupled to a connector of the mobile device to wiredly connect the at least one electrode to the detection subsystem of the mobile device.

10. The system according to any of the clauses 5-8 wherein the detection arrangement comprises:
    at least one electrode to couple to a living body;
    a detection circuit module coupled to the at least one electrode; and
    an antenna coupled to the detection circuit module.

11. The system of clause 10, wherein the detection arrangement is wirelessly coupled to the mobile device.

12. The system according to any of the clauses 5-11 wherein the detection arrangement is located in an object, preferably selected from the group consisting essentially of headphones with ear buds, a mobile device, a mobile device cover, eyeglasses, a visor, and a helmet.

13. The system according to any of the preceding clauses 5-12 further comprising an ingestible event marker.

15. A method of processing an electrical signal generated by an ingestible event marker, the method comprising:
    receiving an electrical signal generated by an ingestible event marker at a mobile device, the mobile device preferably according to any of the preceding clauses 1-4,
    decoding the electrical signal received by the mobile device to extract information associated with the ingestible event marker; and transmitting the information to a wireless node.

16. The method of clause 15, further comprising transmitting the information to a remote node.

17. Use of a mobile device and/or a system according to any of the preceding clauses 1-4, 5-13 respectively for detecting an electrical signal generated by an ingestible event marker.

While certain features of the aspects have been illustrated as described herein, many modifications, substitutions, changes and equivalents will now occur to those skilled in the art. It is therefore to be understood that the appended claims are intended to cover all such modifications and changes as fall within the true spirit of the aspects.

The invention claimed is:

1. A mobile device for detecting an electrical signal generated by an ingestible event marker, the mobile device comprising:
   a housing;
   a first electrode and a second electrode integrated with the housing, the first and second electrodes configured to receive the electrical signal generated by the ingestible event marker;
   a detection subsystem coupled to the first and second electrodes, the detection subsystem configured to decode the electrical signal generated by the ingestible event marker received via the first and second electrodes; and
   a radio subsystem configured to transmit the decoded electrical signal to a wireless node.

2. The mobile device of claim 1, wherein the detection subsystem comprises an electrode input circuit to receive the electrical signal from the first and second electrodes.

3. The mobile device of claim 1, comprising computer executable instructions stored on a memory coupled to a processor that, when executed by the processor, cause the radio subsystem to initiate communication with the wireless node.

4. The mobile device of claim 1, wherein the detection subsystem is configured to receive the electrical signal generated by the ingestible event marker when both the first and second electrodes are contacted by a user ingesting the ingestible event marker.

5. A system for detecting an electrical signal generated by an ingestible event marker, the system comprising:
   a housing configured to at last partially enclose a mobile device;
   a first electrode and a second electrode integrated with the housing, the first and second electrodes configured to receive the electrical signal generated by the ingestible event marker;

a detection circuit coupled to the first and second electrodes, the detection circuit configured to decode the electrical signal generated by the ingestible event marker received via the first and second electrodes; and a wireless communication module coupled to the detection circuit, the wireless communication module configured to transmit the decoded electrical signal to the mobile device.

6. The system of claim 5, wherein at least one of the detection circuit and the wireless communication module are located in the housing.

7. The mobile device of claim 5, wherein the detection circuit is configured to receive the electrical signal generated by the ingestible event marker when both the first and second electrodes are contacted by a user ingesting the ingestible event marker.

* * * * *